US008507253B2

(12) United States Patent  
Berzin

(10) Patent No.: US 8,507,253 B2  
(45) Date of Patent: Aug. 13, 2013

(54) PHOTOBIOREACTOR CELL CULTURE SYSTEMS, METHODS FOR PRECONDITIONING PHOTOSYNTHETIC ORGANISMS, AND CULTURES OF PHOTOSYNTHETIC ORGANISMS PRODUCED THEREBY

(75) Inventor: Isaac Berzin, Talbiya (IL)

(73) Assignee: Algae Systems, LLC, Reno, NV (US)

( * ) Notice: Subject to any disclaimer, the term of this patent is extended or adjusted under 35 U.S.C. 154(b) by 1408 days.

(21) Appl. No.: 11/632,541

(22) PCT Filed: Jul. 18, 2005

(86) PCT No.: PCT/US2005/025367  
§ 371 (c)(1),  
(2), (4) Date: Mar. 14, 2008

(87) PCT Pub. No.: WO2006/020177  
PCT Pub. Date: Feb. 23, 2006

(65) Prior Publication Data  
US 2009/0011492 A1 Jan. 8, 2009

Related U.S. Application Data

(63) Continuation-in-part of application No. 11/106,695, filed on Apr. 14, 2005, now abandoned, which is a continuation-in-part of application No. 10/924,742, filed on Aug. 23, 2004, now abandoned, which is a continuation-in-part of application No. 10/514,224, filed as application No. PCT/US03/15364 on May 13, 2003, now abandoned.

(60) Provisional application No. 60/589,527, filed on Jul. 16, 2004, provisional application No. 60/562,057, filed on Apr. 14, 2004, provisional application No. 60/497,445, filed on Aug. 22, 2003, provisional application No. 60/380,179, filed on May 13, 2002.

(51) Int. Cl.  
C12N 1/00 (2006.01)  
C12M 1/00 (2006.01)  
C12M 1/42 (2006.01)  
C12M 3/00 (2006.01)  
A61L 9/01 (2006.01)  
C02F 3/32 (2006.01)  
C02F 3/00 (2006.01)

(52) U.S. Cl.  
USPC ..... 435/257.1; 435/243; 435/266; 435/283.1; 435/289.1; 435/292.1; 47/1.4; 210/601; 210/602

(58) Field of Classification Search  
None  
See application file for complete search history.

(56) References Cited

U.S. PATENT DOCUMENTS

| 1,995,970 | A | 3/1935 | Dorough |
| 2,703,316 | A | 3/1955 | Schneider |
| 2,807,912 | A | 10/1957 | Bjorksten |
| 2,854,792 | A | 10/1958 | Juda |
| 3,420,737 | A | 1/1969 | Bongers et al. |
| 3,420,739 | A | 1/1969 | Bongers et al. |
| 3,456,928 | A | 7/1969 | Selway |
| 3,468,057 | A | 9/1969 | Buisson et al. |
| 3,492,789 | A | 2/1970 | Jueng |
| 3,579,907 | A | 5/1971 | Graves |
| 3,592,631 | A | 7/1971 | Cattelain |
| 3,650,068 | A | 3/1972 | Meyer et al. |
| 3,954,615 | A | 5/1976 | Shelef |
| 3,954,921 | A | 5/1976 | Yoshida et al. |
| 3,955,317 | A | 5/1976 | Gudin |
| 3,998,186 | A | 12/1976 | Hodges |
| 4,005,015 | A | 1/1977 | Boward, Jr. |
| 4,044,500 | A | 8/1977 | Hitzman |
| 4,169,050 | A | 9/1979 | Serfling et al. |
| 4,209,943 | A | 7/1980 | Moeller et al. |
| 4,217,728 | A | 8/1980 | Shimamatsu et al. |
| 4,233,958 | A | 11/1980 | Heden |
| 4,253,271 | A | 3/1981 | Raymond |
| 4,341,038 | A | 7/1982 | Bloch et al. |
| 4,442,211 | A | 4/1984 | Greenbaum |
| 4,446,236 | A | 5/1984 | Clyde |
| 4,473,970 | A | 10/1984 | Hills |
| 4,532,210 | A | 7/1985 | Miura et al. |

(Continued)

FOREIGN PATENT DOCUMENTS

| AT | 154828 T | 7/1997 |
| AU | 3000084 A | 1/1985 |

(Continued)

OTHER PUBLICATIONS

H.C.P. Matthijs, H. Balke, U.M. Van Hes, B.M.A. Kroon, L.R. Mur and R.A. Binot, "Application of Light-emitting Diodes in Bioreactors: Flashing Light Effects and Energy Economy in Algal Culture (*Chlorella pyrenoidosa*)" Biotechnol Bioeng, 1996, 50 (1), pp. 98-107.*

Maeda,K; Owada,M; Kimura,N; Omata, K;Karube,I "CO2 Fixation from the Flue Gas on Coal-Fired Thermal Power Plant by Microalgae" Energy Conversion and Management, Jun.-Sep. 1995, 36(6-9), pp. 717-720.*

Brown, Lewis M. "Uptake of Carbon Dioxide from Flue Gas by Microalgae" Energy Conversion and Management, Jun.-Aug. 1996, 37(6-8), pp. 1363-1367.*

(Continued)

Primary Examiner — Jon P Weber  
Assistant Examiner — Aaron J Kosar  
(74) Attorney, Agent, or Firm — Peters Verny, LLP

(57) ABSTRACT

Certain embodiments of the invention involve methods and systems for preselecting, adapting, and preconditioning one or more species of photosynthetic organisms, such as algae, to specific environmental and/or operating conditions to which the photosynthetic organisms will subsequently be exposed during utilization in a photobioreactor apparatus of a gas treatment system. Also disclosed are new algal strains and cultures that can be produced by practicing the preselection, adaption, and preconditioning methods.

23 Claims, 21 Drawing Sheets

(56) References Cited

U.S. PATENT DOCUMENTS

| | | |
|---|---|---|
| 4,577,110 A | 3/1986 | MacBride |
| 4,653,223 A | 3/1987 | Mori |
| 4,658,757 A | 4/1987 | Cook |
| 4,666,852 A | 5/1987 | Cork |
| 4,676,959 A | 6/1987 | Mori |
| 4,786,598 A | 11/1988 | Lafferty et al. |
| 4,828,768 A | 5/1989 | Talmor |
| 4,868,123 A | 9/1989 | Berson et al. |
| 4,888,912 A | 12/1989 | Murray |
| 4,963,486 A | 10/1990 | Hang |
| 4,999,302 A | 3/1991 | Kahler et al. |
| 5,104,589 A | 4/1992 | Palmer et al. |
| 5,137,828 A | 8/1992 | Robinson et al. |
| 5,142,023 A | 8/1992 | Gruber et al. |
| 5,151,347 A | 9/1992 | Delente et al. |
| 5,162,051 A | 11/1992 | Hoeksema |
| 5,213,976 A | 5/1993 | Blauhut et al. |
| 5,216,976 A | 6/1993 | Marinkovich |
| 5,242,827 A | 9/1993 | Chaumont et al. |
| 5,247,058 A | 9/1993 | Gruber et al. |
| 5,247,059 A | 9/1993 | Gruber et al. |
| 5,250,427 A | 10/1993 | Weaver et al. |
| 5,258,488 A | 11/1993 | Gruber et al. |
| 5,269,819 A | 12/1993 | Porath |
| 5,274,073 A | 12/1993 | Gruber et al. |
| 5,310,865 A | 5/1994 | Enomoto et al. |
| 5,330,639 A | 7/1994 | Murphree |
| 5,338,673 A | 8/1994 | Thepenier et al. |
| 5,344,557 A | 9/1994 | Scanzillo |
| 5,357,035 A | 10/1994 | Gruber et al. |
| 5,359,026 A | 10/1994 | Gruber |
| 5,424,209 A | 6/1995 | Kearney |
| 5,440,008 A | 8/1995 | Ichikawa et al. |
| 5,443,985 A | 8/1995 | Lu et al. |
| 5,444,143 A | 8/1995 | Ohta et al. |
| 5,447,629 A | 9/1995 | Chaumont et al. |
| 2,732,663 A | 1/1996 | Dewey, II |
| 5,496,923 A | 3/1996 | Suizu et al. |
| 5,510,526 A | 4/1996 | Baniel et al. |
| 5,512,653 A | 4/1996 | Ohta et al. |
| 5,528,856 A | 6/1996 | Smith et al. |
| 5,534,417 A | 7/1996 | Arad et al. |
| 5,541,056 A | 7/1996 | Huntley et al. |
| 5,554,291 A | 9/1996 | Scanzillo |
| 5,591,341 A | 1/1997 | Jensen |
| 5,594,095 A | 1/1997 | Gruber et al. |
| 5,606,170 A | 2/1997 | Saaski et al. |
| 5,612,188 A | 3/1997 | Shuler et al. |
| 5,614,378 A | 3/1997 | Yang et al. |
| 5,628,311 A | 5/1997 | Mauze |
| 5,636,472 A | 6/1997 | Spira et al. |
| 5,659,977 A | 8/1997 | Jensen et al. |
| 5,661,017 A | 8/1997 | Dunahay et al. |
| 5,670,046 A | 9/1997 | Kimmel |
| 5,679,767 A | 10/1997 | Suizu et al. |
| 5,686,276 A | 11/1997 | Laffend et al. |
| 5,691,424 A | 11/1997 | Suzuki et al. |
| 5,714,573 A | 2/1998 | Randall et al. |
| 5,741,702 A | 4/1998 | Lorenz |
| 5,766,474 A | 6/1998 | Smith |
| 5,770,683 A | 6/1998 | Yoshida et al. |
| 5,780,678 A | 7/1998 | Baniel et al. |
| 5,786,185 A | 7/1998 | Tsao et al. |
| 5,798,435 A | 8/1998 | Gruber et al. |
| 5,846,816 A | 12/1998 | Forth |
| 5,882,849 A | 3/1999 | Leonard et al. |
| 5,892,109 A | 4/1999 | Baniel et al. |
| 5,910,254 A | 6/1999 | Guelcher et al. |
| 5,917,010 A | 6/1999 | Goto et al. |
| 5,922,832 A | 7/1999 | Randall et al. |
| 5,942,597 A | 8/1999 | Noda et al. |
| 5,958,761 A | 9/1999 | Yogev et al. |
| 5,981,271 A | 11/1999 | Doucha et al. |
| 5,998,552 A | 12/1999 | Gruber et al. |
| 6,005,067 A | 12/1999 | Gruber et al. |
| 6,022,701 A | 2/2000 | Boussiba et al. |
| 6,025,184 A | 2/2000 | Laffend et al. |
| 6,037,170 A | 3/2000 | Sekine |
| 6,051,437 A | 4/2000 | Luo et al. |
| 6,083,740 A | 7/2000 | Kodo et al. |
| 6,087,532 A | 7/2000 | Baniel et al. |
| 6,111,137 A | 8/2000 | Suizu et al. |
| 6,140,458 A | 10/2000 | Terado et al. |
| 6,156,561 A | 12/2000 | Kodo et al. |
| 6,174,720 B1 | 1/2001 | Oxley et al. |
| 6,187,951 B1 | 2/2001 | Baniel et al. |
| 6,218,173 B1 | 4/2001 | Naito |
| 6,229,046 B1 | 5/2001 | Eyal et al. |
| 6,277,951 B1 | 8/2001 | Gruber et al. |
| 6,285,807 B1 | 9/2001 | Walt et al. |
| 6,291,597 B1 | 9/2001 | Gruber et al. |
| 6,320,077 B1 | 11/2001 | Eyal et al. |
| 6,326,458 B1 | 12/2001 | Gruber et al. |
| 6,348,347 B1 | 2/2002 | Hirabayashi et al. |
| 6,370,815 B1 | 4/2002 | Skill et al. |
| 6,416,993 B1 * | 7/2002 | Wexler et al. .............. 435/262.5 |
| 6,417,266 B1 | 7/2002 | Terado et al. |
| 6,428,767 B1 | 8/2002 | Burch et al. |
| 6,429,280 B1 | 8/2002 | Hiraoka et al. |
| 6,465,240 B1 | 10/2002 | Wexler et al. |
| 6,472,559 B2 | 10/2002 | Baniel et al. |
| 6,475,759 B1 | 11/2002 | Carlson et al. |
| 6,485,947 B1 | 11/2002 | Rajgarhia et al. |
| 6,492,149 B1 | 12/2002 | Muller-Feuga |
| 6,495,631 B1 | 12/2002 | Randall et al. |
| 6,509,188 B1 | 1/2003 | Trosch et al. |
| 6,534,679 B2 | 3/2003 | Eyal et al. |
| 6,575,714 B2 | 6/2003 | Pace et al. |
| 6,579,714 B1 | 6/2003 | Hirabayashi et al. |
| 6,602,703 B2 | 8/2003 | Dutil |
| 6,603,069 B1 | 8/2003 | Muhs et al. |
| 6,616,845 B2 | 9/2003 | Shechter et al. |
| 6,648,949 B1 | 11/2003 | Der et al. |
| 6,667,171 B2 | 12/2003 | Bayless et al. |
| 6,673,532 B2 | 1/2004 | Rao |
| 6,706,963 B2 | 3/2004 | Gaudiana et al. |
| 6,726,838 B2 | 4/2004 | Shechter et al. |
| 6,827,036 B2 | 12/2004 | Connolly |
| 7,523,370 B1 | 4/2009 | Keller |
| 7,755,675 B2 | 7/2010 | Ejima et al. |
| 2002/0072109 A1 | 6/2002 | Bayless et al. |
| 2002/0146817 A1 | 10/2002 | Cannon et al. |
| 2003/0040104 A1 | 2/2003 | Barbera-Guillen |
| 2003/0056821 A1 | 3/2003 | Chittibaba et al. |
| 2003/0160500 A1 | 8/2003 | Drake et al. |
| 2003/0188777 A1 | 10/2003 | Gaudiana |
| 2003/0189402 A1 | 10/2003 | Gaudiana |
| 2003/0192583 A1 | 10/2003 | Ryan |
| 2003/0192584 A1 | 10/2003 | Beckenbaugh |
| 2003/0192585 A1 | 10/2003 | Beckenbaugh |
| 2003/0230337 A1 | 12/2003 | Gaudiana |
| 2004/0025933 A1 | 2/2004 | Chittibabu |
| 2004/0025934 A1 | 2/2004 | Chittibabu |
| 2004/0031520 A1 | 2/2004 | Ryan |
| 2004/0089592 A1 | 5/2004 | Shechter et al. |
| 2004/0118447 A1 | 6/2004 | Muhs |
| 2004/0118448 A1 | 6/2004 | Scher |
| 2004/0207102 A1 | 10/2004 | Sugimori et al. |
| 2004/0209256 A1 | 10/2004 | Dillon |
| 2004/0262980 A1 | 12/2004 | Watson |
| 2005/0014239 A1 | 1/2005 | Melis et al. |
| 2005/0025367 A1 | 2/2005 | Jodoin |
| 2005/0064577 A1 | 3/2005 | Berzin |
| 2005/0239182 A1 | 10/2005 | Berzin |
| 2005/0260553 A1 | 11/2005 | Berzin |
| 2006/0016760 A1 | 1/2006 | Bozak et al. |
| 2006/0048920 A1 | 3/2006 | Helleur |
| 2007/0048848 A1 | 3/2007 | Sears |
| 2008/0009055 A1 | 1/2008 | Lewnard |
| 2008/0178739 A1 | 7/2008 | Lewnard |
| 2009/0011492 A1 | 1/2009 | Berzin |
| 2009/0130706 A1 | 5/2009 | Berzin et al. |

FOREIGN PATENT DOCUMENTS

| | | |
|---|---|---|
| AU | 543516 B2 | 4/1985 |
| AU | 2294788 A | 4/1989 |
| AU | 654114 B2 | 10/1994 |
| AU | 7131696 A | 4/1997 |
| AU | 704463 B2 | 4/1999 |
| AU | 722744 B2 | 8/2000 |
| AU | 2005274791 A1 | 2/2006 |
| AU | 2007273128 A1 | 1/2008 |
| BR | 9007742 A | 11/1992 |
| CA | 1256770 A1 | 7/1989 |
| CA | 2067348 A1 | 11/1991 |
| CA | 2232707 A1 | 3/1997 |
| DE | 282839 A5 | 9/1990 |
| DE | 3888274 T2 | 9/1994 |
| DE | 4411486 C1 | 3/1995 |
| DE | 4420392 A1 | 12/1995 |
| DE | 69030976 T2 | 7/1997 |
| DE | 69030976 T2 | 10/1997 |
| EP | 0130586 A2 | 1/1985 |
| EP | 0310522 A | 4/1989 |
| EP | 0343885 A1 | 11/1989 |
| EP | EP 0494887 B1 | 6/1997 |
| EP | 0852616 A1 | 7/1998 |
| EP | 2046938 A2 | 4/2009 |
| EP | 2152848 | 2/2010 |
| ES | 434392 A1 | 4/1977 |
| ES | 2103745 T3 | 10/1997 |
| FR | 2324224 A1 | 4/1977 |
| FR | 2596412 A1 | 3/1986 |
| FR | 2621323 A1 | 4/1989 |
| GB | 1189096 | 4/1970 |
| GB | 1495709 A | 12/1977 |
| GB | 2118572 A | 11/1983 |
| IL | 87832 A | 3/1992 |
| IT | 1033117 B | 7/1979 |
| IT | 01241751 | 10/1990 |
| JP | 50105881 A | 8/1975 |
| JP | 52028990 A | 3/1977 |
| JP | 58035676 B | 8/1983 |
| JP | 1201436 C | 4/1984 |
| JP | 60012913 A | 1/1985 |
| JP | 1108973 A | 4/1989 |
| JP | 02104231 A | 4/1990 |
| JP | 2058896 B | 12/1990 |
| JP | 1630175 C | 12/1991 |
| JP | 5503418 T | 6/1993 |
| JP | 05184347 A | 7/1993 |
| JP | 05184348 A | 7/1993 |
| JP | 5184348 A | 7/1993 |
| JP | 06350119 A | 12/1994 |
| JP | 2645254 B2 | 8/1997 |
| JP | 11075813 A | 3/1999 |
| JP | 2000504924 T | 4/2000 |
| JP | 3061467 B2 | 7/2000 |
| JP | 2001354407 | 12/2001 |
| NO | 921371 A | 6/1992 |
| NO | 981082 A | 5/1998 |
| TW | 519548 B | 2/2003 |
| WO | 9105849 | 5/1991 |
| WO | 9105849 A1 | 5/1991 |
| WO | 9322418 A1 | 11/1993 |
| WO | 9506111 A1 | 3/1995 |
| WO | 9603494 A1 | 2/1996 |
| WO | 9711154 | 3/1997 |
| WO | 9728274 A1 | 8/1997 |
| WO | 9800559 A1 | 1/1998 |
| WO | 9829531 A1 | 7/1998 |
| WO | 0012673 A1 | 3/2000 |
| WO | 0104263 A2 | 1/2001 |
| WO | 0168257 | 9/2001 |
| WO | 0174990 A1 | 10/2001 |
| WO | WO 0315364 | 2/2003 |
| WO | 03038348 A1 | 5/2003 |
| WO | 03067213 A2 | 8/2003 |
| WO | 03094598 | 11/2003 |
| WO | 03094598 A1 | 11/2003 |
| WO | 2004033075 A1 | 4/2004 |
| WO | 2004074423 A2 | 9/2004 |
| WO | 2005006838 A2 | 1/2005 |
| WO | 2005072254 A2 | 8/2005 |
| WO | 2005079650 A1 | 9/2005 |
| WO | 2005101525 A3 | 10/2005 |
| WO | 2006020177 | 2/2006 |
| WO | 2006020177 A | 2/2006 |
| WO | 2007011343 | 1/2007 |
| WO | 2007038605 | 4/2007 |
| WO | 2008008263 | 1/2008 |
| WO | WO 2008008262 | 1/2008 |
| WO | 2008178739 A1 | 7/2008 |
| WO | 2008134010 A2 | 11/2008 |
| ZA | 7500373 A | 8/1976 |

OTHER PUBLICATIONS

Negoro, M; Hamasaki, A; Ikuta, Y; Makita, T; Hirayama, K; and Suzuki, S "Carbon Dioxide Fixation by Microalgae Photosynthesis Using Actual Flue Gas Discharged from a Boiler" Applied Biochemistry and Biotechnology, 1993, 39/40 (1), pp. 643-653.*

Ikuta, Y; Hukuda, Y; Hamasaki, A; Shioji, N; Makita, T; Hirayama, K; Matsuzaki, H;and Tukamoto, T "Carbon Dioxide Fixation by Microalgal Photosynthesis Using Actual Flue Gas Discharged From a Boiler" Abstracts of the National Renewable Energy Laboratory (NREL) Fifteenth Symposium on Biotechnology for Fuels and Chemicals, May 14-15, 1993, 157 pp.*

Johnston, H.W. "The Biological and Economic Importance of Algae. Part 4: The Industrial Culturing of Algae" Tuatara, 22(2), Jun. 1976, 125 pp.*

Lee, C-G and Palsson, B O, "Photoacclimation of *Chlorella vulgaris* to Red Light from Light-Emitting Diodes Leads to Autospore Release Following Each Cellular Division" Biotechnol. Prog. 1996, 12(2), pp. 249-256.*

"Biomass Gasification, Research, Development, and Demonstration at the University of Hawaii," pp. 1-4, Aug. 16, 2001, http://www2.ctahr.hawaii.edu/biosystems/Gasifier/index.htm.

"Gas-busters: Algae comes to the aid of coal-fired plants," CNN.com, pp. 1-3, Jul. 31, 2000, http://www8.cnn.com/2000/NATURE/07/31/algae.carbon.enn.

"Gasification and Pyrolysis of biomass," Summary of TAB working report No. 49, pp. 1-4, printed Nov. 26, 2001, from http://www.tab.fzk.de/en/projekt/zusammenfassung/AB49.htm.

"Local Man runner-up in contest at MIT," The Sun Chronicle, Jun. 2, 2002, 1 page.

"Scientists Look to Cut Greenhouse Emissions," Office of Research Communications, Ohio University, pp. 1-3, Oct. 22, 2001 http://www.ohio.edu/researchnews/Science/co2_plants.htm.

"Scientists Look to Nature to Cut Greenhouse Emissions," Science Daily Magazine, pp. 1-3, Oct. 22, 2001, http://www.sciencedaily.com/releases/2000/07/000720800707.htm.

Antal, Jr., J.J., G. Varhegyi, and E. Jakab (1998) Cellulose Pyrolysis Kinetics: Revisted, Industrial Engineering Chemical Research, vol. 37, pp. 1267-1275.

Antal, Jr., M.J., S.G. Allen, D. Schulman and X. Xu 2000. biomass Gasification in Supercritical Water, Industrial Engineering Chemical Research, vol. 39, pp. 4040-4053.

Badawy, W.A., "Imrpoved n-Si/oxide junctions for environmentally safe solar energy conversion," Solar Energy Materials and Solar Cells, Elsevier Science Publishers, Amsterdam, NL, vol. 71, No. 3, Feb. 15, 2002, pp. 281-294.

Biohydrogen, "Development of Efficient Large-Scale Photogioreactors" James C Ogbonna et al, Chapter 41, "Internal Gas Exchange Photogioreactor" James P Szyper et al, Chapter 53 pp. 329-344 and 441-446, Plenum Press, New York, 1998.

Burlew, John S., Algal Culture, From Laboratory to Pilot Plant, Chapter 9, pp. 105-153; Chapter 11, pp. 166-176; Chapter 17, pp. 235-272; Chapter 18, pp. 273-281, Carnegie Institute of Washington Publication 600, Wahsing, D.C., 1961.

Chao, Kuo-Ping, et al., "Aquacultural characteriscts of *Rhizoclonium riparium* and an evaluation of its biomass growth potential," Journal of Applied Phycology, vol. 17, pp. 67-73, 2005.

Chornet, E., and Czernik S., Renewable Fuels: Harnessing Hydrogen, Nature, vol. 418, pp. 928-929 (2002).

Cortrigh, R. D., R.R. Davda and J.A. Dumesic (2002) "Hydrogen from Catalytic Reforming of Biomass-derived Hydrocarbons in Liquid Water", Nature, vol. 418, 964-967.
Czernik, S., et al., "Hydrogen by Catalytic Steam Reforming of Liquid Byproducts from Biomass Thermoconversion Processes", I&EC Research, vol. 41, pp. 4209-4215 (2002).
Dote, Y. et al., "Recovery of liquid fuel from hydrocarbon-rich microalgae by thermochemical liquefaction," Fuel, 1994, 73:12.
Dote, Y., et al., Recovery of liquid fuel from hydrocarbon-rich microalgae by thermochemical liquefaction, Dec. 16, 1993, 3 pages.
Dwi, S., et al., "Utilization of cyanobacterial biomass from water bloom for bioproduction of lactic acid," World Journal of Microbiology & Biotechnology, 17: 259-264, 2001.
Ginzburg, B., "Liquid Fuel (Oil) From Halophilic Algae: A Renewable Source of Non-Polluting Energy," Renewable Energy, vol. 3, No. 2/3, pp. 249-252, 1993.
Gluz, M.D., et al., Modified Airlift Reactors: The Helical flow Promoters, Chemical Engineering Science, vol. 51, No. 11, pp. 2915-2920, 1996.
Gratzel, M., Molecular Photovoltaics and Mimic Photosynthesis, Pur Appl. Chem, 73:459 (2001).
Gratzel, M., Photoelectrochemical Cells, Nature, 414:338 (2001).
Gray, "Fundamentals of Bitumen Coking Processes Analogous to Granulations: A Critical Review", The Canadian Journal of Chemical Engineering, vol. 80, pp. 393-401, Jun. 2002.
Hamasaki, M., et al., "Influence of CO2, SO2 and NO in flue gas on microalgae productivity," Journal of Chemical Engineering of Japa, 30 (4): 620-624, Aug. 1997, Abstract.
Handbook of Microalgal Culture, Edited by Amost Richmond, "Mass Production of Microalgae: Photobioreactors," Mario R. Tredici, Chapter 9, Blackwell Science, Ltd., Oxford, United Kingdom, 2004, pp. 178-214.
Ike, A., et al., "Hydrogen Photoproduction from CO2-Fixing Microalgal Biomass: Application of Lactic Acid Fermentation by *Lactobacillus amylovorus*," Journal of Fermentaiton and Bioengineering, vol. 84, pp. 428-433 (1997).
Ikuata, Y., et al., "Hydrogen Production by Photosynthetic Microorganisms," In bioHydrogen, Zaborsky et al., eds. Plenum Press, New York, pp. 319-327 (1998).
Kumar, B.S., et al., A y-ray Tomographic Scanner for Imaging of Void Distribution in Two-Phase Flow Systems, Flow Meas. Instrum., 6(3), 61 (1995).
Kumar, et al., Gas Holdup Measurements in Bubble Columns Using Computed Tomography, AIChE J., 43(6), 1414 (1997).
LaMonica, Martin, "Start-up drills for oil in algae," CNET Press Release, pp. 1-4, May 20, 2005, http://www.news.com.
Larachi, et al., A gamma-ray Detection System for 3D Particle Tracking in Multiphase Reactors, Nucl. Instr. & Meth., A338, 568 (1994).
Laskin, I. and Lechevalier, H.A., Editors, CRC Handbook of Microbiology, Cleveland CRC Press, pp. 519-552 (1977).
Lee, Yuan-Kun, "Enclosed bioreactors for the mass cultivation of photosynthetic microorganisms: the future trend," TIBTECH, Jul. 1986, Elsevier Science Publishers B.V., Amsterdam, pp. 186-189.
Liberman, "Studies of the Chemistry of Hydrocarbons and Their Catalytic Conversions", vol. 30, No. 5, pp. 237-251, (1961).
Maness and Weaver "Hydrogen Production From a Carbon-Monoxide Oxidation Pathway in Rubrivivax gelatinosus", International J. Hydrogen Energy, vol. 27, pp. 1407-1411 (2002).
Merchuk, et al., "Comparison of photobioreactors for cultivation of the red microalga *Porphyridium* sp," J Chem Technol Biotechnol, 75:1119-1126 (2000).
Merchuk, J., "Why use air-lift bioreactors?", Tibtech, Mar. 1990, vol. 8, pp. 66-71.
Merchuk, J.C., et al., "Light/Dark Cycles in the Growth of the Red Microalga *Porphyridium* sp.," Biotechnology and Bioengineering, vol. 59, No. 6, Sep. 20, 1998, pp. 705-713.
Miura, Y. et al., "Stimulation of Hydrogen Production in algal Cells Grown Under High CO2 concentration and Low Temperature," Applied Biochemistry and Biotechnology, vol. 39/40, pp. 753-761 (1993).
Morita, et al., "Instruciton of microalgal biomass production for practically high photosynthetic perormance using a photobioreactor," Food and Bioproducts Processing, 79 (C3): 176-183 Sep. 2001.
Nagase, et al., "Improvement of Microalgal NOx Rremoval in Bubble column and Airlift Reactors," Journal of Fermentation and Bioengineerng, vol. 86, No. 4, pp. 421-423, 1998.
Ogbanna, James C., et al., BioHydrogen, "Development of Efficient Large-Scale Photobioreactors," Chapter 41, "Internal Gas Exchange Photobioreactor," James P. Szyper, et al., Chapter 53, pp. 329-344 and 441-446, Plenum Press, New York, 1998.
O'Regan B., et al., A Low Cost High Efficiency Solar Cell Based on Dye-Sensitized Colloidal TiO2 Films, Nature, 353:737, (1991).
Osburn, L., "Hemp for Fuel" Schaffer Library of Drug Policy, pp. 1-3, printed Nov. 26, 2001, from http://www.druglibrary.org/schaffer/hemp/hempfuel.htm.
Oswald, William J., "The Engineering Aspect of Microalgae," CRC Handbook of Microbiology, Edited by I. Laskin and H.A. Lechevalier, Cleveland CRC Press, 1977, pp. 519-552.
Otsuki, Toshi, et al., "Hydrogen Production by a Floating-Type Photobioreactor," BioHydrogen, Chapter 45, Plenum Press, New York, 1998, pp. 369-374.
Pulz, O., "Photobioreactors: production systems for photorophic microorganisms," Appl Microbiol Biotechnol 57:287-293, Aug. 22, 2001.
Rake, M., "A burning issue," Perspectives, Spring and Summer 1999, pp. 1-7.
Richmond, Amos, Handbook of Microalgal Culture, Biotechnology and Applied Phycology, Chapter 8 and Ian S.F. Jones, Chapter 33, pp. 125-177 and 534-544, Blackwell Science Ltd., Oxford, United Kingdom, 2004.
Schlotelburg, C., et al., "Characterization of an Airlift Reactor with Helical Flow Promoters," The Canadian Journal of Chemical Engineering, vol. 77, Oct. 1999, pp. 804-810.
Shimamatsu, H., "Mass production of *Spirulina*, an edible microalga," Hydrobiologia, 512: pp. 39-44, 2004.
Soule, A., "Greenfuel mixes algae, carbon dioxide to create oil," Mass High Tech, The Journal of New England Technology, Dec. 5, 2001, pp. 1-3.
Sterling, B, "Hiding the Garbage," Viridian Note 00270: pp. 1-6.
Sung S., et al., "Biohydrogen Production from Renewable Organic Wastes", US DOE Hydrogen, Fuel Cells & Infrastructure Technologies Program—2003 Annual Merit Review Meeting, May 18-22, 2003, Berkeley CA.
Tredici, Mario R., Handbook of Microalgal Culture, Edited by Amos Richmond, Mass Production of Microalgae: Photobioreactors, Chapter 9, Blackwell Science Ltd., Oxford, United Kingdom, 2004, pp. 178-214.
Trinity-Stevens, A., "Scientist Searches Yellowstone Park for Carbon Dioxide-Eating Microbe," Montana State University Communications Services, pp. 1-2.
Ugwu, C. U., et al., "Design of static mixers for inclined tubular photobioreactors," Journal of Applied Phycology, vol. 15, pp. 217-223, 2003.
Ugwu, C. U., et al., "Improvement of mass transfer characteristics and productivities of inclined tubular photobioreactors by insallationof internal static mixers," Appl Micobiol bioechnol (2002) 58:600-607.
Van Ginkel, S., et al., "Biohydrogen Production as a Function of pH and Substrate Concentration", Environmental Science & Technology, vol. 35, pp. 4726-4730 (2001).
Vunjak-Novakovic, Gordana, et al., "Air-Lift Bioreactors for Algal Growth on Flue Gas: Mathematical Modeling and Pilot-Plant Studies," Ind. Eng. Chem. Res. 2005, vol. 44, pp. 6154-6163.
Vunjak-Novakovic, Gordana, et al., "Microgravity Studies of Cells and Tissues," Ann. N.Y. Acad. Sci. 974:504-517 (2002).
Watanabe, et al., "Photosynthetic CO2 conversion technologies using a photobioreactor incorporation microalgae—Energy and material balances," Energy Conversion and Management, 37 (6-8): 1321-1326 Jun.-Aug. 1996, Abstract.
Wu, Xiaoxi and Merchuk, Jose, C., "A model integrating fluid dynamics in photosynthesis and photoinhibition processes," Chemical Engineering Science, 2001, 56, pp. 3527-3538.
Wu, Xiaoxi, et al., "Stimulation of Algae Growth in a Bench-Scale Bubble column Reactor," Biotechnology and Bioengineering, vol. 80, No. 2, 156-168, Oct. 20, 2002.

Xiaoxi Wu, et al., Measurement of fluid flow in the downcomer of an internal loop airlift reactor using an optical trajectory-tracking system, Chemical Engineering Science 58 (2003) 1599-1614.

Xiaoxi, Wu, et al., "Simulation of Algae growth in a bench scale internal loop airlift reactor," Chemical Engineering Science 59 (2004) 2899-2912.

Yuan-Kun Lee, "Enclosed Bioreactors for the mass cultivation of photosynthetic microorganisms: the future trend," TIBTECH, Jul. 1986, Elsevier Science Publishers B.V., Amsterdam, pp. 186-189.

Zimmerman, J., "Algae emissions reduction concept shows new promise,", Electric Light & Power/Utility Automation and Engineering T&D News, printed Apr. 19, 2005, pp. 1-3.

AU2005274791 Response to Examination Report of Feb. 15, 2011, pp. 1-3, filed Aug. 5, 2011.

AU2005274791 Notice of Acceptance, issued Oct. 28, 2011, 12 pages.

AU2007273128 First Examination Report, issued May 2, 2011, 3 pages.

IN 1137/DELNP/2007 First Examination Report, Oct. 19, 2012, 3 pages.

AU 2005274791 Examination Report, Feb. 11, 2011, 3 pages.

AU 2005274791 Applicants' response to Examination Report, Aug. 5, 2011, 3 pages.

* cited by examiner

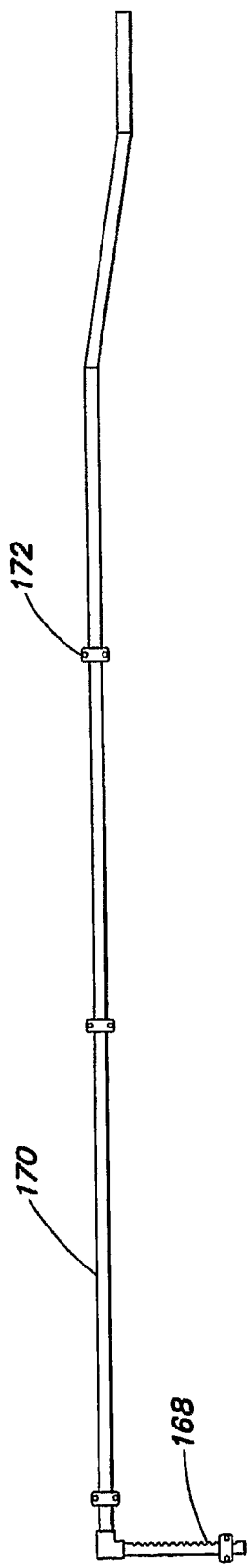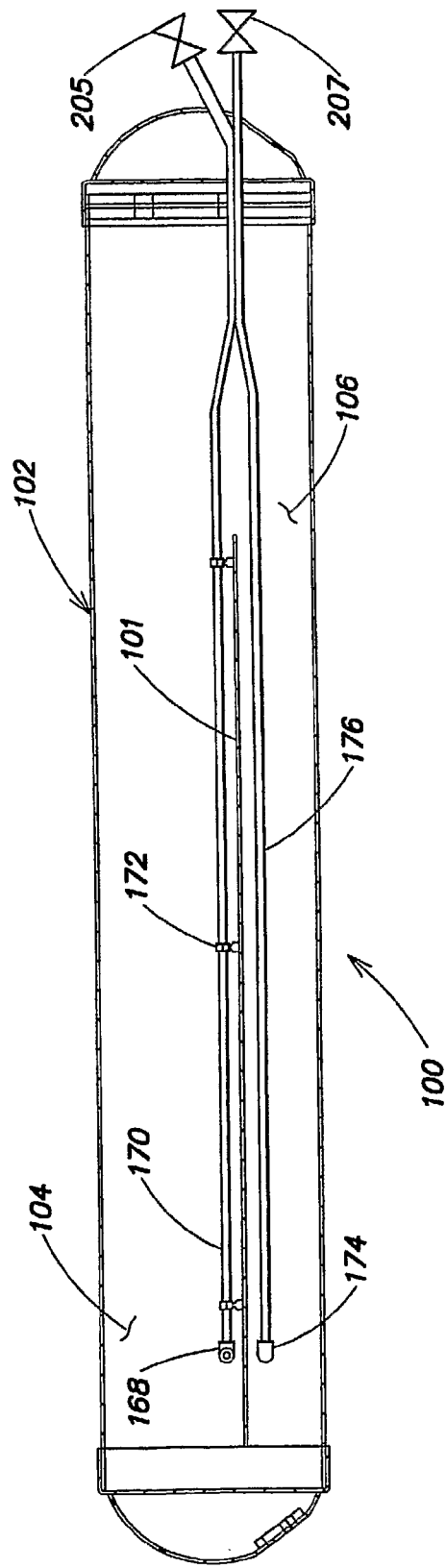

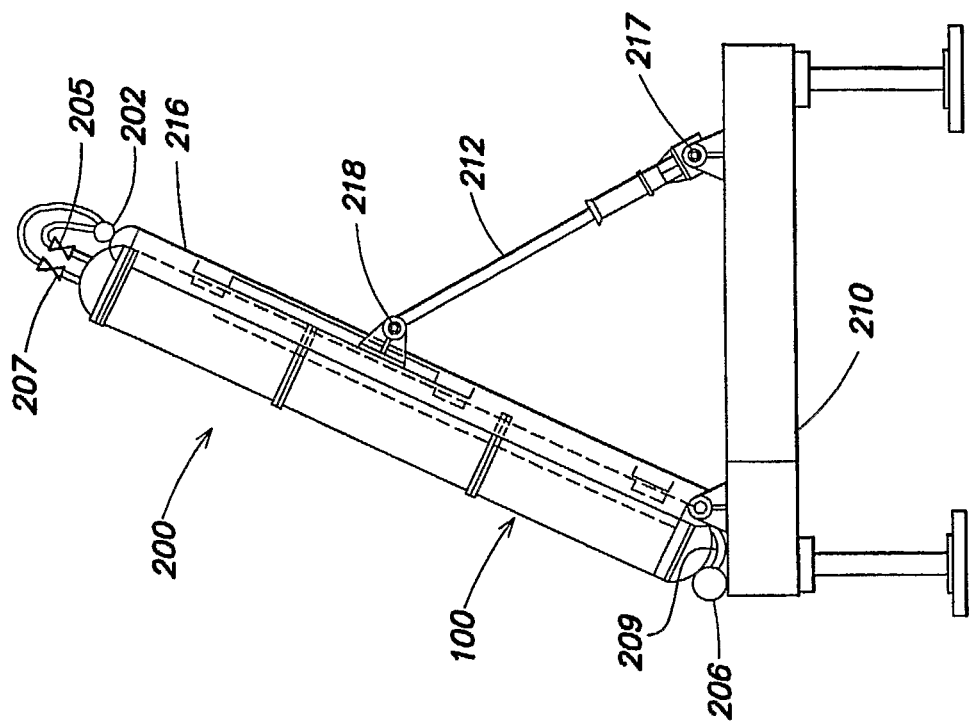
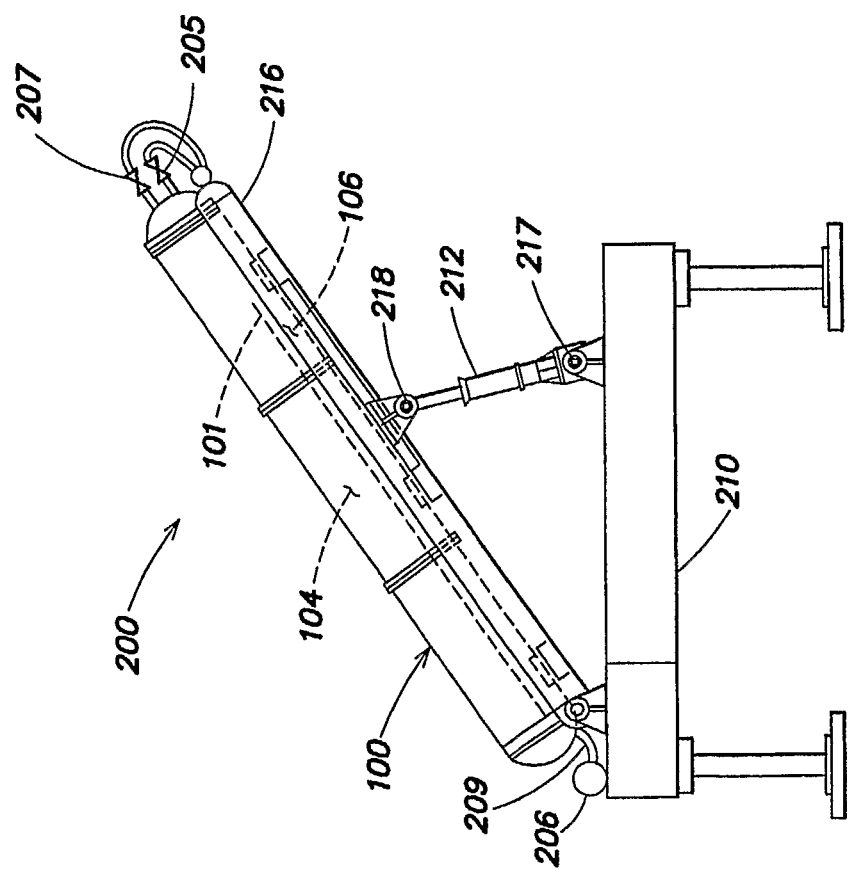
FIG. 3A
FIG. 3B

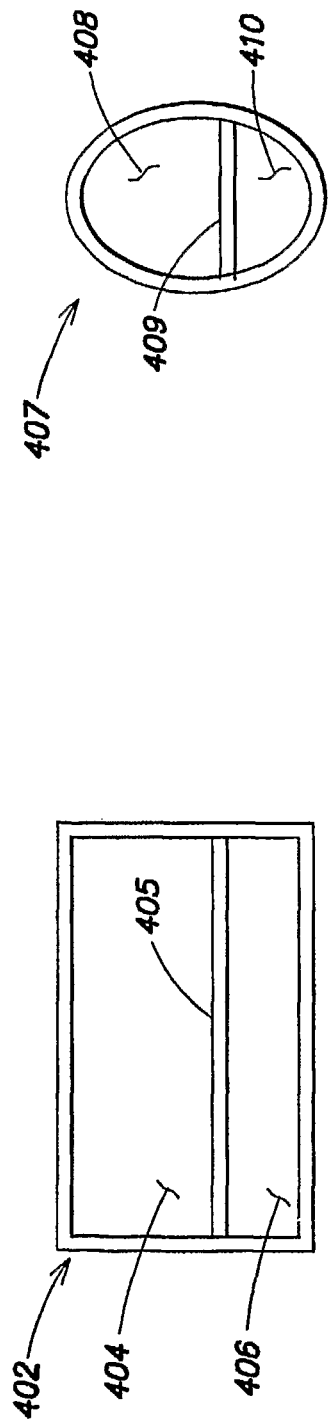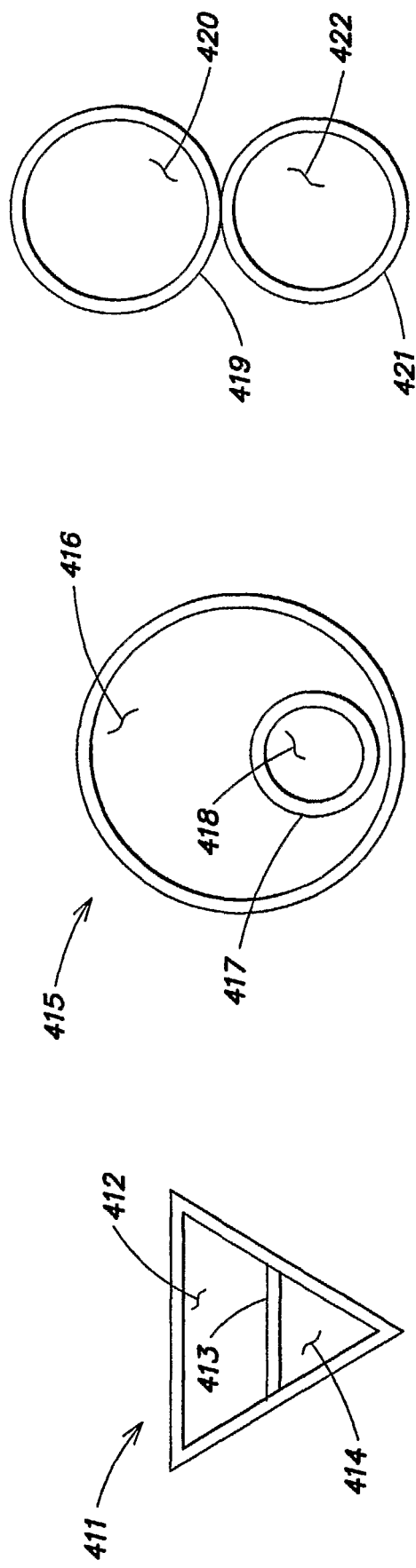

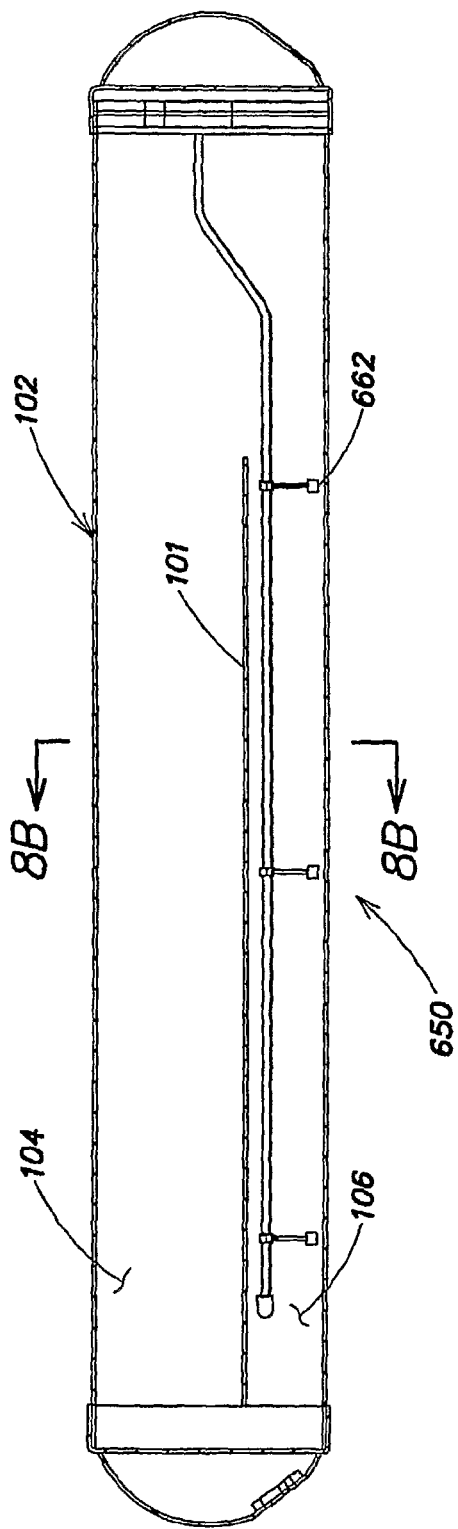
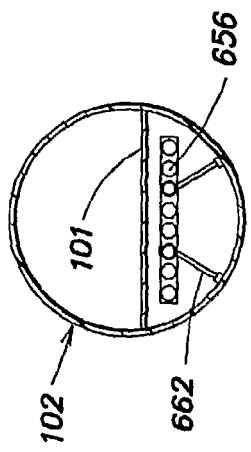
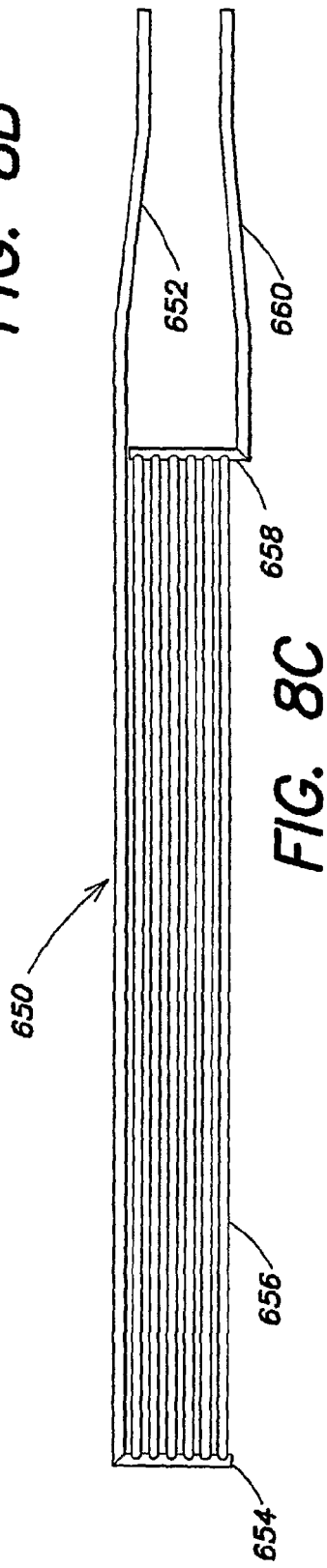
FIG. 8A
FIG. 8B
FIG. 8C

PHOTOBIOREACTOR CELL CULTURE SYSTEMS, METHODS FOR PRECONDITIONING PHOTOSYNTHETIC ORGANISMS, AND CULTURES OF PHOTOSYNTHETIC ORGANISMS PRODUCED THEREBY

RELATED APPLICATIONS

This application is a continuation-in-part of U.S. patent application Ser. No. 11/106,695, now pending, filed Apr. 14, 2005, which claims the benefit of priority under Title 35, U.S.C. §119(e) of U.S. provisional application Ser. No. 60/562,057, filed Apr. 14, 2004, and which is a continuation-in-part of U.S. patent application Ser. No. 10/924,742, filed Aug. 23, 2004, now pending, which claims the benefit of priority under Title 35, U.S.C. §119(e) of U.S. provisional application Ser. No. 60/497,445, filed, Aug. 22, 2003, and which is a continuation-in-part of PCT International Application No. PCT/US03/15364 filed May 13, 2003, which was published under PCT Article 21(2) in English, which entered the U.S. national phase under 35 U.S.C. §371 and was assigned U.S. patent application Ser. No. 10/514,224, and which claims the benefit of priority via PCT/US03/15364 under Title 35, U.S.C. §119(e) of U.S. provisional application Ser. No. 60/380,179, filed May 13, 2002.

This non-provisional application claims the benefit of priority under Title 35, U.S.C. §119(e) of U.S. provisional application Ser. No. 60/589,527, filed, Jul. 16, 2004. Each of the above-referenced applications and publication is incorporated herein by reference.

FIELD OF INVENTION

The invention relates generally to cell culture systems and processes to operate and use such cell culture systems for the culture and adaptation of microorganisms.

BACKGROUND OF THE INVENTION

In the United States alone, there are 400 coal burning power plants representing 1,600 generating units and another 10,000 fossil fuel plants. Although coal plants are the dirtiest of the fossil fuel users, oil and gas plants also produce flue gas (combustion gases) that may include $CO_2$, $NO_X$, $SO_X$, mercury, mercury-containing compounds, particulates and other pollutant materials.

Photosynthesis is the carbon recycling mechanism of the biosphere. In this process, photosynthetic organisms, such as plants, synthesize carbohydrates and other cellular materials by $CO_2$ fixation. One of the most efficient converters of $CO_2$ and solar energy to biomass are microalgae, often referred to herein simply as "algae," the fastest growing photoautotrophic organism on earth and one of nature's simplest microorganisms. In fact, over 90% of $CO_2$ fed to algae can be absorbed, mostly through the production of cell mass. (Sheehan John, Dunahay Terri, Benemann John R., Roessler Paul, "A Look Back at the U.S. Department of Energy's Aquatic Species Program: Biodiesel from Algae," 1998, NERL/TP-580-24190; hereinafter "Sheehan et al. 1998"). In addition, algae are capable of growing in saline waters that are unsuitable for agriculture.

Using algal biotechnology, $CO_2$ bio-regeneration can be advantageous due to the production of useful, high-value products from waste $CO_2$. Production of algal biomass during combustion gas treatment for $CO_2$ reduction is an attractive concept because dry algae has a heating value roughly equivalent to coal. Algal biomass can also be turned into a high quality liquid fuel which is similar to crude oil or diesel fuel ("biodiesel") through thermochemical conversion by known technologies. Algal biomass can also be used for gasification to produce highly flammable organic fuel gases suitable for use in gas-burning power plants. (e.g., see Reed T. B. and Gaur S. "A Survey of Biomass Gasification" NREL, 2001; hereinafter "Reed and Gaur 2001").

Approximately 40 kilocalories (167 kJ) of free energy are stored in plant biomass for every mole of $CO_2$ fixed during photosynthesis. Algae are responsible for about one-third of the net photosynthetic activity worldwide. Photosynthesis can be simply represented by the equation:

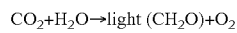

$$CO_2 + H_2O \xrightarrow{light} (CH_2O) + O_2$$

where ($CH_2O$) represents a generalized chemical formula for carbonaceous biomass.

Although photosynthesis is fundamental to the conversion of solar radiation into stored biomass, efficiencies can be limited by the limited wavelength range of light energy capable of driving photosynthesis (400-700 nm, which is only about half of the total solar energy). Other factors, such as respiration requirements (during dark periods), efficiency of absorbing sunlight and other growth conditions can affect photosynthetic efficiencies in algal bioreactors. The net result is an overall photosynthetic efficiency that can range from 6% in the field (for open pond-type reactors) to 24% in the most efficient lab scale photobioreactors.

Algal cultures also can be used for biological $NO_x$ removal from combustion gases. (Nagase Hiroyasu, Ken-Ichi Yoshihara, Kaoru Eguchi, Yoshiko Yokota, Rie Matsui, Kazumasa Hirata and Kazuhisa Miyamoto, "Characteristics of Biological $NO_X$ Removal from Flue Gas in a *Dunaliella tertiolecta* Culture System," Journal of Fermentation and Bioengineering, 83, 1997; hereinafter "Hiroyasu et al. 1997"). Some algae species can remove $NO_x$ at a wide range of $NO_x$ concentrations and combustion gas flow rates. Nitrous oxide (NO), a major $NO_x$ component, is dissolved in the aqueous phase, after which it is oxidized to $NO_2$ and assimilated by the algal cell. The following equation describes the reaction of dissolved NO with dissolved $O_2$:

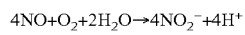

$$4NO + O_2 + 2H_2O \rightarrow 4NO_2^- + 4H^+$$

The dissolved $NO_2$ is then used by the algal as a nitrogen source and is partially converted into gaseous $N_2$. The dissolution of NO in the aqueous phase is believed to be the rate-limiting step in this $NO_x$ removal process. This process can be described by the following equation, when k is a temperature-dependent rate constant:

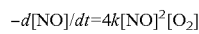

$$-d[NO]/dt = 4k[NO]^2[O_2]$$

For example, $NO_X$ removal using the algae species *Dunaliella* can occur under both light and dark conditions, with an efficiency of $NO_x$ removal of over 96% (under light conditions).

Creating fuels from algal biotechnology has also been proposed. Over an 18-year period, the U.S. Department of Energy (DOE) funded an extensive series of studies to develop renewable transportation fuels from algae (Sheehan et al. 1998). In Japan, government organizations (MITI), in conjunction with private companies, have invested over $250 million into algal biotechnology. Each program took a different approach, but because of various problems addressed by certain embodiments of the present invention, none has been commercially successful to date.

A major obstacle for feasible algal bio-regeneration and pollution abatement has been an efficient, yet cost-effective, growth system. DOE's research focused on growing algae in massive open ponds as big as 4 km². The ponds require low capital input; however, algae grown in open and uncontrolled environments result in low algal productivity. The open pond technology made growing and harvesting the algae prohibitively expensive, since massive amounts of dilute algal waters required very large agitators, pumps and centrifuges. Furthermore, with low algal productivity and large flatland requirements, this approach could, in the best-case scenario, be applicable to only 1% of U.S. power plants. (Sheehan et al. 1998). On the other hand, the MITI approach, with stricter land constraints, focused on very expensive closed algal photobioreactors utilizing fiber optics for light transmission. In these controlled environments, much higher algal productivity was achieved, but the algal growth rates were not high enough to offset the capital costs of the expensive systems utilized.

Typical conventional photobioreactors have taken several forms, such as cylindrical or tubular bioreactors, for example as taught by Yogev et al. in U.S. Pat. No. 5,958,761. These bioreactors, when oriented horizontally, typically require additional energy to provide mixing (e.g., pumps), thus adding significant capital and operational expense. In this orientation, the $O_2$ produced by photosynthesis can become trapped in the system, thus causing a reduction in algal proliferation. Other known photobioreactors are oriented vertically and agitated pneumatically. Many such photobioreactors operate as "bubble columns," as discussed below. Some known photobioreactor designs rely on artificial lighting, e.g. fluorescent lamps, (such as described by Kodo et al. in U.S. Pat. No. 6,083,740). Photobioreactors that do not utilize solar energy but instead rely solely on artificial light sources can require enormous energy input.

Many conventional photobioreactors comprise cylindrical algal photobioreactors that can be categorized as either "bubble columns" or "air lift reactors." Bubble columns are typically translucent large diameter containers filled with algae suspended in liquid medium, in which gases are bubbled at the bottom of the container. Since no precisely defined flow lines are reproducibly formed, it can be difficult to control the mixing properties of the system which can lead to low mass transfer coefficients, poor photomodulation, and low productivity. Air lift reactors typically consist of vertically oriented concentric tubular containers, in which the gases are bubbled at the bottom of the inner tube. The pressure gradient created at the bottom of this tube creates an annular liquid flow (upwards through the inner tube and downwards between the tubes). The external tube is made out of translucent material, while the inner tube is usually opaque. Therefore, the algae are exposed to light while passing between the tubes, and to darkness while passing in the inner tube. The light-dark cycle is determined by the geometrical design of the reactor (height, tube diameters) and by operational parameters (e.g., gas flow rate). Air lift reactors can have higher mass transfer coefficients and algal productivity when compared to bubble columns. However, control over the flow patterns within an air lift reactor to achieve a desired level of mixing and photomodulation can still be difficult or impractical. In addition, because of geometric design constraints, during large-scale, outdoor algal production, both types of cylindrical-photobioreactors can suffer from low productivity, due to factors related to light reflection and auto-shading effects (in which one column is shading the other).

Another problem in utilizing conventional algal culture technology and conventional commercially available algal cultures for pollution mitigation on-site in photobioreactors is that commercially available cultures of species suitable for pollutant abatement are typically poorly suited to grow under light and other conditions that the algae will experience in operation. This can lead to a failure of the culture and photobioreactor system and/or to infiltration of the photobioreactor by parasitic organisms better suited to growth under the prevailing conditions, but that are unable or poorly suited to abatement of pollutants, such as $NO_x$ and $SO_x$.

SUMMARY OF THE INVENTION

Certain embodiments and aspects of the present invention relate to photobioreactor cell culture apparatuses, methods for culturing and preconditioning cultures of photosynthetic organisms, such as algae, with the photobioreactor cell culture apparatuses, and preconditioned cultures and strains of photosynthetic organisms, such as algae, that can be produced by practicing the methods. In certain embodiments the photosynthetic organisms are non-recombinant organisms and are not, and have not been, subjected to any genetic modification techniques involving recombinant genetic manipulation or artificially-induced mutagenesis, e.g. chemically-induced mutagenesis—(i.e. "non-natural mutagenesis," e.g. via exposure of the organisms to mutagenic levels of known mutagenic agents, e.g. ethidium bromide, nitrosoguanadine, etc., and/or levels of radiation, e.g. UV radiation, substantially exceeding levels to which the photosynthetic organisms would be exposed via exposure to natural radiation sources, e.g. natural sunlight, etc.).

In a first set of embodiments, methods are disclosed. In one embodiment a method is disclosed that comprises: exposing a liquid medium comprising at least one species of photosynthetic organisms therein to a defined set of growth conditions that are selected to simulate conditions to which the photosynthetic organisms will subsequently be exposed in a photobioreactor, thereby preconditioning the photosynthetic organisms to the defined set of growth conditions; harvesting photosynthetic organisms preconditioned in the exposing step; and inoculating a photobioreactor with at least a portion of the harvested photosynthetic organisms.

In another embodiment, a method for facilitating the operation of a photobioreactor system is disclosed that comprises: providing at least one species of photosynthetic organisms that has been preconditioned by exposure to a defined set of growth conditions that are selected to simulate conditions to which the photosynthetic organisms will subsequently be exposed in a photobioreactor system during its operation.

In another embodiment, a method of operating a photobioreactor apparatus is disclosed that comprises: inoculating the photobioreactor apparatus with at least one species of photosynthetic organisms that has been preconditioned by exposure to a defined set of growth conditions; and operating the photobioreactor apparatus under conditions substantially similar to the defined set of growth conditions.

In another set of embodiments, preconditioned cultures of at least one species of photosynthetic organisms are disclosed. In certain embodiments, a preconditioned culture of at least one species of photosynthetic organisms is disclosed that is produced by a method comprising acts of: exposing a culture of at least one species of photosynthetic organisms to at least one set of defined growth conditions that comprises exposure of the at least one species of photosynthetic organisms to a source of light capable of driving photosynthesis incident upon at least a portion of the photosynthetic organisms at an intensity at least that capable of causing a reduction in the growth rate of an unadapted sample of the culture via photoinhibition, and variation of the intensity of the light to cause photomodulation at a light/dark cycling frequency of at least one light/dark transition per minute; and forming the preconditioned culture by adapting the at least one species of photosynthetic organisms to the defined growth conditions so that the preconditioned culture is able to grow at the defined growth conditions with a doubling time that is no greater than 50% that of an unadapted sample of the culture subjected to the same defined growth conditions.

In certain such embodiments, the culture is exposed to the defined set of growth conditions that comprises variation of the intensity of the light to cause photomodulation at a light/dark cycling frequency of at least one light/dark transition per 30 seconds, 10 seconds, 5 seconds, 1 second, ½ second, 1/10 second, 1/100 second, or millisecond.

In certain such embodiments, the culture is exposed to the defined set of growth conditions that comprises exposure of the at least one species of photosynthetic organisms to a source of light capable of driving photosynthesis incident upon at least a portion of the photosynthetic organisms at an intensity at least twice or 10 times that capable of causing a reduction in the growth rate of an unadapted sample of the culture via photoinhibition.

In certain such embodiments, the culture is exposed to the defined set of growth conditions that comprises growing the at least one species of photosynthetic organisms in a liquid medium that has been equilibrated with a gas comprising at least one of $CO_2$, $NO_x$, $SO_x$, and/or Hg at about 25 degrees C. and atmospheric pressure at sea level. In some cases, the gas comprises flue gas or a gas mixture simulating flue gas. In some cases, the gas comprises at least about 5 wt % $CO_2$. In some cases, the gas comprises between about 8 wt % $CO_2$-15 wt % $CO_2$. In some cases, the gas comprises at least about 1 ppm $NO_x$. In some cases, the gas comprises at least about 10 ppm $NO_x$. In some cases, the gas comprises at least about 100 ppm $NO_x$. In some cases, the gas comprises between about 100 ppm and about 500 ppm $NO_x$. In some cases, the gas comprises at least about 1 ppm $SO_x$. In some cases, the gas comprises at least about 50 ppm $SO_x$. In some cases, the gas comprises between about 50 and about 1000 ppm $SO_x$. In some cases, the gas comprises at least about 1000 ppm $SO_x$.

In certain such embodiments, the preconditioned culture is formed by adapting the at least one species of photosynthetic organisms to the defined growth conditions so that the preconditioned culture is able to grow at the defined growth conditions with a doubling time that is no greater than 33% that of an unadapted sample of the culture subjected to the same defined growth conditions.

In certain such embodiments, the preconditioned culture comprises at least one species of algae, such as, for example, one or more species of *Chlorella, Spirolina, Chlamydomonas, Dunaliella, Chaetoceros*, and/or *Porphyridum*, such as, for example, at least one of *Dunaliella tertiolecta, Porphyridium* sp., *Dunaliella parva, Chlorella pyrenoidosa, Chliamydomonas reinhardtii*, and/or *Chaetoceros muelleri*.

In certain embodiments, a culture of at least one species of photosynthetic organisms preconditioned to a defined set of growth conditions and having the ability to grow with a doubling time that is no greater than 50% that of an equivalent but non-preconditioned culture subjected to the same defined growth conditions, is disclosed wherein the defined growth conditions comprise: exposure of the at least one species of photosynthetic organisms to a source of light capable of driving photosynthesis incident upon at least a portion of the photosynthetic organisms at an intensity at least that capable of causing a reduction in the growth rate via photoinhibition of the equivalent but non-preconditioned culture; and variation of the intensity of the light to cause photomodulation at a light/dark cycling frequency of at least one light/dark transition per minute.

In certain such embodiments, the defined growth conditions can further comprise: growing the at least one species of photosynthetic organisms in a liquid medium that has been equilibrated with a gas comprising at least one of $CO_2$, $NO_x$, $SO_x$, and/or Hg at about 25 degrees C. and atmospheric pressure at sea level, for example, a gas comprising flue gas or a gas mixture simulating flue gas, and/or comprising between about 8 wt % $CO_2$-15 wt % $CO_2$, and/or comprising between about 100 ppm and about 500 ppm $NO_x$, and/or between about 50 ppm and about 1000 ppm $SO_x$.

In certain such embodiments, the preconditioned culture is able to grow at the defined growth conditions with a doubling time that is no greater than 33% that of an equivalent but non-preconditioned culture subjected to the same defined growth conditions. In certain such embodiments, the preconditioned culture comprises at least one species of algae, such as, for example, one or more species of *Chlorella, Spirolina, Chlamydomonas, Dunaliella, Chaetoceros*, and/or *Porphyridum*, such as, for example, at least one of *Dunaliella tertiolecta, Porphyridium* sp., *Dunaliellaparva, Chlorella pyrenoidosa, Chaetoceros muelleri*, and/or *Chliamydomonas reinhardtii*.

In another set of embodiments, a cell culture system is disclosed. in one embodiment, the cell culture system comprises: at least one cell culture chamber; a source of artificial light capable of driving photosynthesis configured and positioned to direct light to an inner volume of the cell culture chamber; and a light source modulator that is constructed and arranged to vary the intensity of the artificial light between a first intensity to a second intensity at a frequency of at least one variation per second.

BRIEF DESCRIPTION OF THE DRAWINGS

Other advantages, novel features, and uses of the invention will become more apparent from the following detailed description of non-limiting embodiments of the invention when considered in conjunction with the accompanying drawings, which are schematic and which are not intended to be drawn to scale. In the figures, each identical, or substantially similar component that is illustrated in various figures is typically represented by a single numeral or notation. For purposes of clarity, not every component is labeled in every figure, nor is every component of each embodiment of the invention shown where illustration is not necessary to allow those of ordinary skill in the art to understand the invention.

In the drawings:

FIG. 2A is a plan view of a gas sparger assembly according to one embodiment of the invention;

FIG. 2B is a side view of a dual gas sparger assembly positioned within a photobioreactor according to one embodiment of the invention;

FIG. 3A is a side view of an array of photobioreactors at a first inclination angle according to one embodiment of the invention;

FIG. 3B is a side view of an array of photobioreactors at a second inclination angle according to one embodiment of the invention;

FIGS. 5A-5E are schematic, cross-sectional views of a variety of photobioreactor configurations;

FIG. 8A is an cross-sectional side view of a heat exchange element positioned within a photobioreactor according to one embodiment of the invention;

FIG. 8B is a cross-sectional top view, taken along line 7B-7B of FIG. 7A, of a heat exchange element positioned within a photobioreactor according to one embodiment of the invention;

FIG. 8C is a plan view of the heat exchange element of the photobioreactor of FIG. 7A;

DETAILED DESCRIPTION OF THE INVENTION

Figures 1A, 1B:
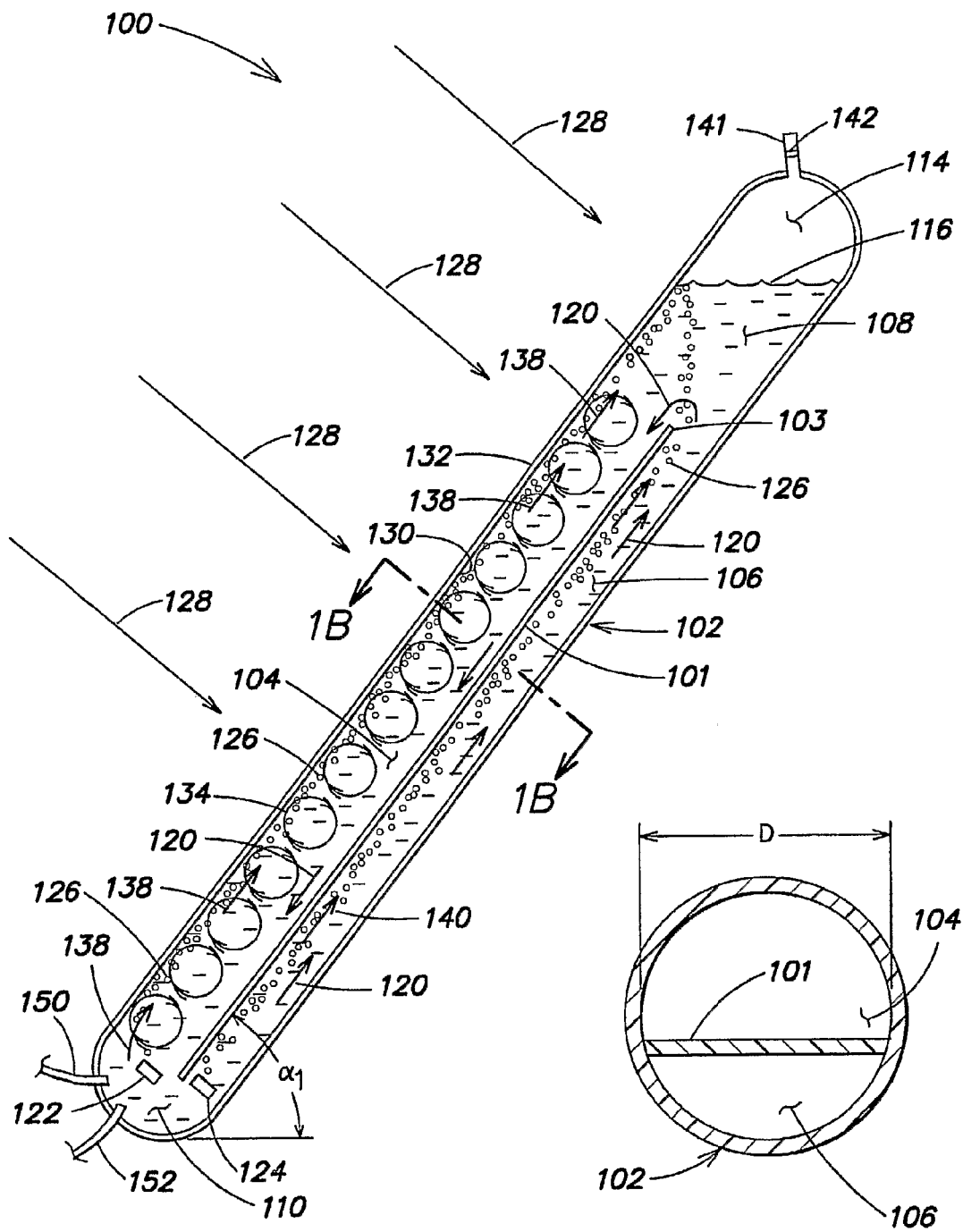
FIG. 1A is a cross-sectional side view of a tubular photobioreactor according to one embodiment of the invention.
FIG. 1B is a cross-sectional top view taken along line 1B-1B of the tubular photobioreactor of FIG. 1A.

Certain embodiments and aspects of the present invention relate to photobioreactor apparatus designed to contain a liquid medium comprising at least one species of photosynthetic organism therein, and to methods of using the photobioreactor apparatus as part of a gas-treatment process and system able to at least partially remove certain undesirable pollutants from a gas stream. In certain embodiments, the disclosed photobioreactor apparatus, methods of using such apparatus, and/or gas treatment systems and methods provided herein can be utilized as part of an integrated method and system for treating waste gasses produced by industrial processes, wherein photosynthetic organisms utilized within the photobioreactor are at least partially remove certain pollutant compounds contained within effluent gases, e.g. $CO_2$ and/or $NO_x$ and are subsequently harvested from the photobioreactor, processed, and utilized as a fuel source for a combustion device (e.g. an electric power plant generator, industrial furnace, and/or incinerator). Such uses of certain embodiments of the invention can provide an efficient means for recycling carbon contained within a combustion fuel (i.e. by converting $CO_2$ in a combustion gas to biomass in a photobioreactor), thereby reducing both $CO_2$ emissions and fossil fuel requirements. The integrated industrial system may include a combustion system, or industrial systems such as fermenters, agricultural waste digesters, catalytic cracking system or pyrolysis/gasification/liquifaction system (e.g. as may be present in many chemical manufacturing facilities, such as oil refineries) or wastewater treatment plants. In certain embodiments, a photobioreactor apparatus can be combined with a supplemental gas treatment apparatus to effect removal of other typical gas contaminants, e.g. as may be present in combustion/flue gas, such as $SO_x$, mercury, mercury-containing compounds, fly ash, heavy metals, ammonia, VOCs, and/or phosphate ash.

In certain embodiments, the photosynthetic organisms that are harvested from a photobioreactor system may be used as a food source for fish or other animals. In certain closed system embodiments, harvested photosynthetic organisms may be used for pharmaceutical purposes.

In certain embodiments a control system and methodology is utilized in the operation of a photobioreactor, which is configured to enable automatic, real-time, optimization and/or adjustment of operating parameters to achieve desired or optimal photomodulation and/or growth rates for a particular environmental operating conditions. In yet another aspect, the invention involves methods and systems for preselecting, adapting, and conditioning one or more species of photosynthetic organisms to specific environmental and/or operating conditions to which the photosynthetic organisms will subsequently be exposed during utilization in a photobioreactor apparatus of a gas treatment system.

Certain aspects of the invention are directed to photobioreactor designs and to methods and systems utilizing photobioreactors. A "photobioreactor," or "photobioreactor apparatus" as used herein, refers to an apparatus containing, or configured to contain, a liquid medium comprising at least one species of photosynthetic organism and having either a source of light capable of driving photosynthesis associated therewith, or having at least one surface at least a portion of which is partially transparent to light of a wavelength capable of driving photosynthesis (i.e. light of a wavelength between about 400-700 nm). Certain photobioreactors for use herein comprise an enclosed bioreactor system, as contrasted with an open bioreactor, such as a pond or other open body of water, open tanks, open channels, etc.

The term "photosynthetic organism" or "biomass," as used herein, includes all organisms capable of photosynthetic growth, such as plant cells and micro-organisms (including algae and euglena) in unicellular or multi-cellular form that are capable of growth in a liquid phase (except that the term "biomass," when appearing in the titles of documents referred to herein or in such references that are incorporated by reference, may be used to more generically to refer to a wider variety of plant and/or animal-derived organic matter). These terms may also include organisms modified artificially or by gene manipulation. While certain photobioreactors disclosed in the context of the present invention are particularly suited for the cultivation of algae, or photosynthetic bacteria, and while in the discussion below, the features and capabilities of certain embodiments that the inventions are discussed in the context of the utilization of algae as the photosynthetic organisms, it should be understood that, in other embodiments, other photosynthetic organisms may be utilized in place of or in addition to algae. For an embodiment utilizing one or more species of algae, algae of various types, (for example *Chlorella, Chlamdomonas, Chaetoceros, Spirolina, Dunaliella, Porphyridum*, etc) may be cultivated, alone or in various combinations, in the photobioreactor.

The phrases of "at least partially transparent to light" and "configured to transmit light," when used in the context of certain surfaces or components of a photobioreactor, refers to such surface or component being able to allow enough light energy to pass through, for at least some levels of incident light energy exposure, to drive photosynthesis within a photosynthetic organism.

FIGS. 1A and 1B illustrate one exemplary embodiment of a tubular photobioreactor apparatus 100, according to one aspect of the invention. Photobioreactor 100 comprises a conduit 102 that includes a partition 101 which separates conduit 102 into two fluidically interconnected channels 104, 106. In certain embodiments, the partition is substantially continuous and impermeable to liquid along its entire length and width. In certain embodiments, the partition has a length that is at least 20% of the conduit length, in certain embodiments the partition has a length that is at least 85% of the conduit length. In certain embodiments, the partition has a length that is at least less than 85% of the conduit length. In certain embodiments, the partition has a length that is between 80% and 85% of the conduit length. The interconnected channels together provide a flow loop enabling the liquid medium 108 contained with the photobioreactor to flow sequentially from a region of origin (e.g., header 110) within the flow loop, through the two channels, and back to the region of origin. Liquid medium 108 is shown as flowing in a counterclockwise direction in the direction of arrows 120. As discussed in more detail below, liquid medium 108 may, alternatively, flow in a clockwise direction, or be controlled to be substantially stagnant, i.e. not have a bulk flow for any desirable period of time. While in the illustrated embodiment the tubular photobioreactor includes two channels 104 and 106, in other embodiments, the photobioreactor can include multiple partitions and/or conduits providing three or more channels and/or can be arranged having a geometry other than a single straight conduit as illustrated in FIGS. 1A and 1B (e.g. two parallel, fluidically interconnected conduits, such as illustrated in FIG. 5E). Also, while in the illustrated embodiment, the volume of the channel 104 is different from the volume of the channel 106, in other embodiments, the partition may essentially bisect the conduit along the length of the partition to form a first channel and a second channel, such that the first channel and the second channel have essentially equal volumes.

The term "fluidically interconnected", when used in the context of conduits, channels, chambers, or other structures provided according to the invention that are able to contain and/or transport gas and/or liquid, refers to such conduits, channels, containers, or other structures being of unitary construction or connected together, either directly or indirectly, so as to provide a continuous coherent flow path from one conduit or channel, etc. to the other(s) to which they are fluidically interconnected. In this context, two conduits or channels, etc. can be "fluidically interconnected" if there is, or can be established, liquid and/or gas flow through and between the conduits and/or channels (i.e. two conduits/channels are "fluidically interconnected" even if there exists a valve between the two conduits/channels that can be closed, when desired, to impede fluid flow therebetween).

A "channel" as used herein, refers to a passage or lumen through which a liquid or other fluid can flow. A channel may comprise, in certain embodiments, fluid impermeable wall(s) for completely surrounding a fluid passing through the channel along its direction of flow. In other embodiments, wall(s) of a channel may only partially surround a fluid passing through the channel along its direction of flow and/or the wall(s) may have some degree of permeability with respect to a fluid flowing in the channel, so long as the wall(s) sufficiently surround the fluid and are fluid impermeable to a sufficient extent so as to be able to establish and maintain a bulk flow direction of fluid generally along a trajectory parallel to a longitudinal axis or curve defining the geometric center of the channel along its length. In some cases, a channel may comprise the lumen of a conduit. In other cases, the lumen of a conduit may include therein one or more partitions dividing the lumen into two or more channels. A "conduit" as used herein refers to a pipe, tube, duct, or the like having a lumen through which a liquid or other fluid can flow, which pipe, tube, duct, or the like comprises a structure that is physically distinct from other conduits, in that more than a single wall thickness separates fluid contained in the conduit from the fluid contained in any other conduit. As mentioned above, in certain cases, the lumen of a conduit may comprise a single channel. In other cases, the lumen of a conduit may comprise one or more partitions therein which divide it into two or more channels.

As discussed in greater detail below, the liquid medium contained within the photobioreactor during operation typically comprises water or a saline solution (e.g. sea water or brackish water) containing sufficient nutrients to facilitate viability and growth of algae and/or other photosynthetic organisms contained within the liquid medium. As discussed below, it is often advantageous to utilize a liquid medium comprising brackish water, sea water, or other non-portable water obtained from a locality in which the photobioreactor will be operated and from which the algae contained therein was derived or is adapted to. Particular liquid medium compositions, nutrients, etc. required or suitable for use in maintaining a growing algae or other photosynthetic organism culture are well known in the art. Potentially, a wide variety of liquid media can be utilized in various forms for various embodiments of the present invention, as would be understood by those of ordinary skill in the art. Potentially appropriate liquid medium components and nutrients are, for example, discussed in detail in: Rogers, L. J. and Gallon J. R. "Biochemistry of the Algae and Cyanobacteria," Clarendon Press Oxford, 1988; Burlew, John S. "Algal Culture: From Laboratory to Pilot Plant." Carnegie Institution of Washington Publication 600. Washington, D.C., 1961 (hereinafter "Burlew 1961"); and Round, F. E. The Biology of the Algae. St Martin's Press, New York, 1965; each incorporated herein by reference).

Photobioreactor 100, during operation, is filled with enough liquid medium 108 so that the fill level 116 is above a top 103 of partition 101, so as to permit a recirculating loop flow of liquid medium (e.g., in the direction of arrows 120) during operation. In some embodiments, some portion, e.g. approximately 20%, of the volume of photobioreactor 100 is left unfilled with liquid medium. As is explained in more detail below, in certain embodiments, liquid flow inducing elements may be used to control the liquid flow direction and/or stop or reverse the liquid flow direction from the counterclockwise direction illustrated. In certain embodiments, the liquid flow inducing elements may also inject gas into the channels. In the illustrated embodiment, as described in more detail below, photobioreactor 100 employs a feed gas introducing mechanism and liquid medium flow-inducing mechanism comprising two gas spargers 122 and 124, which are configured to create a plurality of bubbles 126 rising up and through channels 104 and 106, thereby inducing liquid flow.

In certain embodiments, photobioreactor apparatus 100, is configured to be used in conjunction with a source of natural light, e.g. sunlight 128. In such an embodiment, at least one of channels 104 and 106 should be at least partially transparent to light of a wavelength capable of driving photosynthesis. In the illustrated embodiment, conduit 102 comprises a "solar panel" surface 132 that is at least partially transparent to sunlight 128. The partial transparency of conduit 102 may permit sunlight 128 to penetrate a distance into conduit 102, but leave portions of conduit substantially unilluminated, thereby providing "dark tubes" or dark regions within a tube. In certain embodiments, partition 101 is not transparent, resulting in channel 106 being a dark tube.

Conduit 102 may be constructed from a wide variety of transparent or translucent materials that are suitable for use in constructing a bioreactor. Some examples include, but are not limited to, a variety of transparent or translucent polymeric materials, such as polyethylenes, polypropylenes, polyethylene terephthalates, polyacrylates, polyvinylchlorides, polystyrenes, polycarbonates, etc. Alternatively, conduit 102 can be formed from glass or resin-supported fiberglass. Preferably, conduit 102, is sufficiently rigid to be self-supporting and to withstand typical expected forces experienced during operation without collapse or substantial deformation. Portions of conduit may be non-transparent in certain embodiments, and such portions can be made out of similar materials as described above for the at least partially transparent portions of conduit 102, except that, when they are desired to be non-transparent, such materials should be opaque or coated with a light-blocking material. For example, the rear portion of conduit 102 that forms channel 106 may be constructed from an opaque material, along with partition 101, while the front portion of conduit 102 that forms channel 104 may be constructed from a transparent material. As will be explained in more detail below, an important consideration in designing certain photobioreactors according to the invention is to provide a desirable level of photomodulation (i.e. temporal pattern of alternating periods of exposure of the photosynthetic organisms to light at an intensity sufficient to drive photosynthesis and to dark or light at an intensity insufficient to drive photosynthesis) within the photobioreactor. By using materials which do not allow light to penetrate the entire conduit 102, or by making at least a portion of at least one of the conduits non-transparent, dark intervals may be built into the flow loop and can help establish a desirable ratio of light/dark exposure of the algae in the photobioreactor leading to improved growth and performance.

While conduit 102 and channels 104 and 106 as illustrated, comprise straight, linear segments, in alternative embodiments, one or more of the conduit and/or channels may be arcuate, serpentine, or otherwise non-linear, if desired. While, in certain embodiments, tubular conduit 102 and/or channels 104, 106 may have a wide variety of cross-sectional shapes, for example, square, rectangular, oval, triangular, etc., as described below with reference to FIGS. 5A-5E, as illustrated, conduit 102 comprises a length of tubing having an essentially circular cross-sectional shape and channels 104 and 106 have a semi-circular cross-sectional shape.

Partition 101 is illustrated in FIG. 1B to be as wide as conduit 102 in a plane of partition 101. In certain embodiments, partition 101 may be less wide than conduit 102 in a plane of the partition. For example, in certain embodiments, partition 101 may be at least 50%, 75%, 90% or 95% of the conduit width.

Additionally, if desired, one or more of channels 104 and 106 (and especially channel 104 which is exposed to more sunlight than channel 106) can have a variety of flow-disrupting and/or mixing-enhancing features therein to increase turbulence and/or gas-liquid interfacial mixing within the channel. This can, for example, lead to improved short-duration "flashing light" photomodulation, as explained in more detail below, and/or to improved diffusional uptake of gas within the liquid medium for embodiments wherein the gas to be treated is injected directly into the photobioreactor (e.g. as illustrated in FIGS. 1A and 1B). Such flow enhancements can comprise, but are not limited to, fins, baffles, or other flow directing elements within channels 104 and/or 106, and/or can comprise providing conduit 102 with a helical twist along its length, etc.

For certain embodiments, especially for embodiments wherein the gas to be treated, such as combustion gas, flue gas, gas from a biological process, etc., gas is injected directly into the photobioreactor at the base of a light-transparent channel (e.g., within header 100 below channel 104), performance of the photobioreactor can, in certain situations, be improved by providing certain geometric and structural relationships, as described below.

As illustrated, gas sparger 122 is configured and positioned within channel 104 to introduce a gas to be treated into a lower end of conduit 102, so as to create a plurality of gas bubbles 126 that rise up and through liquid medium 108 contained within channel 104 along a portion 130 of the inner surface of the conduit that is directly adjacent to that portion 132 of the outer surface of the conduit that most directly faces sunlight 128. This arrangement, in combination with providing certain angles $\alpha_1$ between channels 104 and/or 106 and the horizontal plane can enable sparger 122 to introduce the gas stream into the lower end of channel 104 such that a plurality of bubbles rises up and through the liquid medium inducing a liquid flow within channel 104 characterized by a plurality of recirculation vortices 134 and/or turbulent eddies positioned along the length of channel 104. These recirculation vortices and/or eddies both can increase mixing and/or the residence time of contact between the bubbles and the liquid within channel 104, as well as provide circulation of the algae from light regions near inner surface 130 of conduit 102 to darker regions positioned closer to inner surface 136 of conduit 102, thereby providing a "flashing light" relatively high frequency photomodulation effect that can be very beneficial for the growth and productivity, (i.e. in converting $CO_2$ to biomass). This effect, and inventive means to control and utilize it, is explained in greater detail below in the context of FIGS. 7A, 9A, and 9B. It is believed that a reason why recirculation vortices 134 and/or turbulent eddies can facilitate enhanced photomodulation is that as the as algae grows within the photobioreactor, the optical density of the liquid medium increases, thereby decreasing the effective light penetration depth within the liquid medium, such that regions within channel 104 positioned sufficiently far away from inner surface 130 will be in regions of the tube where the light intensity is insufficient to drive photosynthesis.

Only a schematic representation of spargers 122, 124 is shown in FIG. 1A. One embodiment of an arrangement for positioning spargers 122, 124 in photobioreactor 100 and supplying gas to the spargers is shown in FIGS. 2A and 2B, described in more detail below.

Other advantages of the illustrated arrangement wherein gas sparger 122 and conduit 102 are arranged such that gas bubbles 126 rise along the region of the conduit upon which the light is most directly incident include improved cleaning and thermal buffering. For example, as bubbles 126 rise up and along the inner surface 130 of channel 104 of conduit 102, they serve to effectively scour or scrub the inner surface, thereby reducing build up of algae on the surface and/or removing any algae adhered to the surface. In addition, because the bubbles can also be effective at reflecting at least a portion of the light incident upon conduit 102, the bubbles can act to effect a degree of thermal buffering of the liquid medium in the photobioreactor. In some embodiments, to enhance the scrubbing and/or thermal buffering effect of the bubbles, a plurality of neutrally buoyant, optionally transparent or translucent, microspheres (e.g. having a diameter of between 0.5 to about 3 mm) could also be utilized. Such buoyant particles would be carried with the liquid flow within conduit 102, thereby creating an additional scrubbing and/or thermal buffering effect, and/or an additional "flashing light" photomodulation effect.

The term "recirculation vortices" as used herein, refers to relatively stable liquid recirculation patterns (i.e. vortices 134) that are superimposed upon the bulk liquid flow direction (e.g. 120). Such recirculation vortices are distinguishable from typical turbulent eddies characterizing fully developed turbulent flow, in that recirculation vortices potentially can be present even where the flow in the conduit is not fully turbulent. In addition, turbulent eddies are typically relatively randomly positioned and chaotically formed and of, for a particular eddy, short-term duration. As will be explained below, the selection of geometries and liquid and/or gas flow rates within the photobioreactors to create such recirculation vortices and/or turbulent eddies can be determined using routine fluid dynamic calculations and simulations available to those of ordinary skill in the art.

In certain other embodiments, as illustrated, the inventive photobioreactor includes multiple gas spargers, e.g. two gas spargers 122 and 124, each of which may be configured and positioned within the photobioreactor to inject gas bubbles at the base of an upwardly-directed channel, such as channel 104 and channel 106. In certain embodiments using direct gas injection into the photobioreactor, a single gas sparger or diffuser (e.g., sparger 122) can be utilized. As will be appreciated by those skilled in the art, the gas bubble stream released from sparger 122 and rising through channel 104 and the gas bubble stream released from sparger 124 and rising through channel 106 (in the direction of arrows 138 and 140, respectively), each provide a driving force having a tendency to create a direction of liquid flow around the flow loop that is oppositely directed from that created by the other. Accordingly, by controlling the overall flow rate of a gas to be treated by the photobioreactor and the relative ratio or distribution of the overall flow rate that is directed to sparger 122 and to sparger 124, it is possible to induce a wide variety of pressure differentials within the photobioreactor, which are governed by differences in gas holdups in channel 104 and channel 106, so as to drive a bulk flow of the liquid medium either counterclockwise, clockwise, or, with the proper balance between the relative gas injection rates, to induce no bulk liquid flow whatsoever around the flow loop.

In short, the liquid medium fluid dynamics are governed by the ratio of gas flow rates injected into spargers 122 and 124. For example, if all of the gas flow injected into the photobioreactor were injected into one of the spargers, this would create a maximal overall liquid flow rate around the flow loop. On the other hand, there is a certain ratio of distribution that, as mentioned above, would result in a stagnant liquid phase. Thus, the relative bulk liquid flow, the gas-liquid residence time in each of channels 104 and 106, as well as the establishment of particular liquid flow patterns within the photobioreactor (e.g., recirculation vortices) can be reproducibly controlled via control of the combination of the overall gas flow rate and the relative ratio of the overall gas flow rate injected into each of spargers 122 and 124.

This arrangement can provide a much greater range of flexibility in controlling overall liquid flow rates and liquid flow patterns for a given overall gas flow rate and can enable changes in liquid flow rates and flow patterns within the photobioreactor to be effected without, necessarily, a need to change the overall gas flow rate into the photobioreactor.

Accordingly, as discussed in more detail below in FIG. 7A, control of the gas injection rates into the spargers of such a two-sparger photobioreactor, as illustrated, can facilitate control and management of fluid dynamics within the photobioreactor on two levels, without the need for supplemental liquid recirculation means, such as pumps, etc., thereby enabling control and optimization of photomodulation (i.e. maintaining maximal continuous algae proliferation and growth via controlled light/dark cycling). These two levels of fluid dynamic control enabling photomodulation control comprise: (1) control of the overall liquid flow rate around the flow loop, which controls the relative duration and frequency that the algae is exposed to light in channel 104 and dark in channel 106; and (2) creation and control of rotational vortices and/or turbulent eddies in solar panel channel 104, in which the algae are subjected to higher frequency variations of light-dark exposure creating, for example, a "flashing light" effect. The liquid flow rate within such a photobioreactor can be adjusted to give a wide range of retention time of the algae within each channel 104 and 106 (e.g., in a range of seconds to minutes).

An additional advantage of the two-sparger gas injection embodiment illustrated, is that in one of the channels in which gas is injected, the relative direction of the gas flow with respect to the direction of bulk liquid flow will be opposite that in the other channel into which gas is injected. In other words, as illustrated in FIG. 1A, gas flow direction 140 in channel 106 is co-current with the direction of liquid flow 120, while gas flow direction 138 in channel 104 is counter-current to bulk liquid flow direction 120. Importantly, by providing at least one conduit in which the direction of gas flow is counter-current to the direction of liquid flow, it may be possible to substantially increase the effective rate of mass transfer between the pollutant components of the gas to be injected, (e.g., $CO_2$, $NO_x$), and the liquid medium.

This can be especially important in the context of $NO_x$ removal in the photobioreactor. It has been shown that in bubble column and airlift photobioreactors utilized for $NO_x$ removal, a counter-flow-type airlift reactor can have as much as a three times higher $NO_x$ removal ability than a reactor in which gas and liquid flow are co-current (Nagase, Hiroyasu, Kaoru Eguchi, Ken-Ichi Yoshihara, Kazumasa Hirata, and Kazuhisa Miyamoto. "Improvement of Microalgal $NO_x$ Removal in Bubble Column and Airlift Reactors." Journal of Fermentation and Bioengineering, Vol. 86, No. 4, 421-423.

1998; hereinafter "Hiroyasu et al. 1998"). Because this effect is expected to be more important in the context of $NO_x$ removal, where, as mentioned in the background, the rate of uptake and removal is diffusion limited, and since algae can process $NO_x$ under both light and dark conditions (i.e. during both photosynthesis and respiration), it may be possible to obtain a similar advantage in $NO_x$ removal with the photobioreactor even for a situation wherein the direction of liquid flow 120 is opposite to that illustrated in FIG. 1A, i.e. such that the gas and liquid flow in channel 104 is co-current and the gas and liquid flow in channel 106 is counter-current. The chemical formula "$NO_x$", as used herein, refers throughout the present specification to any gaseous compound comprising at least one nitrogen oxide selected from the group consisting of: NO and $NO_2$.

The term "gas sparger" or "sparger," as used herein, refers to any suitable device or mechanism configured to introduce a plurality of small bubbles into a liquid. In certain preferred embodiments, the spargers comprise gas diffusers configured to deliver fine gas bubbles, on the order of about 0.3 mm mean bubble diameter or less, so as to provide maximal gas-to-liquid interfacial area of contact. A variety of suitable gas spargers and diffusers are commercially available and are known to those of ordinary skill in the art, including gas spargers that provide bubbles with uncontrolled diameters.

In the embodiment illustrated in FIGS. 1A-1B, gas to be treated that is injected into photobioreactor 100 through spargers 122 and 124 makes a single pass through the photobioreactor and is released from the photobioreactor through gas outlet 141. In certain embodiments, a filter 142, such as a hydrophobic filter, having a mean pore diameter less than the average diameter of the algae can be provided to prevent algae from being carried out of the bioreactor through gas outlet 141. In this or alternative embodiments, other well known means for reducing foaming within a header 114 and loss of algae through the gas outlet may be employed, as would be apparent to those skilled in the art.

Figure 1C:
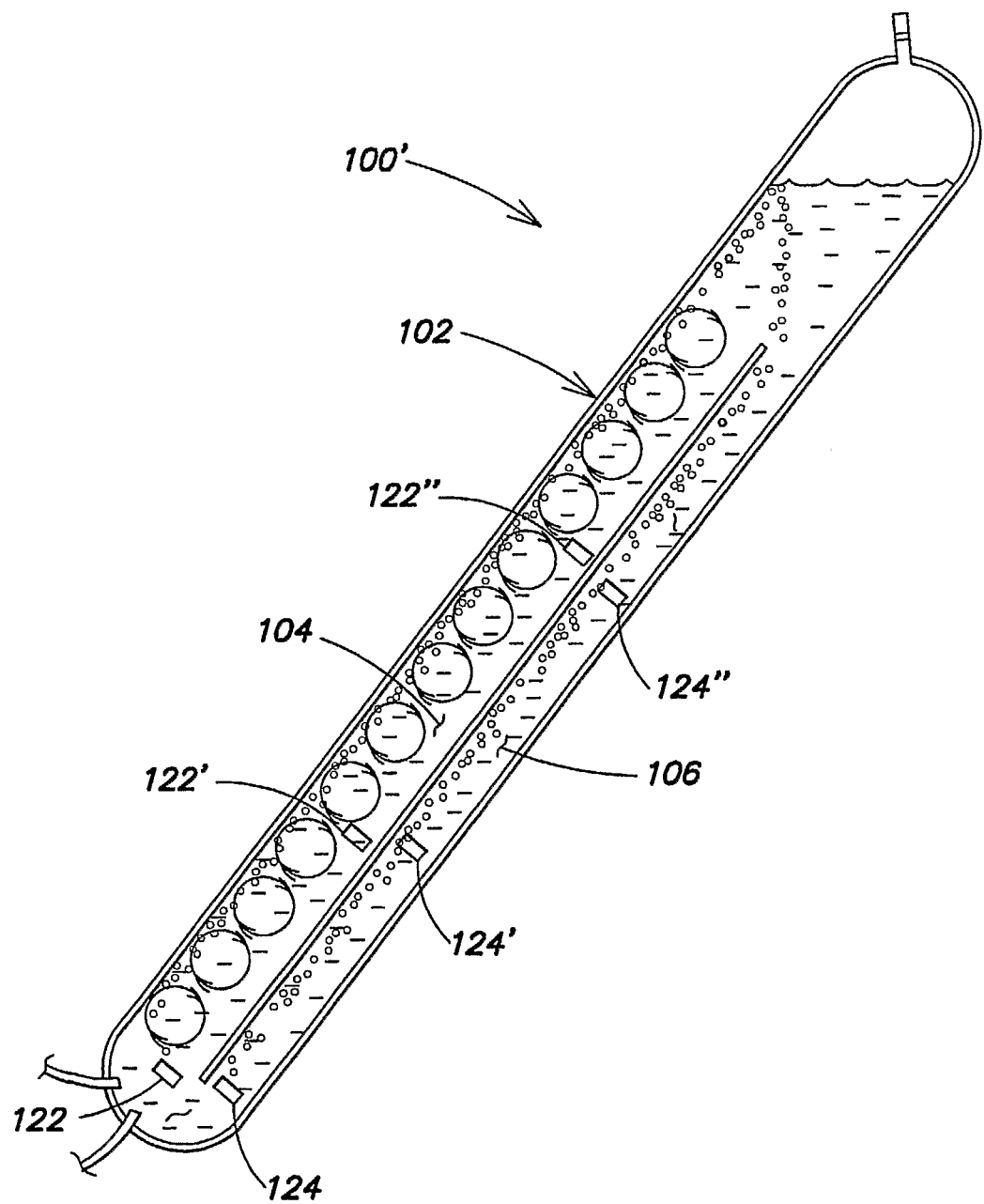
FIG. 1C is a cross-sectional side view of a tubular photobioreactor according to one embodiment of the invention including multiple spargers in each channel positioned at different heights within the photobioreactor conduit.

In certain embodiments, a photobioreactor apparatus of the invention can include multiple spargers within each of one or more channels positioned at different positions along the length of the conduit(s) forming the photobioreactor. For example, a photobioreactor could include a first gas sparger configured and positioned to introduce a gas stream into the conduit at a first longitudinal position (height when inclined) along its length, a second gas sparger configured and positioned to introduce a gas stream into the conduit at a second height, different from the first height. Such an arrangement may be advantageous at reducing gas flow pressure drop and improving liquid recirculation flow rates for very long photobioreactor conduits. Such a configuration is illustrated schematically in FIG. 1C, which shows an embodiment of photobioreactor 100 comprising a conduit 102 in which channel 104 includes three spargers 122, 122', and 122" therein, and in which channel 106, similarly, includes three spargers 124, 124', and 124" therein.

As would be apparent to those skilled in the art, particular configurations of the various conduits and components of the photobioreactor, as well as the particular gas injection rates, liquid recirculation rates, etc. will depend upon the particular use to which the photobioreactor is employed and the composition and quantity of the gas to be treated. Given the guidance provided herein and the knowledge and information available to those skilled in the arts of chemical engineering, biochemical engineering, and bioreactor design, can readily select certain operating parameters appropriate for a particular application, utilizing no more than a level of routine engineering and experimentation entailing no undue burden.

Moreover, as discussed below in the description of FIGS. 3A-3D, and as would be apparent to those skilled in the art, in certain embodiments, photobioreactor 100 can comprise one of a plurality of identical or similar photobioreactors interconnected in parallel, in series, or in a combination of parallel and series configurations so as to, for example, increase the capacity of the system (e.g., for a parallel configuration of multiple photobioreactors) and/or increase the degree of removal of particular components of the gas stream (e.g., for configurations having gas outlets of a photobioreactor in series with the gas inlet of the same and/or a subsequent photobioreactor). In one such embodiment, a photobioreactor system is designed to separate algae species that are efficient in utilizing $NO_x$ from species efficient in utilizing $CO_2$. For example, a nitrogen-efficient algae is placed in a first photobioreactor(s) and carbon-efficient algae is placed in a second photobioreactor(s) in series with the first photobioreactor(s). The flue gas enters the first photobioreactor(s) and is scrubbed of nitrogen (from $NO_x$), then flows through the second photobioreactor(s) and is scrubbed of carbon (from $CO_2$). All such configurations and arrangements of the inventive photobioreactor apparatus provided herein are within the scope of the present invention.

Although photobioreactor 100 was described as being utilized with natural sunlight 128, in alternative embodiments, an artificial light source providing light at a wavelength able to drive photosynthesis may be utilized instead of or in supplement to natural sunlight. For example, a photobioreactor utilizing both sunlight and an artificial light source may be configured to utilize sunlight during the daylight hours and artificial light in the night hours, so as to increase the total amount of time during the day in which the photobioreactor can convert $CO_2$ to biomass through photosynthesis.

Since different types of algae can require different light exposure conditions for optimal growth and proliferation, in certain embodiments, especially those where sensitive algal species are employed, light modification apparatus or devices may be utilized in the construction of the photobioreactors according to the invention. Some algae species either grow much more slowly or die when exposed to ultraviolet light. If the specific algae species being utilized in the photobioreactor is sensitive to ultraviolet light, then, for example, certain portions of external surface 132 of conduit 102, or alternatively, the entire conduit outer and/or inner surface, could be covered with one or more light filters that can reduce transmission of the undesired radiation. Such a light filter can readily be designed to permit entry into the photobioreactor of wavelengths of the light spectrum that the algae need for growth while barring or reducing entry of the harmful portions of the light spectrum. Such optical filter technology is already commercially available for other purposes (e.g., for coatings on car and home windows). A suitable optical filter for this purpose could comprise a transparent polymer film optical filter such as SOLUS™ (manufactured by Corporate Energy, Conshohocken, Pa.). A wide variety of other optical filters and light blocking/filtering mechanisms suitable for use in the above context will be readily apparent to those of ordinary skill in the art. In certain embodiments, especially for photobioreactors utilized in hot climates, as part of a temperature control mechanism (which temperature control strategies and mechanisms are described in much more detail below in the context of FIG. 7A and FIGS. 8A-8C), a light filter comprising an infrared filter could be utilized to reduce heat input into the photobioreactor system, thereby reducing the temperature rise in the liquid medium.

As discussed above, particular configurations and operating parameters yielding desirable or optimal photobioreactor performance will depend on the particular application for which the photobioreactor is utilized and the particular environmental and operating conditions to which it is subjected. While those of ordinary skill in the art can readily, utilizing the teachings in the present specification, the routine level of knowledge and skill in the art, and readily available information, and utilizing no more than a level of routine experimentation that requires no undue burden, select functional configurations, flow rates, materials, etc. for a particular application, certain exemplary and/or preferred parameters are given below and, more specifically, in the examples at the end of the written description of the application, for illustrative, non-limiting purposes.

In certain embodiments, in order to more readily facilitate the formation of recirculation vortices and/or desirable liquid flow patterns, bubble trajectories, etc., a photobioreactor, such as photobioreactor 100 illustrated in FIGS. 1A and 1B, can be configured so that the angle of channel 104 relative to the horizontal differs from the angle of channel 106 relative to the horizontal, e.g. by forming each channel as an independently positionable conduit. In certain embodiments, at least one of the channels forms an angle with respect to the horizontal having an absolute value of less than 90 degrees, in certain embodiments less than or equal to 85 degrees, in certain embodiments less than or equal to 65 degrees. In certain embodiments, at least one of the channels forms an angle with respect to the horizontal having an absolute value of greater than 10 degrees, in certain embodiments at least about 35 degrees. In certain embodiments, at least one of the channels forms an angle with respect to the horizontal having an absolute value of between 10 degrees and less than 90 degrees, between 20 degrees and 85 degrees inclusive, between 35 and 65 degrees inclusive, or in certain embodiments about 45 degrees. In certain embodiments, the angle that falls within the above-mentioned ranges and values comprises the angle between the horizontal and a channel that is transparent to light and in which photosynthesis takes place, (e.g. angle $\alpha_1$ between the horizontal and channel 104).

In certain embodiments, because outer surface 132 of conduit 102 acts as the primary "solar panel" of the photobioreactor, the photobioreactor is positioned, with respect to the position of incident solar radiation 128, such that sunlight is most directly incident upon surface 132, thereby increasing solar uptake and efficiency. As described below with reference to FIGS. 3A-3D, to maintain a desired angle of sunlight incidence, photobioreactor 100 may be used within a system that changes the angle between conduit 102 and the horizontal and/or rotates and/or revolves conduit 102 about an axis of revolution or rotation, e.g. a vertical axis.

The lengths of gas-sparged channels 104 and 106 are selected to be sufficient, for a given desired liquid medium circulation rate, to provide sufficient gas-liquid contact time to provide a desired level of mass transfer between the gas and the liquid medium. Optimal contact time depends upon a variety of factors, especially the algal growth rate and carbon and nitrogen uptake rate as well as feed gas composition and flow rate and liquid medium flow rate. The length of channel 106 should be long enough, when channel 106 is used a dark channel, to provide a desired quantity of dark, rest time for the algae. In certain embodiments, conduit 102 is between about 1.5 ft (~0.5 m) and about 24 ft (~7.3 m) inclusive in length, and in certain embodiments conduit 102 is between about 6 ft (1.8 m) and 12 ft (3.7 m) inclusive in length, although shorter or longer conduit lengths may be used.

The internal diameter or minimum internal cross-sectional dimension of conduit 102 and channels 104 and 106 will depend on a wide variety of desired operating conditions and parameters and should be selected based upon the needs of a particular application. In general, an appropriate inner diameter D (see FIG. 1B) of conduit 102 can depend upon, for example, desired volumetric or production capacity, total gas injection flow rate through spargers 122 and 124, bubble size, dimensions of the gas diffuser, etc. If an inner dimension of channel 104 is too small, bubbles from sparger 122 might coalesce into larger bubbles resulting in a decreased level of mass transfer of $CO_2$, $NO_x$, etc. from the gas into the liquid phase, resulting in decreased efficiency in removing pollutants and/or a decreased level or rate of biomass production.

The inner cross-sectional area and dimensions of channel 106 can depend upon the liquid medium flow rate and desired light-dark exposure intervals. Typically, the cross-sectional area should be chosen so that it is not so large to result in an unduly long residence time of the liquid and algae in conduit 106 such that the algae spends too much time during a given flow loop cycle not exposed to light, thereby leading to a reduction in the solar efficiency of the photobioreactor.

Regarding the cross-sectional sizes of the cross-sectional areas of channels 104 and 106 relative to one another, a wide variety of operating conditions may be involved in choosing appropriate relative sizes, for example, the intensity of solar radiation 128, algal concentration and optical density of the liquid medium, gas flow rate, and the desired mixing and flow pattern properties of the liquid medium within the channels during operation. In certain embodiments, the cross-sectional area of channel 104 may be between approximately 10% and 90% of the total cross-sectional area of channels 104 and 106 combined. In certain preferred embodiments, the cross-sectional area of channel 104 may be 50% or more, 60% or more, or 70% or more of the total cross-sectional area of channels 104 and 106 combined. In certain embodiments, the volumes of each channel 104, 106 may be essentially equal to one another. The cross-sectional area of a conduit refers to the area within the internal walls defining the outer perimeter of lumen of the conduit taken along a cross-section that is substantially perpendicular to the longitudinal direction of the conduit. The cross-sectional area of a channel refers to the cross-sectional area of the lumen within the bounding walls of the channel (e.g., circumscribed by a partition wall and an internal conduit wall as is the case for conduits 104 and 106 as illustrated).

As a specific example, one photobioreactor includes a tubular bioreactor as illustrated in FIGS. 1A and 1B, wherein the conduit has a circular cross-sectional shape and includes a partition 101 running along a substantial length of the conduit. The exemplary bioreactor may be oriented at an angle $\alpha_1$ between about 20 and 85 degrees. Conduit 102, in this example, is approximately 12 ft (3.7 m) in length and approximately 12 inches (0.3 m) in diameter. The total volume of liquid medium in the bioreactor is about two hundred liters, and the mean bubble size from the spargers is about 0.3 mm. Concentration of algae (for example, one or more species of the genera *Dunaliella* or *Chaetoceros*) is maintained at about 0.5-1.5 g (dried weight)/L of liquid medium.

According to one embodiment of the invention, a photobioreactor having a substantially larger diameter than conventionally employed may be used. For example, conduit 102 of photobioreactor 100 may have a diameter of at least 100 cm such that significantly larger quantities of liquid medium may be used within a single photobioreactor 100. With a larger quantity of liquid medium, such a photobioreactor may be better able to maintain conditions favorable for the survival of algae within the photobioreactor when system or process disruptions occur. For example, if heat exchange capabilities were to be lost, the much larger volume of liquid medium could buffer the effects of heat creation. In addition, larger volume photobioreactors may be able to be operated to provide increased biomass production capacity and/or productivity when compared to smaller volume photobioreactors.

Harvesting algae, adjusting algal concentration, and introducing additional liquid medium can be facilitated via liquid medium inlet/outlet lines 150, 152 as explained in more detail below in the context of the inventive control system for operating the photobioreactor illustrated in FIG. 7A. Control of the concentration of algae is important both from the standpoint of maintaining a desirable level of algal growth and proliferation as well as providing desirable levels of photomodulation within conduit 102. As explained below, algae is harvested periodically or continuously to maintain the desired concentration range during operation. According to a preferred method, harvesting takes place in a semi-continuous fashion, meaning that only a portion of the algae is removed from the photobioreactor at a given time. To harvest the algae, sparging is discontinued and the algae are permitted to settle within header 110. Since algae that is denser than the liquid medium will drop to the bottom of the header, gravity can be utilized to harvest the algae; however, flocculants, chemicals that cause algae to clump and settle, may be used, in certain embodiments, to assist in the harvest. Some useful flocculants include clay (e.g. with particle size <2 μm), aluminum sulfate or polyacrylamide. After settling, algae-rich liquid medium may be withdrawn through one or both of lines 150 and 152. In certain embodiments, fresh, algae-free liquid medium may be injected into one of lines 150 and 152, with the other line open, thereby flushing algae-rich medium out of the photobioreactor while simultaneously replenishing the photobioreactor with fresh medium. In certain embodiments, a volume of algae-free fresh liquid medium that is substantially equal to the volume of algae-rich medium withdrawn is added to the photobioreactor before gas sparging is recommenced. As explained below in FIG. 11, the water and nutrients contained in the harvested algae can be extracted and recycled to the liquid medium supply of the photobioreactor. This step may reduce waste and water use of the photobioreactor and the overall system, thereby lowering environmental impact and operational cost.

Certain species of algae tend to float in water. For embodiments of the photobioreactor which use such algae species, the algal harvesting process described above may be modified so that after gas sparging is turned off, a sufficient time is permitted to allow algae to float to the top of the photobioreactor and into header 114. In such an embodiment, a liquid medium outlet/inlet line (not shown) could be provided in header 114 to facilitate removal of the algae-rich liquid medium for harvesting.

In certain embodiments of a photobioreactor apparatus provided according to the invention, fouling of the inner surface of the conduit by algal adherence may be reduced or eliminated and cleaning and regeneration of the inner surfaces of the photobioreactor may be facilitated by coating at least the portion of the inner surfaces with a layer of a biocompatible substance that is a solid at temperatures of normal operation and that has a melting temperature that is less than the melting temperature of the surface onto which it is coated. Such substances may be transparent or translucent such that they do not unduly reduce the transparency of the surface onto which they are coated. Examples of suitable substances can include a variety of waxes and agars. In one variation of such embodiments, a manual or automatic steam sterilization/cleaning procedure may be applied to the photobioreactor after use and prior to a subsequent use. Such a procedure may involve melting and removing the above described coating layer, thereby dislodging any algal residue that adhered thereto. Prior to use, a new coating layer may be applied. This procedure may allow the light transmitting portions of the photobioreactor to remain clean and translucent over an extended period of use and re-use.

One embodiment of a gas sparger assembly which may be used to inject gas into photobioreactor 100 is shown in FIGS. 2A and 2B. A sparging elements 168 and 174 are positioned toward the bottom of photobioreactor 100 in channels 104 and 106, respectively, in an orientation that is generally perpendicular to the longitudinal axis of the photobioreactor and generally parallel to the plane of partition 101. Gas inlets 170 and 176 extend into the photobioreactor from a position at or near the top of photobioreactor 100, where gas inlets 170 and 176 are connected to a gas supply header 202 (see FIGS. 3A-3C) to receive a supply of gas via gas flow distribution control valves 205 and 207, respectively, which can be independently adjusted and/or controlled to provide a desired gas flow to each of spargers 168 and 174. Support legs 172 are attached to the gas inlet that is positioned within channel 104 so that gas inlet 170 and gas sparger 168 are supported on partition 101. Support legs are optional and gas inlets 170, 176 may be constructed of materials and/or shaped such that they are supported only at the entrance to the photobioreactor. In some embodiments, the gas inlets may be supported external to the photobioreactor and the photobioreactor entrance.

Of course, more than two sparging elements may be used with photobioreactor 100. In some embodiments, only one sparger is used. Additionally, one or both of gas inlets 170, 176 may enter photobioreactor 100 at location other than the top of the photobioreactor, for example, one or both of the gas inlets may be positioned to enter at or near the bottom of photobioreactor 100. In certain embodiments, rather that each sparger being supplied via a common gas supply header 202 via an adjustable/controllable valve, each sparger is provided with its own separate, flow controlled gas supply line feeding the photobioreactor.

Reference is now made to FIGS. 2A-2D. FIGS. 2A-2D illustrate an embodiment comprising a plurality of photobioreactors 100*i*-100*ix* arranged in parallel to form a photobioreactor array 200. Parallel array 200 illustrates a distinct advantage of the tubular photobioreactor apparatus provided according to embodiments of the invention, namely that the capacity of the photobioreactor system may be scaled linearly with the number of identical, similar, or differently sized photobioreactor units used. In the embodiment shown in FIGS. 2A-2D, array 200 includes photobioreactors of various sizes, but array 200 may include photobioreactors of only similar or identical sizes, in which case the capacity of the photobioreactor system would scale in direct proportion with the number of photobioreactor unit used.

Figure 3C:
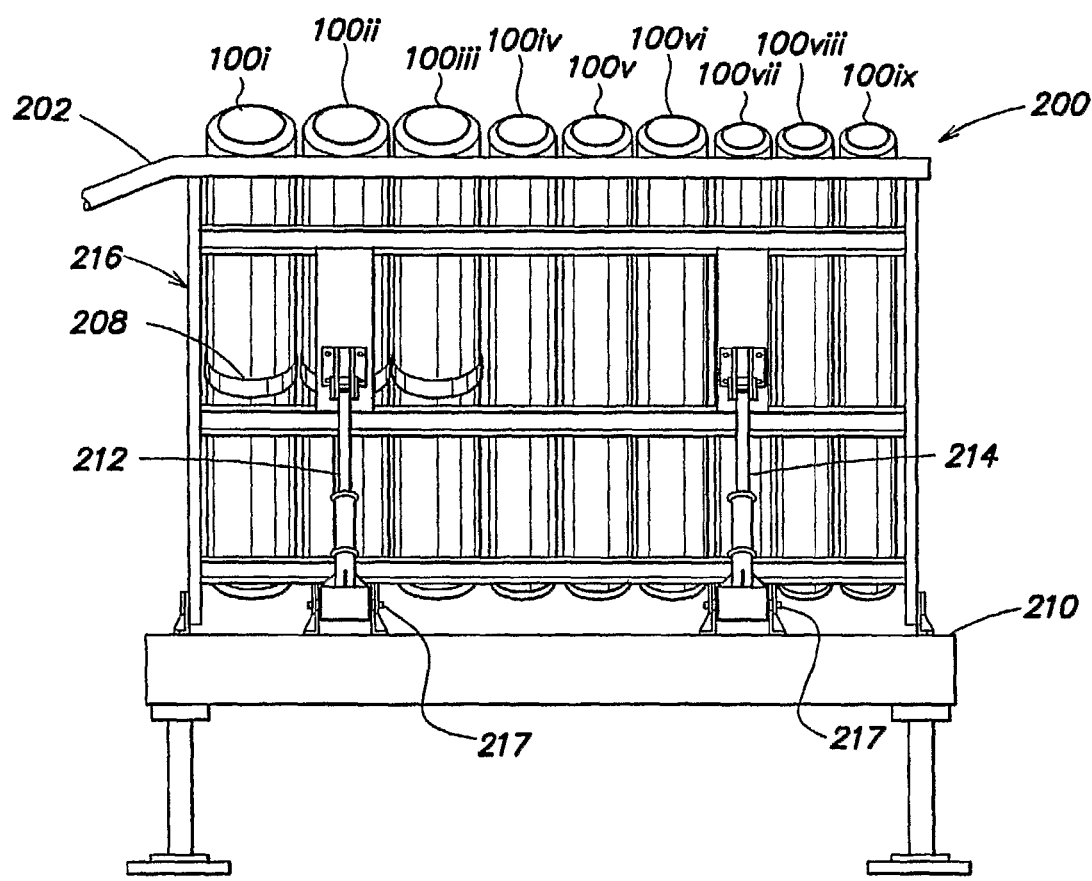
FIG. 3C is a rear elevation view of an array of photobioreactors according to one embodiment of the invention.

Photobioreactor array 200, comprising nine photobioreactor units 100*i*-100*ix*, may share a common gas supply header 202 (not shown in FIG. 3D) and a common liquid medium header 206 (not shown in FIG. 3C). Gas sparger header 202 may be connected to each sparger(s) of each photobioreactor, e.g. two spargers may be used, one for each of the solar channels 104 of each photobioreactor and one for each of the dark channels 106 for each of the photobioreactors. As described above, to facilitate the ability to independently control the gas flow to each of the spargers, flow control valves 205, 207 may be used. Liquid medium header 206 may be connected to each photobioreactor with flexible tubing 209 and may include a valve (not shown) which allows for flow control. Alternatively, in some embodiments, liquid medium header 206 may not comprise a simple conduit-like header, as illustrated, but, rather, may comprise a solid structure providing a plurality of cavities located at the points where the various conduits of the photobioreactors connect to the headers, which cavities facilitate fluid communication between the channels of the individual photobioreactor units, while preventing liquid fluid communication between adjacent photobioreactors.

Figure 3D:
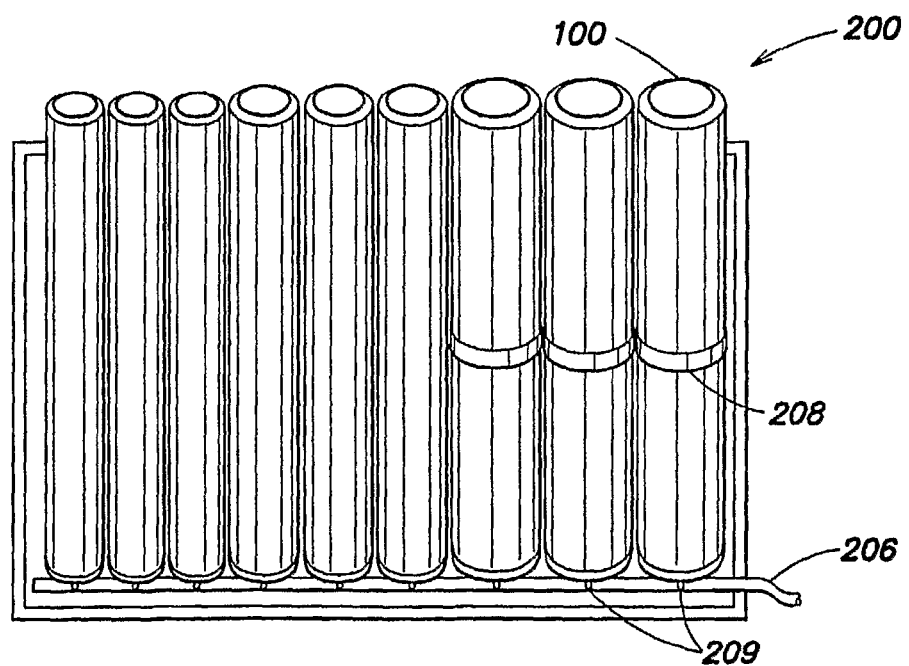
FIG. 3D is an elevation view of an array of photobioreactors according to one embodiment of the invention.

As illustrated in FIGS. 3C and 3D, individual photobioreactor units may have various diameters/cross-sectional areas, for example, a 10 inch (25.4 cm) diameter, a 12 inch (30.5 cm) diameter, or a 14 inch (35.6 cm) diameter. As discussed above, the lengths of individual photobioreactor units may be chosen based on various performance requirements and/or operating conditions. In the illustrated embodiment, the photobioreactor units 100*iv*-100*ix* are approximately nine and a half feet in length and made from a single, extruded conduit, which may be made with a polymeric material (e.g. a polyacrylic material, such as PMMA). Conduits of the photobioreactors may, however, be formed by joining two or more shorter conduit segments together with a connection collar 208, as shown in photobioreactors 100*i*-100*iii* of FIGS. 3C and 3D.

In certain embodiments, as illustrated, photobioreactor array 200 optionally may be supported by a support platform 210. Support platform 210 may be configured to rotate or revolve about a vertical axis (not shown) and/or translate from one location to another such that photobioreactor array 200 can be oriented/positioned toward the sun as it crosses the sky throughout the day. In some embodiments, individual photobioreactor units may be configured to rotate independently from one another.

Support arms 212, 214 are shown in FIG. 3C supporting braces 216 which in turn support the photobioreactor array 200. Support arms 212, 214 may be manually or hydraulically operated telescoping arms in some embodiments with pivot joints 217, 218 at either end of the arms to facilitate changing the angle of the photobioreactor units. In some embodiments, bottom ends of the support arms may be movable relative to support platform 210 to facilitate changing the angle of the photobioreactors relative to horizontal. Changing the angle of the photobioreactors may be performed manually or automatically according to a set of instructions and/or calculations and/or in response to values from various sensors (e.g., temperature sensors or light intensity sensors). Real-time control of the positioning of the photobioreactors may be facilitated as part of the computer-implemented control strategy discussed below in the context of FIG. 7A.

Figure 4:
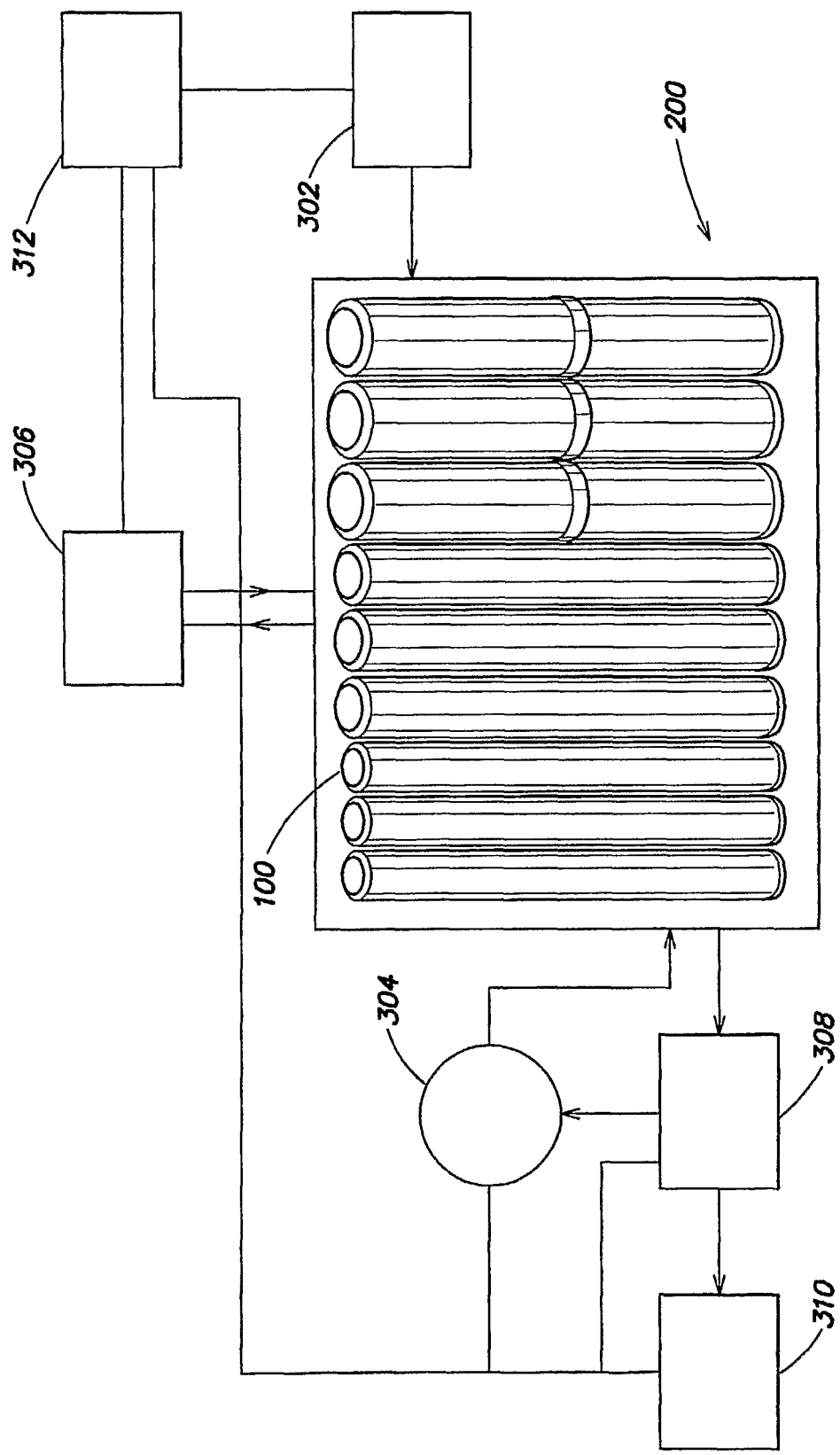
FIG. 4 is a schematic block diagram of a photobioreactor system according to one embodiment of the invention.

Referring now to FIG. 4, an exemplary schematic block diagram of a photobioreactor system including various components external to the photobioreactor array 200 is illustrated. A blower 302 is used to feed gas to the gas spargers or other gas feed mechanisms in the photobioreactor tubes. A medium mixing tank 304 is fluidically interconnected to the photobioreactor tubes to replace medium that is removed during algae harvesting from the tubes. Additional tanks of course may be used as buffer tanks or mixing tanks within the system. A chiller 306 cools a heat exchange fluid, such as water, ethylene glycol solutions, etc., which is pumped through heat exchange elements within the photobioreactors to remove heat from the photobioreactors in some embodiments. Further description of one embodiment of a heat exchange system is provided below with reference to FIGS. 8A-8C.

Regarding algae harvesting operations, a centrifuge 308 may be used to remove water from the liquid medium that is removed from the photobioreactors. The removed liquid, and nutrients contained therein, may optionally be mixed with fresh liquid medium (for example, in medium mixing tank 304) so as to be reused in the photobioreactors. Alternatively, the removed may be processed to isolate therefrom various desirable substances produced by the algae. A dryer (e.g. an oven) 310 may be used to further dry the algae depending on the planned use of the algae. A controller, e.g. computer-implemented system 312, may be used to monitor and control the operation of the various components, including valves, sensors, etc. In addition to automating operation of aspects of the photobioreactor system, use of computer-implemented system 312 may facilitate optimizing or improving the efficiency of the system by determining suitable values for various control parameters.

FIGS. 5A-5E illustrate a variety of alternative shapes and configurations for alternative embodiments of photobioreactor 100. FIG. 5A illustrates a conduit 402 having rectangular configuration, which can have, in an exemplary embodiment, one solar panel channel 404 and one dark channel 406 divided by a partition 405. FIG. 5B illustrates a conduit 407 having an ovoid configuration. In an exemplary embodiment channel 408 may be configured as a solar panel channel which is separated from a dark channel 410 by a partition 409. FIG. 5C illustrates a conduit 411 having a triangular configuration. In this embodiment, a partition 413 forms a solar panel channel 412 and a dark channel 414.

FIG. 5D illustrates a conduit 415 including a tubular partition 417 forming a separate channel 418 within conduit 415 such that an annular channel 416, which would comprise a solar panel channel, is also formed. In some embodiments, instead of entirely enclosing the perimeter of dark channel 418, partition 417 may form a substantially but less than complete perimeter around liquid flowing in dark channel 418.

FIG. 5E illustrates two parallel channels 420 and 422, each of which is formed with a separate conduit 419 and 421. In the illustrated embodiment, channel 420 is a solar panel channel and is slightly larger in diameter than channel 422, which is a dark channel. Channel 422 may be formed with the same or different materials as channel 420. The shape and or size of conduits 419, 421 may be varied and the two conduits (or more) need not have the same shape.

In certain embodiments, the conduit(s) of a photobioreactor may have an inner wall perimeter that remains substantially constant in size along the length of the conduit length. In certain embodiments, the conduit(s) of a photobioreactor may have an inner wall perimeter that remains substantially constant in shape along the length of the conduit length.

In an alternative embodiment which is similar to the embodiment illustrated in FIG. 5E, the two channels 420 and 422 may be formed by coextruding conduits 419 and 421 such that they are formed of one conduit having two channels that share an internal, dividing wall.

As should be evident to one of skill in the art, while many of the partitions illustrated herein are substantially planar, arcuate partitions (such as partition 417) or otherwise non-planar partitions, e.g. a partition which is helically twisted along the length of the conduit, may be used to form channels of a variety of geometric forms in various conduits.

Figure 6A:
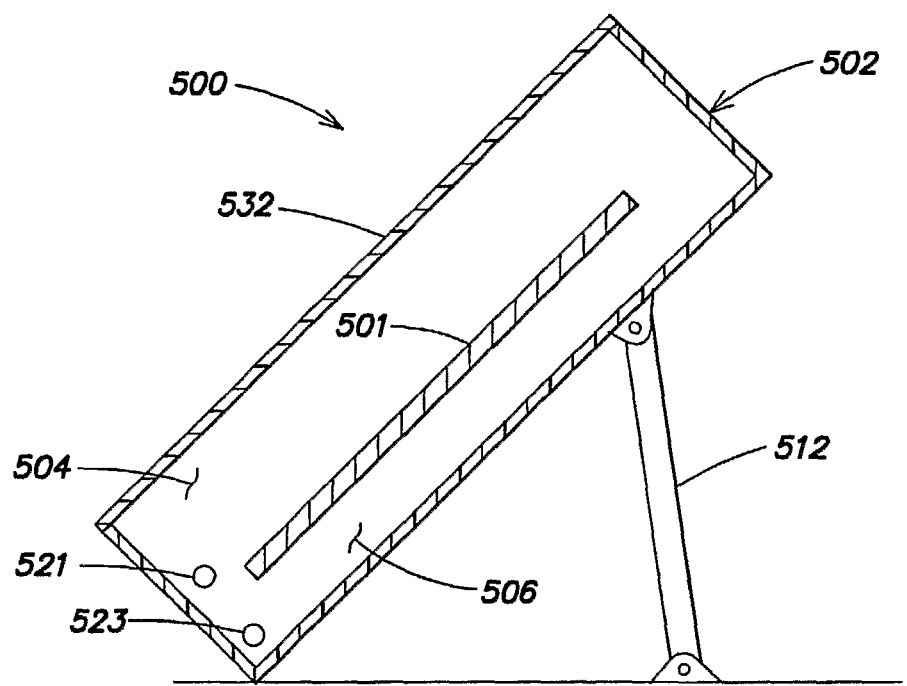
FIG. 6A is a side view of a photobioreactor apparatus according to one embodiment of the invention.
Figure 6B:
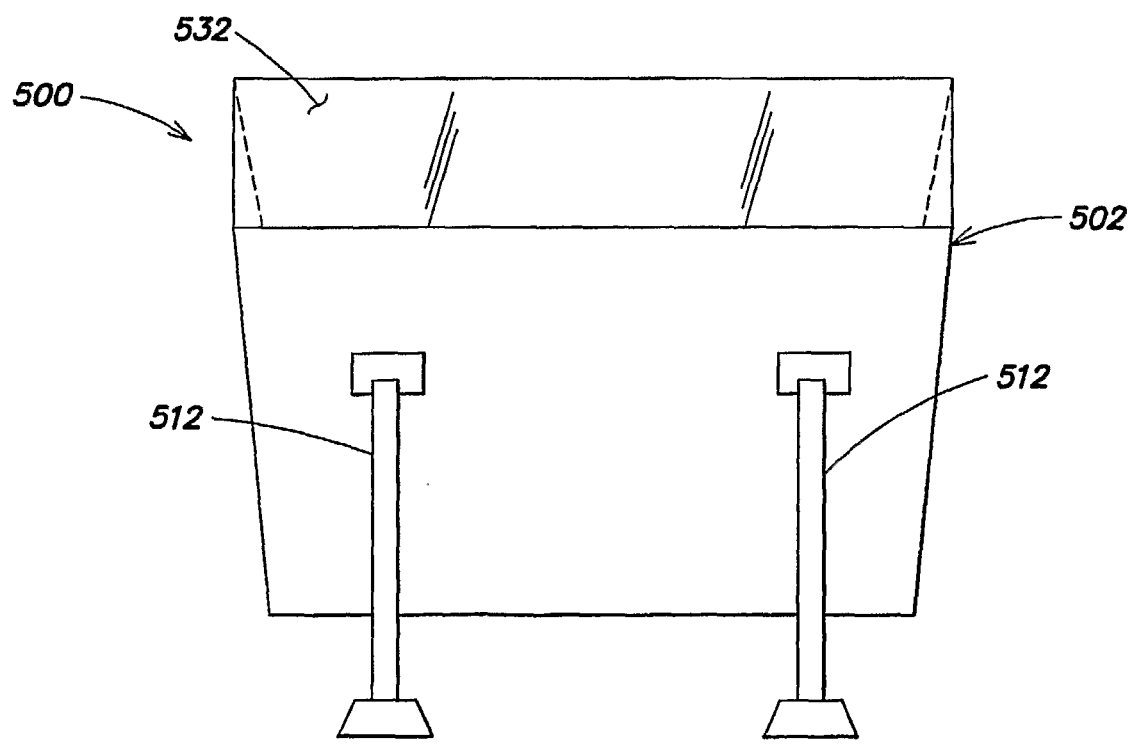
FIG. 6B is a rear elevation view of the photobioreactor apparatus shown in FIG. 5A.

FIGS. 6A and 6B illustrate an alternative embodiment of a photobioreactor apparatus 500, which, when used as part of a photobioreactor system similar to those described above in the context of FIGS. 1A-3 can have similar performance characteristics as previously described for tubular photobioreactor 100 and provide the increased gas scrubbing capacity of parallel photobioreactor array 200, while being constructed as a unitary, integral structure. Photobioreactor apparatus 500 comprises an elongated box-like structure 502 including a solar panel surface 532 that is at least partially transparent to light of a wavelength capable of driving photosynthesis. Photobioreactor apparatus 500 also includes an elongated partition 501 within and spanning the entire or some substantial portion of the width of elongated box-like structure 502. The partition splits elongated box structure 502 into two flow channels 504, 506 which enable recirculating flow of liquid medium 108 within photobioreactor 500, similar to the flow arrangements described above in the context of FIGS. 1A and 1B.

Circulation of liquid medium around the flow loop of photobioreactor apparatus 500 can be facilitated by at least one gas sparger configured to introduce a gas stream into the flow loop of the container. In the illustrated embodiment, gas is introduced into channels 504 and 506 by elongated tubular gas spargers 521 and 523, which extend along the bottom width of bioreactor 500. Similar to the embodiment illustrated in FIGS. 3A-3D, one or more support arms 512 may be used to support apparatus 500 at an angle relative to the horizontal. The dimensions of photobioreactor 500 can be chosen to provide a desired total gas treatment capacity and are typically limited only by the topography/geometry of the site in which the units 500 are to be located and/or limitations in manufacturing, operation and transportation of the units.

In other aspects, the invention provides systems and methods for treating a gas with a photobioreactor including methods for monitoring and controlling liquid flow rates and flow patterns within the photobioreactor to create desired or optimal exposure of the photosynthetic organisms to successive and alternating periods of light and dark exposure to provide a desired or optimal level of photomodulation during operation. It is known that excessive exposure time of algae to light can cause a viability and growth limiting phenomena known as photoinhibition, and that, algal growth and productivity is improved when the algae cells are exposed to both light and dark periods during their growth (i.e. photomodulation). (Burlew 1961; Wu X. and Merchuk J. C. "A model integrating fluid dynamics in photosynthesis and photoinhibition processes," *Chem. Eng. Sci.* 56:3527-3538, 2001 (hereinafter "Wu and Merchuk, 2001," incorporated herein by reference); Merchuk J. C., et al. "Light-dark cycles in the growth of the red microalga *Porphyridium* sp.," *Biotechnology and Bioengineering,* 59:705-713, 1998; Marra, J. "Phytoplankton Photosynthetic Response to Vertical Movement in A Mixed Layer." *Mar. Biol.* 46:203, 1978). As illustrated in FIG. 7A, certain aspects of the present invention provide gas treatment systems comprising one or more photobioreactors and further comprising a control system for controlling and/or monitoring various environmental and performance conditions and/or operating parameters of the photobioreactor, as well as implementing the methods for inducing and controlling photomodulation.

Figures 7A, 7B:
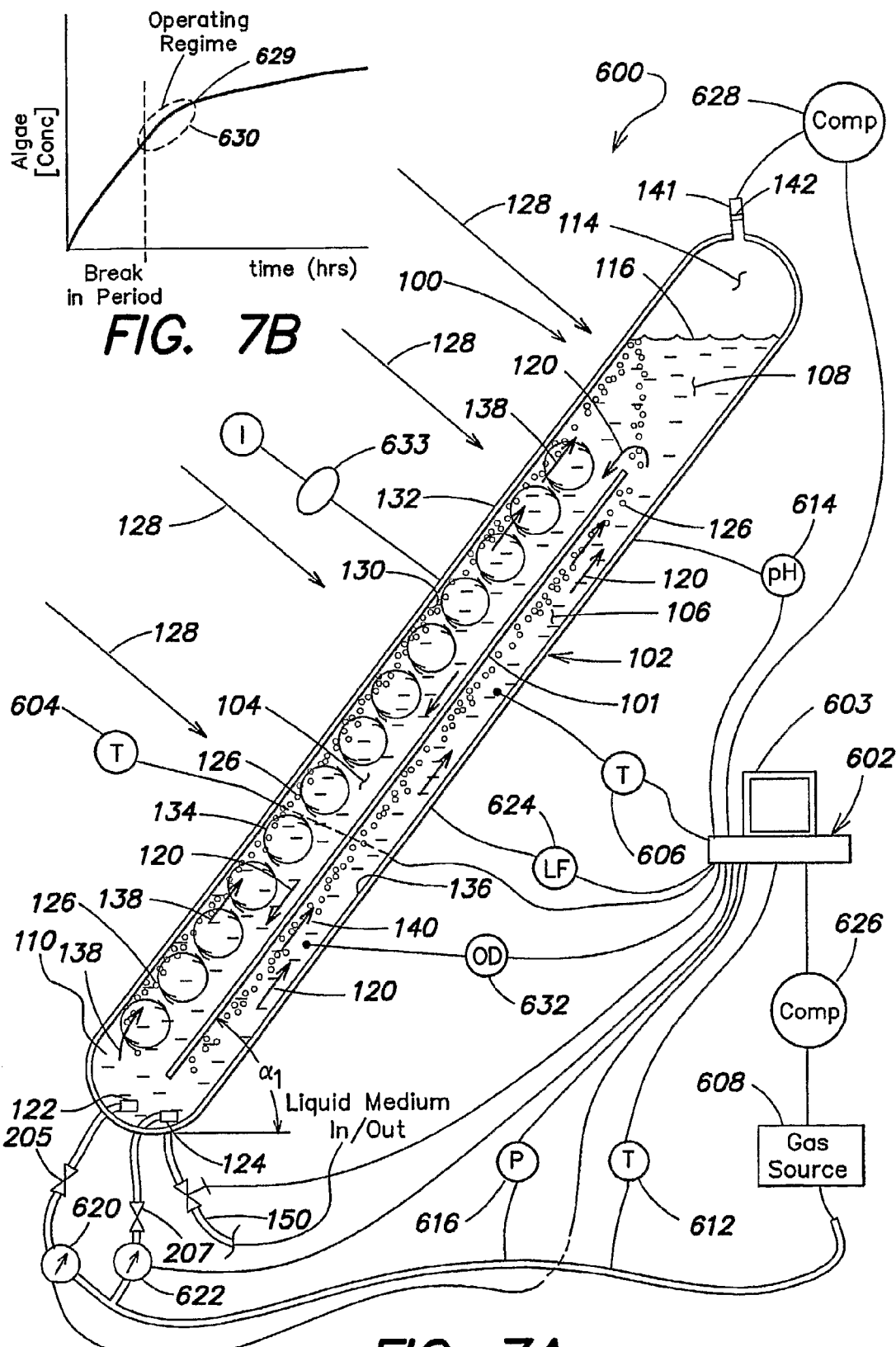
FIG. 7A is a schematic diagram of a photobioreactor system employing the photobioreactor of FIG. 1A and including a computer-implemented control system, according to one embodiment of the invention.
FIG. 7B is a graph illustrating an algae growth curve.

Referring to FIG. 7A, a gas treatment system 600 is shown that includes a photobioreactor 100, a plurality of monitoring and control devices, described in more detail below, and a control system comprising a computer-implemented system 602 that is configured to control various operating parameters as well as to control flow within the photobioreactor to provide desired or optimal levels of light/dark exposure intervals and frequency to yield desired or optimal levels of photomodulation. In certain embodiments, computer-implemented system 602 may be the same as, or a component of, control system 312 described previously in the context of FIG. 4.

In certain embodiments, as discussed in more detail below in the context of the FIGS. 9A and 9B, the computer implemented system 602 is configured to control photomodulation by: performing a simulation of liquid flow patterns within the photobioreactor; and, from the simulation, to calculate exposure intervals of the photosynthetic organisms to light at an intensity sufficient to drive photosynthesis and to dark or light at an intensity insufficient to drive photosynthesis; and to control the flow of the liquid medium within the photobioreactor so as to yield desired or optimal exposure intervals providing a desired or optimal level of photomodulation. Also, as explained in more detail below, desirable or optimal light/dark exposure intervals are, in certain embodiments, also determined by the computer-implemented system utilizing a mathematical model, described in more detail below, of algal growth rate as a function of light/dark exposure intervals.

As used in the above context, an "exposure interval" of a photosynthetic organism to light or dark refers to both length and frequency of exposure to such conditions over a given time period of interest (e.g. a time period required for liquid medium in a tubular flow loop photobioreactor to flow around the entire flow loop). Specifically, as discussed in more detail below, computer implemented system 602, in certain preferred embodiments in calculating "exposure intervals" determines the duration of exposure of the algae, on average, to light intensities both above and below the threshold required to drive photosynthesis as well as the frequency of exposure of the algae to light and dark periods as the algae in the liquid medium is carried around the flow loop of the photobioreactor.

It should be understood that even though this aspect of the present invention is illustrated utilizing photobioreactor 100 for illustrative purposes, in other embodiments, the photomodulation control methodology and control systems described herein could be utilized with other photobioreactors described herein or other conventional photobioreactors. In certain embodiments, photobioreactors of a design similar to photobioreactor 100 are preferred because of the above-described ability of the photobioreactor to create liquid flow in a solar panel channel, such as channel 104, characterized by recirculating vortices 134 and/or turbulent eddies, which can be effective in subjecting the algae within the channel 104 relatively high frequency cycling between areas of the tube in which light intensity will be sufficient to drive photosynthesis (e.g. near surface 132) and other areas of the channel further away from the surface where light intensity may be insufficient to drive photosynthesis.

For example, depending on the relative velocities of the liquid medium flow and gas bubble flow within channel 104, photomodulation frequency (i.e. light to dark interval transition) of greater than 100 cycles per second to less than one cycle per second may be provided. Such a high frequency "flashing light" effect during photosynthetic activity has been found to be very beneficial for growth and productivity of many species of algae (see, Burlew 1961). Moreover, various portions of channel 104 and/or 106, in certain embodiments, may be made either entirely or partially non-transparent to provide additional, more extended exposure of the algae to dark, rest periods, which may be beneficial for productivity as well.

Before describing the photomodulation control methodology and control system of the photobioreactor system 600, various sensors and controls that can be provided in the photobioreactor system will be explained. Control of certain of the physico-chemical conditions within the photobioreactor can be achieved using conventional hardware or software-implemented computer and/or electronic control systems together with a variety of electronic sensors.

For example, it can be important to control liquid medium temperature within photobioreactor 100 during operation to maintain liquid medium temperature within a range suitable or optimal for productivity. These specific, desirable temperature ranges for operation will, of course, depend upon the characteristics of the algae species used within the photobioreactor systems. Typically, it is desirable to maintain the temperature of the liquid medium between about 5 degrees C. and about 45 degrees C., more typically between about 15 degrees C. and about 37 degrees C., and most typically between about 15 degrees C. and about 30 degrees C. For example, a desirable temperature operating condition for a photobioreactor utilizing Chlorella algae may have a liquid medium temperature controlled at about 30 degrees C. during the daytime and about 20 degrees C. during nighttime.

Gas treatment system 600 may control the liquid medium temperature, in certain embodiments, in one or more ways. For example, the temperature of the liquid medium may be controlled via control of the inlet temperature of the gas to be treated fed to spargers 122 and 124 and/or via supplemental cooling systems for directly cooling photobioreactor 100. An exemplary supplemental cooling system is described below with reference to FIGS. 8A-8C. Liquid medium temperature can be monitored in one or more places throughout photobioreactor 100 for example by temperature sensors 604 and 606. Feed gas from gas source 608 fed to sparger 122 and sparger 124 can be temperature monitored via one or more temperature sensors 612. In certain embodiments, feed gas from gas source 608 is passed through a heat exchanger, for example algal drier 912 illustrated in FIG. 11 prior to injection into photobioreactor 100. Depending on the temperature of the liquid medium detected by temperature sensor 604 and 606, the computer-implemented control system 602 can, in certain embodiments, control such a heat exchange system so as to increase or decrease the temperature of the gas fed to spargers 122 and 124 to raise or lower the temperature of the liquid medium.

One exemplary embodiment of a heat exchange element 650 which may be used as part of a heat exchange system is shown in FIGS. 8A-8C. Heat exchange element 650 includes an inlet 652, an inlet manifold 654, a number of heat exchange tubes 656, an outlet manifold 658, and an outlet 660. Inlet 652 and outlet 660 are fluidically interconnected with a source of cooling water or other coolant, e.g. chiller 306 illustrated in FIG. 4. These components may be constructed of any suitable material such as thin-walled stainless steel tubing. Inlet 652 and outlet 660 may enter photobioreactor tube 100 at the top of the conduit 102, as shown in FIGS. 8A and 8B. Inlet 652 and outlet 660 connect to heat exchange tubes 656 which are located within dark channel 106 in the present exemplary embodiment, although, in alternative embodiments, the heat exchange element may be located in solar channel 104 or both channels 104 and 106. Heat exchange element 650 may be supported within conduit 102 by, for example, support legs 662.

As will be evident to one of skill in the art, any suitable heat exchange element or heat exchange system may be used in conjunction with the photobioreactor systems and methods described herein. In some embodiments, no supplemental heat exchange system is required to be present within photobioreactor tubes 100.

As mentioned above, and as explained in more detail below, the demand for cooling and/or heating of the photobioreactor system can be lessened by using an algal strain which has an optimal productivity at temperatures close to actual temperatures to which the algae will be exposed at the operating site. In addition to controlling the liquid medium temperature via modifying the temperature of the feed gas with a heat exchange device, and/or with a supplemental heat exchange element(s) located within the photobioreactor as illustrated in FIGS. 8A-8C and as described above, in other embodiments, especially for embodiments wherein the photobioreactor apparatus is operated in a hot climate, infrared optical filters can be utilized to keep heat energy out of the photobioreactor and/or a supplemental external cooling system, such as a set of external water sprinklers spraying water on the outside of the photobioreactor, could be utilized to lower temperature.

Liquid medium pH can be monitored via pH probe 614. pH can be controlled at desirable levels for a particular species of algae by, for example, providing one or more injection ports, for example in fluid communication with liquid medium inlet/outlet 150, into which pH adjusting chemicals, such as hydrochloric acid and sodium hydroxide, could be controllably injected.

System 600 can also provide various probes and monitors for measuring the pressure of the feed gas fed to the spargers (e.g., one or more pressure monitors 616), as well as one or more flow meters 620, 622 for measuring gas flow rates, and one or more flow meters 624 for measuring bulk liquid flow rate within the photobioreactor flow loop. Gas and liquid flow rates can be controlled, as explained in more detail below, at least in part, to facilitate desired or optimal levels of photo-modulation by inducing desirable liquid flow patterns within the photobioreactor. A second control factor dictating the overall flow of gas fed to photobioreactor 100 can be the desired level of removal of pollutants such as $CO_2$ and/or $NO_x$ by the photobioreactor. For example, as illustrated, system 600 includes appropriate gas composition monitoring devices 626 and 628 for monitoring the concentration of various gases, such as $CO_2$ $NO_x$, $O_2$, etc. in the feed gas and treated gas, respectively. Gas inlet flow rate and/or distribution to the spargers can be adjusted and controlled to yield a desirable level of pollutant removal by the photobioreactor system.

As mentioned above, periodically, in order to keep the concentration of algae within the photobioreactor within a range suitable for long term operation and productivity, at least a portion of the algae may be harvested and the photobioreactor may be supplemented with fresh, algae-free medium (or previously harvested medium having a low algae concentration) to adjust concentration of algae within the photobioreactor. As illustrated in FIG. 7B, under growth conditions, algae concentration (y-axis) will increase exponentially with time (the log growth phase) up to a certain point 629, after which the concentration will tend to level off and proliferation and growth will decrease. In certain preferred embodiments, the concentration of algae within the photobioreactor is maintained within an operating range 630 that is near the upper end of the concentration in which the algae is still in the log growth regime. As would be understood by those by those skilled in the art, the particular growth curve characterizing a given species of algae will be different from species to species and, even within a given a species of algae, may be different depending on differences in operating and environmental factors, (e.g., liquid medium composition, growth temperature, gas feed composition, etc.). As explained in more detail below, in certain embodiments the invention teaches the use of photobioreactor systems using pre-conditioned or pre-adapted algae optimized for growth at the particular operating conditions expected within the photobioreactor gas treatment systems provided according to the invention. In any case, the appropriate algae concentration range within which photobioreactor control system 602 may be configured to maintain the photobioreactor may be determined for a particular application by routine testing and optimization. Such routine testing and optimization may take place in a pilot-scale photobioreactor system or in an automated cell culture management system, as are described in more detail below.

Once a desired algae concentration range has been determined, as described above, control system 602 can be configured to control the algal concentration within this range by detecting the algae concentration within the liquid medium, harvesting the algae, and supplementing the system with fresh liquid medium. To determine the concentration of algae within the photobioreactor, a turbidity meter and/or spectrophotometer 632 (or other appropriate optical density or light absorbance measuring device) can be provided. For example, a spectrophotometer could be used to continuously measure the optical density of the liquid medium and evaluate the algal concentration from the optical density according to standard methods, such as described in Hiroyasu et al. 1998. Of course other methods of determining algae concentration may be used, for example, a cell counter or a measurement of TOC (total organic carbon) may be used.

In general, chemicals for nutrient level maintenance and pH control and other factors may be added automatically directly into the liquid phase within the photobioreactor, if desired. Computer control system 602 can also be configured to control the liquid phase temperature in the photobioreactor by either or both of controlling a heat exchange system or heat control system within or connected with the photobioreactor, or, in alternative embodiments removing liquid medium from the photobioreactor and passing through a heat exchanger in, for example, a temperature controlled water bath (not shown).

As mentioned above, certain preferred embodiments of photobioreactor gas treatment system 600 include a computer-implemented control system 602 configured for controlling liquid flow patterns within photobioreactor 100 so as to provide desired photomodulation characteristics to provide a desired average algae growth rate, for example a maximum average growth rate achievable. In certain embodiments, the photomodulation control system and methodology utilizes two mathematical models to determine optimal or desired liquid flow patterns for optimizing photomodulation. The first mathematical model involves simulating the growth rate of the algae as a function of sequential and alternating exposure to intervals of light and dark, and the second mathematical model involves a simulation of liquid flow patterns within the photobioreactor as a function of system configuration and geometry and flow rates of liquid medium, (and for systems involving gas injection-driven liquid flow, gas injection rates into the photobioreactor). FIGS. 9A and 9B outline two of the many possible strategies for implementing the above-described photomodulation control scheme with computer-implemented control system 602.

Regarding the above-described mathematical models that can be utilized by control system 602 in optimizing photomodulation, the first mathematical model for correlating light/dark exposure intervals (photomodulation) to average growth rate can, in certain embodiments, be based upon a mathematical model proposed in the literature (see Wu and Merchuk, 2001). The model is based upon the hypothesis that the photosynthetic process in algal cells has three basic modes: (1) activated, (2) resting, and (3) photoinhibited. The fraction of an algal population in each of the three above modes can be represented by $x_1$, $x_2$, and $x_3$ respectively (where $x_1+x_2+x_3=1$).

The model proposes that under normal conditions, an active algal culture reaches photosaturation, becomes photoinhibited and must rest at regular intervals for optimal productivity. In the photoinhibition and resting modes, the culture is unable to use light for carbon fixation. Thus, light exposure during periods of photoinhibition or rest is essentially wasted because it is not available for photosynthesis and carbon fixation and can actually be detrimental to the viability of the culture. The proposed model provides a series of differential, time-dependent equations describing the dynamic process by which the algal culture shifts between the activated, resting, and photoinhibited modes:

$$\frac{dx_1}{dt} = -\alpha I x_1 + \gamma x_2 + \delta x_3 \qquad \text{Eq. 1}$$

$$\frac{dx_2}{dt} = \alpha I x_1 - \gamma x_2 - \beta I x_2 \qquad \text{Eq. 2}$$

$$\frac{dx_3}{dt} = \beta I x_2 - \delta x_3 \qquad \text{Eq. 3}$$

while, $$x_1 + x_2 + x_3 = 1 \qquad \text{Eq. 4}$$

and, $$\mu = k\gamma x_2 - Me \qquad \text{Eq. 5}$$

In these equations, $\alpha$ is a rate constant of photon utilization to transfer the algal culture from $x_1$ to $x_2$, $\beta$ is a rate constant describing transfer from $x_2$ to $x_3$ (photoinhibition process), $\gamma$ is a rate constant describing transfer from mode $x_2$ to $x_1$ (dark reaction for biomass production), $\delta$ is a rate constant describing transfer from $x_3$ to $x_1$ (recovery process from photoinhibition), $\mu$ is the specific growth rate, Me is the maintenance coefficient, and k is the dimensionless yield of photosynthesis production to the transition $x_2$ to $x_1$.

In a photobioreactor apparatus such as photobioreactor 100, illumination intensity I will be a complex function of time, depending on the fluid dynamics, light intensity of exposure, and algal concentration within photobioreactor 100. Illumination I as a function of time (i.e. the time history of illumination intensity of the algae as it flows through the photobioreactor) can be determined, as described in more detail below, using a simulation of the fluid dynamics within the photobioreactor. (see also: Wu X. and Merchuk J. "Simulation of Algae Growth in a Bench-Scale Bubble Column Reactor" *Biotechnology and Bioengineering*, 80:pp. 156-168 (2002)(hereinafter "Wu and Merchuk, 2002"); and Wu X. and Merchuk J. "Simulation of algae growth in a bench scale internal loop airlift reactor" *Chemical Engineering Science*, 59:pp. 2899-2912 (2004)(hereinafter "Wu and Merchuk, 2004"); both incorporated herein by reference). Once this parameter is determined, and once the constants $\alpha$, $\gamma$, $\beta$, $\delta$, k, and Me are determined, specific growth rate $\mu$ can be determined for a given illumination history around a flow loop cycle. Solution of these equations may be effected utilizing a wide variety of known numerical techniques for solving differential equations. Such numerical techniques can be facilitated by equation-solving software that is commonly commercially available or can be readily prepared by one of ordinary skill in the art of applied mathematics.

While it can be possible to utilize controlled experiments within a production-scale photobioreactor, such as photobioreactor 100, to determine the appropriate values of the various constants in the above mathematical model via fitting the model to experimental data, in certain embodiments, for simplicity and accuracy, it may be desirable to utilize a pilot photobioreactor system being able to permit precise and direct manipulate of parameters such as the duration, frequency, and intensity of light exposure of the culture. For example, for a photobioreactor system wherein the algal culture is exposed to an essentially uniform light intensity throughout the entire culture and to a series of essentially identical light/dark exposure cycles (i.e. in which successive light/dark exposure cycles are essentially identical), a quasi-steady state analytical solution of the above-equations is possible (see, Wu and Merchuk, 2001).

Such an experimental photobioreactor system could comprise, for example, a small-scale photobioreactor in an automated cell culture system in which the algal cells are subjected to precisely controlled intervals of light and dark exposure at a regular, constant frequency. Alternatively, a pilot-scale, thin-film, bioreactor having fluid flow behavior providing an exact, repetitive light/dark exposure ratio, such as that disclosed in Wu and Merchuk, 2001, could be utilized. Under such quasi-steady state conditions, the mean specific growth rate for one cycle is given by (Wu and Merchuk, 2001):

$$\bar{\mu} = \frac{k\gamma}{t_c} \int_0^{t_c} x_2(t)dt - Me \quad \text{Eq. 6}$$

$$= \frac{k\gamma}{t_c}\left[\int_0^{t_l} x_{2,l}(t)dt + \int_{t_l}^{t_c} x_{2,d}(t)dt\right] - Me$$

$$= \frac{k\gamma}{t_c}\left[\frac{c}{b}t_l + \frac{C_1}{A}(s-1) + \frac{C_2}{B}(n-1) + \left(\frac{c}{b} + C_1 s + C_2 n\right)\frac{u-1}{u\gamma}\right] - Me$$

where, $a = \alpha I + \beta I + \gamma + \delta,$ $b = \alpha\beta I^2 + \delta\gamma + \alpha I\delta + \beta I\delta,$ $c = \alpha I\delta;$ and $$A = -\frac{a + \sqrt{a^2 - 4b}}{2},$$

$$B = -\frac{a - \sqrt{a^2 - 4b}}{2}$$

and $$C_1 = -\frac{Bc(u-1)(n-v) + \alpha Ib(n-u)(v-1) + c(\alpha I + \beta I + \gamma)(n-1)(u-v)}{b\left[\begin{array}{l}B(s-u)(n-v) - \\ A(n-u)(s-v) + (\alpha I + \beta I + \gamma)(s-n)(u-v)\end{array}\right]}$$

$$C_2 = -\frac{Ac(u-1)(s-v) + \alpha Ib(s-u)(v-1) + c(\alpha I + \beta I + \gamma)(s-1)(u-v)}{b\left[\begin{array}{l}B(s-u)(n-v) - \\ A(n-u)(s-v) + (\alpha I + \beta I + \gamma)(s-n)(u-v)\end{array}\right]}$$

where $s = e^{At_l}, n = e^{Bt_l}, u = e^{\gamma t_d}, v = e^{\delta t_d}$

In these equations, t is time, $t_l$ is the time during the cycle in which the algal culture is exposed to light at an intensity capable of driving photosynthesis, $t_d$ is the time during the cycle during which the algal culture is exposed to dark or light at an intensity incapable of driving photosynthesis and $t_c$ is the total cycle time (i.e. $t_l + t_d$).

The above equations describing the analytical solution may be curve fit to experimental data of algal growth rate as a function of time to determine the values of the various constants (e.g., as described in Wu and Merchuk, 2001). For example, using the above approach, Wu and Merchuk, 2001 determined the following values for the constants in Eqs. 1-5 for a culture of red marine algae, *Porphyridium* sp. (UTEX 637) to be:

TABLE 1

Adjustable Parameter Values and 95% confidence intervals

| Parameter | Value | 95% confidence interval |
|---|---|---|
| $\alpha$ | 0.001935 µE m$^{-2}$ | −0.00189-0.00576 |
| $\beta$ | 5.7848 × 10$^{-7}$ µE m$^{-2}$ | −0.000343-0.000344 |
| $\gamma$ | 0.1460 s$^{-1}$ | −0.133-0.425 |
| $\delta$ | 0.0004796 s$^{-1}$ | −0.284-0.285 |
| k | 0.0003647 (dimensionless) | −0.000531-0.00126 |
| Me | 0.05908 h$^{-1}$ | −0.0126-0.131 |

The mathematical model utilized by computer-implemented control system 602 to determine liquid flow patterns within the photobioreactor as a function of liquid flow rate and/or overall gas injection rate and gas-injection distribution to spargers 122 and 124 can comprise a commercially available Computational Fluid Dynamics (CFD) software package, such as FLUENT™ (e.g. FLUENT 6.1) or FIDAP™ (Fluent Incorporated, Lebanon, N.H.), or another known software package, or custom-designed CFD software program providing a two-dimensional, or preferably three-dimensional solution to the Navier-Stokes Equations of Motion (e.g. see, Doering, Charles R. and J. D. Gibbon, Applied Analysis of the Navier-Stokes Equations, Cambridge University Press 2001, incorporated herein by reference). Those of ordinary skill in the art of fluid mechanics and computational fluid dynamics can readily devise such fluid flow simulations and, alone or in combination with one of ordinary skill in the art of computer programming, prepare software to implement such simulations. In such simulations, finite element mathematical techniques may be utilized and such computations may be performed or assisted using a wide variety of readily available general purpose or fluid-flow specific finite element software packages (for example one or more of those available from ALGOR, Inc., Pittsburgh, Pa. (e.g. ALGOR's "Professional Fluid Flow" software package)).

For example, in certain embodiments for simulating fluid flow using CFD, a Euler-Euler approach can be used for the 3-D numerical calculation of the multiphase (liquid-air) flows. In the Euler-Euler approach, the different phases are treated mathematically as interpenetrating continua. Since the volume of a phase cannot be occupied by the other phases, the concept of phase volume fraction is introduced. These volume fractions are assumed to be continuous functions of space and time and their sum is equal to one. Conservation equations for each phase are derived to obtain a set of equations, which have similar structure for all phases. More specially, the mixture model is designed for two or more phases (fluid or particulate) and treats phases as interpenetrating continua. The mixture model solves for the mixture momentum equation and prescribes relative velocities to describe the dispersed phases. The mixture model allows the phases to be interpenetrating. The volume fractions $\alpha_p$ and $\alpha_q$ for a control volume can be equal to any value between 0 and 1, depending on the space occupied by the phases p and q. The mixture model allows the phases to move at different velocities, using the concept of slip velocities.

The mixture model solves the continuity equation for the mixture, the momentum equation for the mixture, the energy equation for the mixture, and the volume fraction equation for the secondary phases, as well as algebraic expressions for the relative velocities. Governing equations for one embodiment of a CFD simulation are listed below:

Continuity Equation:

$$\frac{\partial}{\partial t}(\rho_m) + \nabla \cdot (\rho_m \vec{v}_m) = \dot{m} \quad \text{(Eq. 7)}$$

Momentum Equation:

$$\frac{\partial}{\partial t}(\rho_m \vec{v}_m) + \nabla \cdot (\rho_m \vec{v}_m \vec{v}_m) = -\nabla p + \quad \text{(Eq. 8)}$$

$$\nabla \cdot [\mu_m (\nabla \vec{v}_m + \nabla \vec{v}_m^T)] + \rho_m \vec{g} + \vec{F} + \nabla \cdot \left( \sum_{k=1}^{n} \alpha_k \rho_k \vec{v}_{dr,k} \vec{v}_{dr,k} \right)$$

$$\vec{v}_{dr,k} = \vec{v}_k - \vec{v}_m \quad \text{(Eq. 9)}$$

Energy Equation:

$$\frac{\partial}{\partial t} \sum_{k=1}^{n}(\alpha_k \rho_k E_k) + \nabla \cdot \sum_{k=1}^{n}(\alpha_k \vec{v}_k(\rho_k E_k + p)) = \nabla \cdot (k_{eff} \nabla T) + S_E \quad \text{(Eq. 10)}$$

Volume Fraction Equation for Phase p:

$$\frac{\partial}{\partial t}(\alpha_p \rho_p) + \nabla \cdot (\alpha_p \rho_p \vec{v}_m) = -\nabla \cdot (\alpha_p \rho_p \vec{v}_{dr,p}) \quad \text{(Eq. 11)}$$

where $\vec{v}_m$ is the mass-averaged velocity, $\eta_m$ is the mixture density, and $\dot{m}$ is the mass transfer due to cavitation, where n is the number of phases, $\vec{F}$ is a body force, $\mu_m$ is the viscosity of the mixture, and $\vec{v}_{dr,k}$ is the drift velocity for secondary phase k, $k_{eff}$ is the effective conductivity (equal to $k+k_t$, where $k_t$ is the turbulent thermal conductivity, defined according to any turbulence model being used), and $S_E$ includes any other volumetric heat sources. The equations may be solved using known CFD schemes and can be simulated using FLUENT 6.1. Turbulent effects may also be considered by solving a standard k–ϵ two-equation model.

In the photobioreactor system 600 illustrated in FIG. 7A utilizing photobioreactor 100, the CFD simulation performed by computer implemented control system 602 in certain embodiments can determine, for each passage of algae around the flow loop (i.e., each cycle of the algae as it moves around the flow path provided by channels 104 and 106 of photobioreactor 100), the duration and frequency of the light and dark intervals to which the algae is exposed (i.e. the photomodulation pattern). In certain embodiments, the CFD model can account for the physical geometry of the photobioreactor and the various flow sources and sinks of the photobioreactor to determine the bulk flow and liquid flow patterns of the liquid medium in each of two channels of photobioreactor 100. A moderate-to-tight finite element grid spacing could be selected to discern and analyze flow streamlines at the algae scale, for example on the order of ten algal cell diameters. The output of the CFD simulation will be the expected streamlines which show the path of fluid-driven cells into and out of light and dark regions and the photobioreactor. From these streamlines, the duration of light and dark exposure and the frequency with which the algae moves from light to dark exposure as it traverses the flow loop can be determined, and this illumination versus time relationship can be utilized in the above-described cell growth/photo modulation model to determine average growth rate around the flow loop. In some cases, the simulation also takes into consideration the effect of cell concentration/growth/polysacahharide secretion on the viscosity of the liquid medium and/or the effect of shear stress on the growth dynamics of the cells, as discussed, for example in Wu and Merchuk, 2002 and Wu and Merchuk, 2004. For example, to account for shear stress effects, the maintenance coefficient, Me, can be taken to be a function of the shear rate/stress above a critical shear stress, $\tau_c$ found to be a threshold for affecting growth rate, as follows:

$$\text{Me} = \overline{\text{Me}} \bullet e^{k_m(\tau - \tau_c)}$$

With the global shear rate (γ') in a bubbling duct of length $L_R$, gas liquid contact area a, flow behavior index n, fluid consistency index κ (Pa·s$^n$), gas superficial velocity $J_G$ and pressure $p_1$, $p_2$ in the bottom and top given by:

$$\gamma' = \left( \frac{p_1 J_G \ln(p_1/p_2)}{a L_R^2 \kappa} \right)^{\frac{1}{n}}$$

(see, e.g. Wu and Merchuk, 2002 and Wu and Merchuk, 2004). Examples of fluid flow simulations for a bubble column reactor design and an internal loop airlift reactor design and their integration with the above-discussed growth model of Wu and Merchuk, 2001 have recently been published in Wu and Merchuk, 2002 and Wu and Merchuk, 2004, respectively.

If desired, experimental validation of the results of the CFD simulations can be performed using flow visualization studies of the actual flow trajectories in the photobioreactor. Such studies may be conducted by utilizing neutrally buoyant microspheres, simulating algal cells. In one particular embodiment, a laser can be configured and positioned to create a longitudinal sheet of coherent light through the active segment (i.e., channel 104) of the photobioreactor. Such a plane of laser illumination can be positioned to represent the boundary between "light" and "dark" regions. Its position can be adjusted to represent various expected light-dark transition depths within the conduit expected over the range of algal concentrations and illumination intensities that may be present during operation of the photobioreactor. In one embodiment, a combination of clear silica and fluorescent microspheres (available from Duke Scientific Corporation, Palo Alto, Calif.) could be used to model algae particles. The diameter and density of the microspheres may be selected to correspond to the particular strain of algae expected to be used in the photobioreactor. As the fluorescent microspheres cross the laser plane, they would scatter the laser beam and create a detectable "flash." A video camera can be positioned to record such flashes, and the time between flashes can be used to measure the residence time of the particle in each of the two areas (i.e. the light and dark areas). A second laser plane could be generated, if desired, to visualize flow within an essentially perpendicular plane to the above longitudinal sheet, if it is desired to have a more detailed representation of the actual position of the various fluorescent microspheres within the cross section of the illuminated conduit. One example of an optical trajectory tracking system and method for determining flow patterns in an internal loop airlift bioreactor, which could be utilized in the present context, was recently described in Wu X. and Merchuk J. "Measurement of fluid flow in the downcomer of an internal loop airlift reactor using an optical trajectory-tracking system" *Chemical Engi-*

*neering Science,* 58:pp. 1599-1614 (2003)(hereinafter "Wu and Merchuk, 2003"), incorporated herein by reference.

In general, a wide variety of known non-invasive measuring technologies may be utilized or adapted to study multiphase flows in the photobioreactors of the invention, such as, for example Laser Doppler Velocimetry (LDV), Radioactivity Particle Tracking (RPT) (Larachi, F., Chaouki, J., Kennedy, G. And Dudukovic, M. P., 1996. Radioactivity Particle Tracking in Multiphase Reactors: Principles and Applications. J. Chauki, F. Larachi and M. P. Dudukovic, editor. Non-Invasive Monitoring of Multiphase Flow. Elsevier Science B. V. 335-406, incorporated herein by reference (hereinafter "Larachi 1996")), Particle Image Velocimetry (PIV), X-ray tomography, NMR image technology, and Computer Automated Radioactive Particle Tracking (CARPT) and gamma ray Computed Tomography (CT) (Larachi 1996; Larachi, F., Kennedy, G. and Chaouki, J., "A γ-ray Detection System for 3-D Particle Tracking in Multiphase Reactors", Nucl. Instr. & Meth., A338, 568 (1994) (hereinafter "Larachi 1994"); Devanathan, N., Moslemian, D. And Dudukovic, M. P., 1990. Flow Mapping in Bubble Columns Using CARPT. Chem. Eng. Sci. 45:2285-2291; Kumar, B. S., Moslemian, D. and, Dudukovic, M. P., "A γ-ray Tomographic Scarrier for Imaging of Void Distribution in Two-Phase Flow Systems", Flow Meas. Instrum., 6(3), 61 (1995); Kumar, S. B., Moslemian, D. and Dudukovic, M. P., "Gas Holdup Measurements in Bubble Columns Using Computed Tomography", AIChE J., 43(6), 1414 (1997); each incorporated herein by reference).

Computer Automated Particle Tracking Technique (CARPT) is based on following the motion of a single tracer particle and is a method of Lagrangian mapping of the velocity field in the whole system. The technique was introduced for monitoring the solids in fluidized beds by Lin et al. (1985) (Lin, J. S., Chen, M. M. and Chao, B. T., "A Novel Radioactive Particle Tracking Facility for Measurement of Solids Motion in Gas Fluidized Beds", AIChE J., 31, 465 (1985); incorporated herein by reference) and can be adapted for measurement of liquid velocities in bubble columns. For tracing liquid phase flow, a single neutrally buoyant radioactive particle dynamically similar to the liquid phase may be introduced into the system. For tracing biomass, a particle of the same size and density as the biomass may be introduced. Specifically, in certain embodiments, a hollow polypropylene bead, about 2 mm in diameter, can be used. A small amount of Scandium 46 (e.g. approximately 250 µCu for the purpose of proposed measurements) may be injected into the bead. It is desirable that the density of the composite particle comprising polypropylene, scandium and air gap is matching that of the liquid as closely as possible. In certain embodiments, a thin film metallic coating may assure that bubbles do not preferentially adhere to the particle.

An array of scintillation detectors can be located around the channel(s)/conduit(s) of the photobioreactor under study. In certain embodiments, up to 32 NaI two (2) inch detectors are used. The detectors may be calibrated in situ with the tracer particle to be used to get the counts-positions maps. CARPT calibration is routinely done by positioning the tracer particle (e.g. containing 250 µCu of Sc-46) at about 1000 known locations and recording the counts obtained at each detector. his calibration is performed to take into account the relative position of the sensors, and the effects of the different materials such as water, the reactor wall, etc on the output.

The processing of data obtained from the flow trajectory experiments may proceed as follows. From filtered particle positions at subsequent times the instantaneous velocity can be calculated and assigned to a fictitious column compartment (for embodiments where a compartmental grid is pre-established for the column) into which the midpoint falls. The time of tracking should be adjusted ensure that statistical significance is ensured (e.g. for typical photobioreactors, data recorded over 24 hours of tracking yield good statistical significance). For each compartment studied, average velocities of tracking particles can be evaluated, and the fluctuating velocity vector can be calculated from the difference between the instantaneous and average velocity. This can allow for the evaluation of most important Eulerian autocorrelations and cross-correlations. Kinetic turbulent energy and components of the Reynolds stresses can then be obtained. The Lagrangian auto-correlations can enable the evaluation of eddy diffusivities by known methods.

An alternative way of constructing flow maps is via modeling of particle emission of photons and their transmission and subsequent detection at the detectors. The Monte Carlo method (Gupta, P., "Monte Carlo Simulation of NaI Detectors Efficiencies for Radioactive Particle Tracking in Multiphase Flows", CREL Annual Report, Washington University, p. 117 (1998); incorporated herein by reference) in which the photon histories are tracked in their flight from the source, through the attenuating medium and their final detection (or lack of it) at the detector can be used for this purpose. Thus, both the geometry and radiation effects may be accounted for in the estimation of the detector efficiencies in capturing and recording the photons. This involves evaluation of three-dimensional integrals which are calculated using the Monte Carlo approach by sampling modeled photon histories over many directions of their flight from the source. Once the calibration is complete, the tracer particle may be let loose in the system and the operating conditions are controlled for the entire duration of particle tracking. A least-squares regression method can be used to evaluate the position of the particle. Sampling frequency may be adjusted to assure desired accuracy. In certain embodiments, for example, it is selected to be about 50 Hz. A wavelet based filtering algorithm may be employed to remove/reduce noise in position readings created by the statistical nature of gamma radiation.

By employing CARPT, it is possible to obtain multiple particle trajectories (e.g. many thousands) from which mean velocity profiles and radial and axial eddy diffusivities may be calculated. CARPT results can allow the calculation of the turbulent shear field to which the particle is exposed at each operating condition. Since CARPT provides Lagrangian data, eddy diffusivities can be obtained from first principles.

In addition, by positioning additional scintillation detectors at the entry and exit of the channel(s) of the photobioreactor it also possible to determine via CARPT the residence time distribution in each channel as well as the particle trajectory length distribution. Moreover, since it is possible to obtain a substantially complete spatial description of multiple particle trajectories, based on Beer Lambert's law it is possible to define the zone of illumination of certain magnitude and describe the sojourn time distribution of biomass in the illumination and dark zones.

The captured trajectories of the tracer particles can be used to generate velocity vectors. To do this, for an embodiment where a photobioreactor of a configuration such as illustrated in FIG. 1A is under study, the solar channel 104 of inclined conduit 102 of the photobioreactor can be meshed. The velocity vectors in each meshed unit can be long-term averaged and a representative velocity vector of that mesh can be obtained. Then by averaging the velocities in the same cross sectional plane, the superficial liquid velocity profile along axis direction of the inclined channel can be calculated according to:

$$U_i = \frac{\sum \overline{u_{r,\theta,i}}}{n} \quad \text{(Eqn. 12)}$$

Where $\overline{u_{r,\theta,i}}$ is the average liquid velocity at mesh position (r, θ, i); $\overline{U_i}$ is the superficial liquid velocity at cross sectional plane i; n is the number of meshes in the cross sectional plane; i is the cross sectional plane index; r and θ are position index for radius and phase angle direction. From this the residence time $T_S$ of a liquid package in the solar channel 104 can then be determined.

One method to measure the residence time distribution (RTD) is to measure the time required for a neutral buoyancy tracer particle to pass through the inclined channel. For example, 3-6 passes can be measured and an average RTD can be obtained. The measured RTD by this method can be compared to that obtained by CARPT for a consistency check. The results for both methods can be used to estimate the residence time in the other channel(s) of the photobioreactor by applying a basic mass balance; for example for a photobioreactor configuration as illustrated in FIG. 1A:

$$J_{L,S} = \frac{L_S}{T_S} \quad \text{(Eqn. 13)}$$

$$J_{L,S} A_S (1 - \varepsilon_S) = J_{L,D} A_D (1 - \varepsilon_D) \quad \text{(Eqn. 14)}$$

$$T_D = \frac{L_D}{J_{L,D}} \quad \text{(Eqn. 15)}$$

Where J is the superficial liquid velocity; T is the residence time; A is the cross sectional area; g is gas holdup; L for the length for the channels; the subscript L is for liquid, S for solar channel 104, D for dark channel 106.

Gamma Ray Computed Tomography is a well-established technique for measuring the phase holdup distribution at any desired cross-section of an air-lift reactor. In certain embodiments, a gamma source based fan beam type CT unit can be utilized. For example, in an exemplary embodiment, a collimated hard source (e.g. about 100 mCi of Cs-137) may be positioned opposite eleven 2 inch NaI detectors in a fan beam arrangement. The lead collimators in front of the detectors may have manufactured slits and the lead assembly may be configured to move so as to allow repeated use of the same detectors for additional projections. A 360° scan can be executed at essentially any desired axial location to facilitate scanning of a wide range of channel dimensions.

The principle of computed tomography is relatively simple. From the measured attenuation of the beams of radiation through the two phase mixture (projections) it is possible to calculate, due to the different attenuation by each phase, the distribution of phases in the cross-section that was scanned. In certain embodiments, it is possible to achieve, for example, about 3465 to about 4000 projections and obtain a spatial resolution of about 2 mm and density resolution of about 0.04 g/cm³. Because of the time that may be required to scan the entire cross-section, it may be advantageous to assess time-averaged density distributions. A variety of techniques for reconvolution or filtered back projection may be employed, such as algebraic reconstruction and estimation-maximization algorithms (E-M) (Larachi et al, 1994).

Figure 9A:
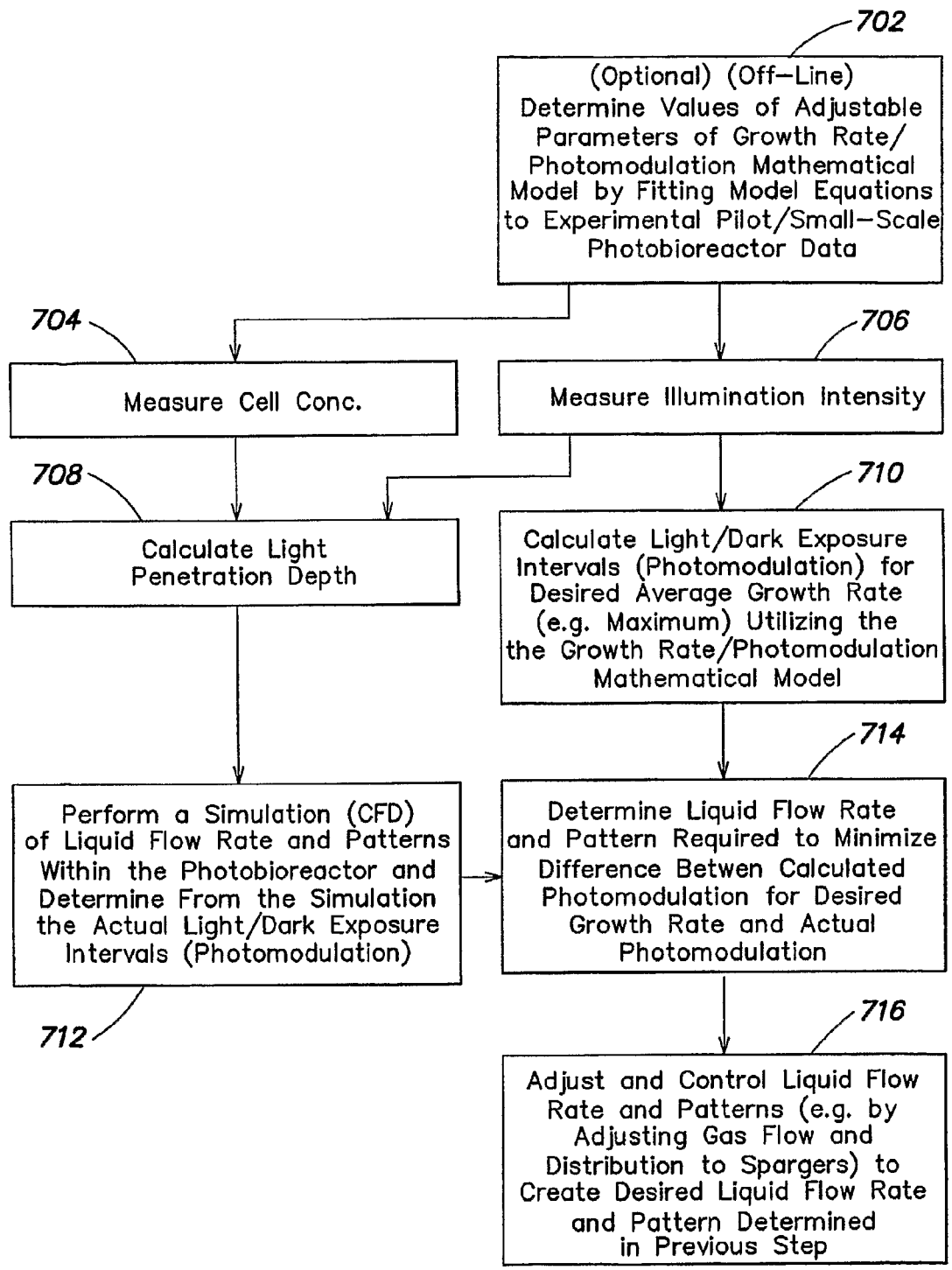
FIG. 9A is a block flow diagram illustrating one embodiment of a method for operating the computer-implemented control system of the photobioreactor system of FIG. 7A.
Figure 9B:
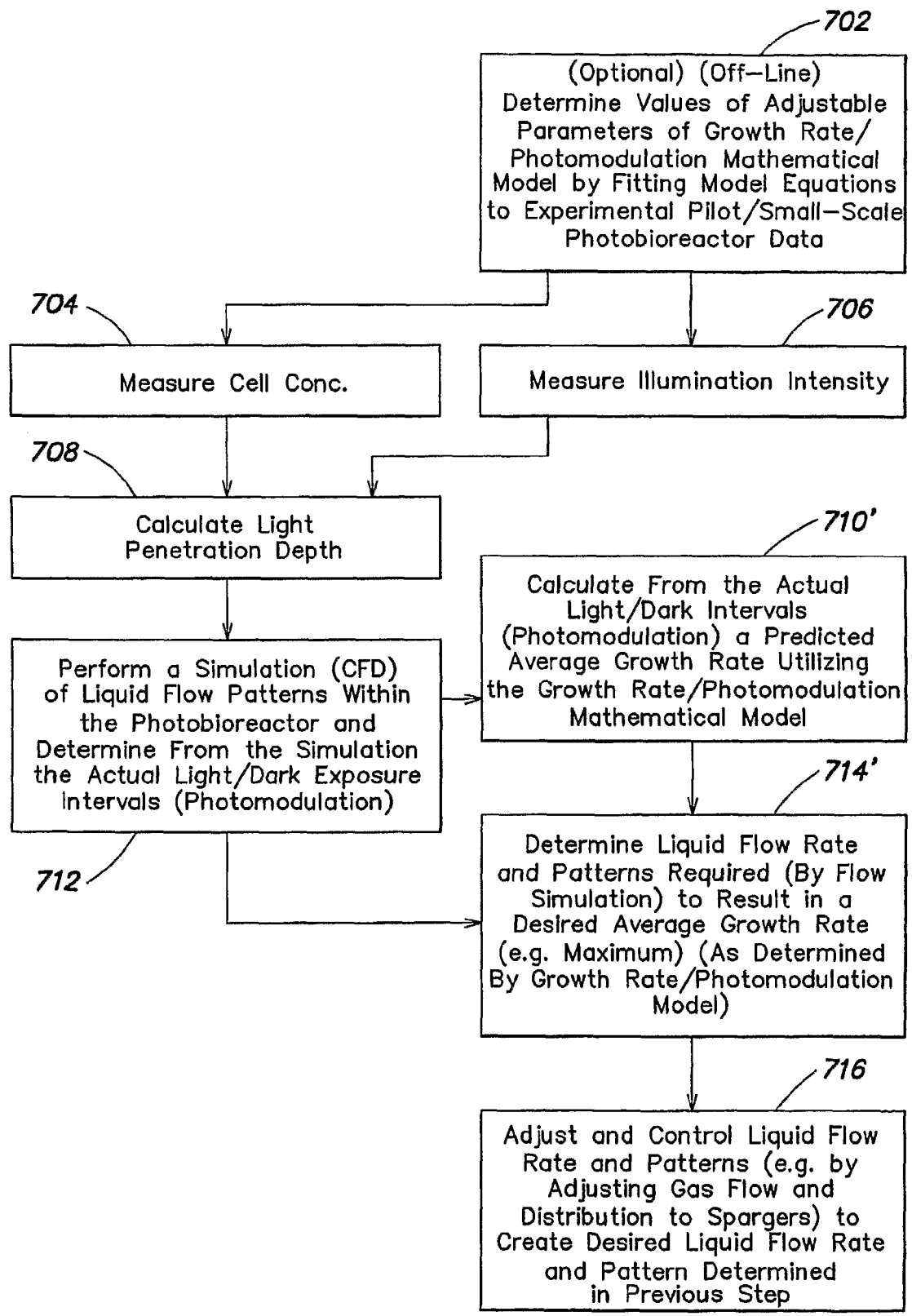
FIG. 9B is a block flow diagram illustrating another embodiment of a method for operating the computer-implemented control system of the photobioreactor system of FIG. 7A.

Referring now to FIGS. 9A and 9B, two alternative computational and control methodologies for controlling and optimizing photomodulation in the photobioreactor of system 600 are described. The methodologies are similar and differ, primarily, in the computational parameters utilized for convergence (i.e. light/dark exposure intervals in the method of FIG. 9A, and predicted growth rate in the FIG. 9B method).

Reference is made now to FIG. 9A, in which one embodiment for creating and controlling photomodulation within a photobioreactor of a gas treatment system is disclosed. Initial step 702 is an optional model fitting step, which may be conducted off-line with a pilot-scale or small-scale automated cell culture and testing system, as discussed above. Optional step 702 involves determining appropriate values of the various adjustable parameters comprising the constants of the growth rate/photomodulation mathematical model described above by fitting the model equations to experimental growth rate versus light/dark exposure interval data, as described above and in Wu and Merchuk, 2001.

In step 704, cell concentration within photobioreactor 100 is measured, for example through use of spectrophotometer 632. In step 706, the light intensity incident upon the active channel 104 of the photobioreactor is measured utilizing a light intensity measuring device (e.g., a light meter) 633. The measured cell concentration and illumination intensity may together be used to calculate, in step 708, the light penetration depth within tubular conduit 102 or channel 104 according to standard, well known methods (e.g., as described in Burlew, 1961).

In step 710, a mathematical calculation is performed to calculate, from the growth rate/photomodulation mathematical model, predicted light/dark exposure intervals (i.e., duration and frequency of light/dark exposure) required to yield a desired average growth rate, for example a maximal growth rate achievable (i.e. given the non-adjustable operating constraints of the system).

In step 712, computer-implemented system 602 performs a simulation (e.g., CFD simulation) of the liquid medium flow and determines the flow streamlines and patterns within the photobioreactor for a particular total gas flow rate and gas flow distribution to spargers 122 and 124. From the simulation, actual light/dark exposure intervals and photomodulation of the algae as it flows around the flow loop can be determined. The system can determine when algae within the liquid medium is exposed to light within active channel 104 by determining when it is within a region of the channel separated from the light exposed surface 132 by a distance not exceeding that which, as determined in the light penetration depth determination of step 708, would expose the algae to light at an intensity above that which is sufficient to drive photosynthesis (i.e. above that required to render the algae in the "active" photosynthetic mode as described in the above-discussed growth/photomodulation model). The precise light intensity, and corresponding penetration depth, required for active photosynthesis for a particular type or mixture of algae can be determined using routine experimental studies of algal growth versus light intensity in a model photobioreactor system.

In step 714, the light/dark exposure intervals and photomodulation characteristics determined in step 710 required to give a desired average growth rate are compared with the actual light/dark exposure intervals and photomodulation characteristics prevailing in the photobioreactor as determined in step 712. The simulation of step 712 is then repeated utilizing different gas flows and gas flow distributions until the difference between the exposure intervals determined in steps 710 and 712 is minimized and the simulations converge.

In step 716, computer-implemented system 602 adjusts and controls the liquid flow rate within the photobioreactor and the liquid flow patterns (e.g., recirculation vortices) by, for example, adjusting the gas flow and gas distribution to spargers 122 and 124 so as to match the optimal values determined in step 714.

The alternative photomodulation determination and control methodology in FIG. 9B is similar to that disclosed in FIG. 9A, except that instead of the CFD and growth rate/photomodulation mathematical models converging upon calculated light/dark exposure intervals, the system is configured to run the simulations to determine flow parameters required to yield a desired predicted (i.e. by the growth rate/photomodulation model) growth rate.

Steps 702, 704, 706, 708, 712 and 716 can be performed essentially identically as described above in the context of the method outlined in FIG. 9A. In the method shown in FIG. 9B, however, the actual light/dark exposure intervals and photomodulation data determined from the CFD simulation of step 712 is then utilized in step 710' to calculate, utilizing the growth rate/photomodulation mathematical model, an average predicted growth rate that would result from such light/dark exposure characteristics. Step 712 is then repeated with different values of gas flow and gas distribution and a new predicted average growth rate is determined in step 710'. The computational procedure is configured to adjust the values in step 712 in order to converge in step 714' upon a desired average growth rate as determined in step 710', for example a maximum achievable growth rate. Once gas flow and gas distribution values resulting in such a predicted desired growth rate are determined, computer-implemented control system 602 then applies these gas flow rates and distributions to the photobioreactor to induce the desired liquid flow dynamics in the system in step 716.

It should be appreciated that the above-described photomodulation control methodologies and systems can advantageously enable automated operation of the photobioreactor under conditions designed to create an optimal level of photomodulation. Advantageously, the system can be configured to continuously receive input from the various sensors and implement the methodologies described above so as to optimize photomodulation in essentially real time (i.e. with turnaround as fast as the computations can be performed by the system). This can enable the system to be quickly and robustly responsive to environmental condition changes that can change the nature and degree of photomodulation within the system. For example, in a particular embodiment and under one exemplary circumstance, computer-implemented control system 602 could quickly and appropriately adjust the gas flow rates and distribution and, thereby, the liquid flow patterns and photomodulation within the photobioreactor, so as to account for transient changes in illumination, such as the transient passing of cloud cover, over a period of operation of the photobioreactor system.

The calculation methods, steps, simulations, algorithms, systems, and system elements described above may be implemented using a computer-implemented system, such as the various embodiments of computer-implemented systems described below. The methods, steps, systems, and system elements described above are not limited in their implementation to any specific computer system described herein, as many other different machines may be used.

The computer-implemented system can be part of or coupled in operative association with a photobioreactor, and, in some embodiments, configured and/or programmed to control and adjust operational parameters of the photobioreactor as well as analyze and calculate values, as described above. In some embodiments, the computer-implemented system can send and receive control signals to set and/or control operating parameters of the photobioreactor and, optionally, other system apparatus. In other embodiments, the computer-implemented system can be separate from and/or remotely located with respect to the photobioreactor and may be configured to receive data from one or more remote photobioreactor apparatus via indirect and/or portable means, such as via portable electronic data storage devices, such as magnetic disks, or via communication over a computer network, such as the Internet or a local intranet.

Referring to FIGS. 4 and 7A, computer-implemented control systems 312 and 602 may include several known components and circuitry, including a processing unit (i.e., processor), a memory system, input and output devices and interfaces (e.g., an interconnection mechanism), as well as other components, such as transport circuitry (e.g., one or more busses), a video and audio data input/output (I/O) subsystem, special-purpose hardware, as well as other components and circuitry, as described below in more detail. Further, the computer system may be a multi-processor computer system or may include multiple computers connected over a computer network.

The computer-implemented control systems may include a processor, for example, a commercially available processor such as one of the series x86, CELERON-, XScale- and PENTIUM-type processors, available from Intel, similar devices from AMD and Cyrix, the 680X0 series microprocessors and DragonBall processors available from Motorola, and the PowerPC microprocessor, HPC from IBM, the Sun UltraSPARC, Hewlett-Packard PA-RISC processors, or any of a variety of processors available from Advanced Micro Devices (AMD). Many other processors are available, and the computer system is not limited to a particular processor.

A processor typically executes a program called an operating system, of which Windows NT, Windows95 or 98, Windows 2000 (Windows ME), Windows XP, Windows CE, Pocket PC, UNIX, Linux, DOS, VMS, MacOS and OS8, the Solaris operating system (Sun Microsystems), Palm OS are examples, which controls the execution of other computer programs and provides scheduling, debugging, input/output control, accounting, compilation, storage assignment, data management and memory management, communication control and related services. The processor and operating system together define a computer platform for which application programs in high-level programming languages are written. The computer implemented control systems are not limited to a particular computer platform.

The computer-implemented control systems may include a memory system, which typically includes a computer readable and writeable non-volatile recording medium, of which a magnetic disk, optical disk, a flash memory and tape are examples. Such a recording medium may be removable, for example, a floppy disk, read/write CD or memory stick, or may be permanent, for example, a hard drive.

Such a recording medium stores signals, typically in binary form (i.e., a form interpreted as a sequence of one and zeros). A disk (e.g., magnetic or optical) has a number of tracks, on which such signals may be stored, typically in binary form, i.e., a form interpreted as a sequence of ones and zeros. Such signals may define a software program, e.g., an application program, to be executed by the microprocessor, or information to be processed by the application program.

The memory system of the computer-implemented control systems also may include an integrated circuit memory element, which typically is a volatile, random access memory such as a dynamic random access memory (DRAM) or static memory (SRAM). Typically, in operation, the processor causes programs and data to be read from the non-volatile recording medium into the integrated circuit memory element, which typically allows for faster access to the program instructions and data by the processor than does the non-volatile recording medium.

The processor generally manipulates the data within the integrated circuit memory element in accordance with the program instructions and then copies the manipulated data to the non-volatile recording medium after processing is completed. A variety of mechanisms are known for managing data movement between the non-volatile recording medium and the integrated circuit memory element, and the computer-implemented control systems that implements the methods, steps, systems and system elements described above in relation to FIGS. 4, 7A, 9A and 9B are not limited thereto. The computer-implemented control systems are not limited to a particular memory system.

At least part of such a memory system described above may be used to store one or more data structures (e.g., look-up tables) or equations described above. For example, at least part of the non-volatile recording medium may store at least part of a database that includes one or more of such data structures. Such a database may be any of a variety of types of databases, for example, a file system including one or more flat-file data structures where data is organized into data units separated by delimiters, a relational database where data is organized into data units stored in tables, an object-oriented database where data is organized into data units stored as objects, another type of database, or any combination thereof.

The computer-implemented control systems may include a video and audio data I/O subsystem. An audio portion of the subsystem may include an analog-to-digital (A/D) converter, which receives analog audio information and converts it to digital information. The digital information may be compressed using known compression systems for storage on the hard disk to use at another time. A typical video portion of the I/O subsystem may include a video image compressor/decompressor of which many are known in the art. Such compressor/decompressors convert analog video information into compressed digital information, and vice-versa. The compressed digital information may be stored on hard disk for use at a later time.

The computer-implemented control systems may include one or more output devices. Example output devices include a cathode ray tube (CRT) display 603, liquid crystal displays (LCD) and other video output devices, printers, communication devices such as a modem or network interface, storage devices such as disk or tape, and audio output devices such as a speaker.

The computer-implemented control systems also may include one or more input devices. Example input devices include a keyboard, keypad, track ball, mouse, pen and tablet, communication devices such as described above, and data input devices such as audio and video capture devices and sensors. The computer-implemented control systems are not limited to the particular input or output devices described herein.

The computer implemented control systems may include specially programmed, special purpose hardware, for example, an application-specific integrated circuit (ASIC). Such special-purpose hardware may be configured to implement one or more of the methods, steps, simulations, algorithms, systems, and system elements described above.

The computer implemented control systems and components thereof may be programmable using any of a variety of one or more suitable computer programming languages. Such languages may include procedural programming languages, for example, C, Pascal, Fortran, COBOL and BASIC, object-oriented languages, for example, C# (C-Sharp), C++, Small-Talk, Java, Ada and Eiffel, Lab View, and other languages, such as a scripting language or even assembly language. Various aspects of the invention may be implemented in a non-programmed environment (e.g., documents created in HTML, XML or other format that, when viewed in a window of a browser program, render aspects of a graphical-user interface (GUI) or perform other functions). Various aspects of the invention may be implemented as programmed or non-programmed elements, or any combination thereof. Further, various embodiments of the invention may be implemented using Microsoft.NET technology available from Microsoft Corporation.

The methods, steps, simulations, algorithms, systems, and system elements may be implemented using any of a variety of suitable programming languages, including procedural programming languages, object-oriented programming languages, other languages and combinations thereof, which may be executed by such a computer system. Such methods, steps, simulations, algorithms, systems, and system elements can be implemented as separate modules of a computer program, or can be implemented individually as separate computer programs. Such modules and programs can be executed on separate computers.

The methods, steps, simulations, algorithms, systems, and system elements described above may be implemented in software, hardware or firmware, or any combination of the three, as part of the computer-implemented control systems described above or as an independent component.

Such methods, steps, simulations, algorithms, systems, and system elements, either individually or in combination, may be implemented as a computer program product tangibly embodied as computer-readable signals on a computer-readable medium, for example, a non-volatile recording medium, an integrated circuit memory element, or a combination thereof. For each such method, step, simulation, algorithm, system, or system element, such a computer program product may comprise computer-readable signals tangibly embodied on the computer-readable medium that define instructions, for example, as part of one or more programs, that, as a result of being executed by a computer, instruct the computer to perform the method, step, simulation, algorithm, system, or system element.

In another set of embodiments, the invention also provides methods for pre-adapting and pre-conditioning algae or other photosynthetic organisms to specific environmental and operating conditions expected to be experienced in a full scale photobioreactor during use. As mentioned above, the productivity and long-term reliability of algae utilized in a photobioreactor system for removing $CO_2$, $NO_X$ and/or other pollutant components from a gas stream can be enhanced by utilizing algal strains and species that are native or otherwise well suited to conditions and localities in which the photobioreactor system will be utilized.

As is known in the art (see, for example, Morita, M., Y. Watanabe, and H. Saiki, "Instruction of Microalgal Biomass Production for Practically Higher Photosynthetic Performance Using a Photobioreactor." *Trans IchemE. Vol.* 79, Part C, September 2001.), algal cultures that have been exposed to and allowed to proliferate under certain sets of conditions can become better adapted and suited for long term growth and productivity under similar conditions. The present invention provides methods for reproducibly and predictably pre-conditioning and pre-adapting algal cultures to increase their long term viability and productivity under a particular expected set of operating conditions and to prevent photobioreactors inoculated with such algal species from having other, undesirable algal strains contaminating and dominating the algal culture in the photobioreactor over time. In certain embodiments the photosynthetic organisms that are pre-conditioned and adapted according to the techniques of the invention are non-recombinant organisms and are not, and have not been, subjected to any genetic modification techniques involving recombinant genetic manipulation or artificially-induced mutagenesis, e.g. chemically-induced mutagenesis—(i.e. "non-natural mutagenesis," e.g. via exposure of the organisms to mutagenic levels of known mutagenic agents, e.g. ethidium bromide, nitrosoguanadine, etc., and/or levels of radiation, e.g. UV radiation, substantially exceeding levels to which the photosynthetic organisms would be exposed via exposure to natural radiation sources, e.g. natural sunlight, etc.).

In many current photobioreactor systems, chosen, desirable strains of algae can be difficult to maintain in a photobioreactor that is not scrupulously sterilized and maintained in a condition that is sealed from the external environment. The reason for this is that the algal strains being utilized in such photobioreactors are not well adapted or optimized for the conditions of use, and other, endemic algal strains in the atmosphere are more suitably conditioned for the local environment, such that if they have the ability to contaminate the photobioreactor they will tend to predominate and eventually displace the desired algae species. Such phenomena can be mitigated and/or eliminated by using the inventive adaptation protocols and algal cultures by practicing such protocols described below. Use of such protocols and algae strains produced by such protocols can not only increase productivity and longevity of algal cultures in real photobioreactor systems, thereby reducing capital and operating costs, but also can reduce operating costs by eliminating the need to sterilize and environmentally isolate the photobioreactor system prior to and during operation, respectively.

Typically, commercially available algal cultures are adapted to be grown under ordinary laboratory conditions. Accordingly, such commercially available algal cultures are typically not able or well-suited to be grown under one or more conditions of light exposure, gas composition, temperature fluctuation, etc. to which algae would be expected to be exposed in the field in a gas-treatment photobioreactor system, such as described above. For example, most commercially available algal cultures are conditioned for growth at relatively low light levels, such as 150 micro Einstein per meter squared per second (150 $\mu Em^{-2}s^{-1}$). Exposure of such cultures to sunlight in photobioreactor gas-treatment systems of the invention—which may expose the organisms to light intensities of 2,500 $\mu Em^{-2}s^{-1}$ or greater—will typically cause substantial photoinhibition rendering such cultures unable to survive and/or grow adequately, and, therefore, unable to successfully compete with deleterious native species that may infiltrate the photobioreactor. Accordingly, as described in more detail below, one aspect of the inventive adaptation processes is to precondition and adapt such commercially available laboratory cultures to light of an intensity and duration expected to be experienced in full-scale photobioreactors of the invention.

In addition, as described above, the inventive photobioreactors, in certain embodiments, may be configured and operated to subject the algae to relatively high frequency photomodulation cycles. While such high-frequency photomodulation can be beneficial for the grown of the algae, unadapted and unconditioned algal strains may not be well adapted to and ideally suited for growing under such conditions. Accordingly, in certain embodiments, the inventive adaptation methods are able to produce algal strains that are adapted to and well-suited for growing under conditions of high-frequency photomodulation (e.g., light/dark interval switching frequencies of one per minute, one per second, one per $\frac{1}{10}$ second, one per $\frac{1}{100}$ second, one per millisecond, or higher). Similarly, many components found in typical industrial effluent gases, such as flue gases, which are desirably removed by the photobioreactors of the current invention in certain embodiments, may be lethally toxic to and/or can substantially inhibit growth of nonadapted algal strains at concentrations that may be found in such gases. For example, the concentration of $CO_2$, $NO_X$, $SO_X$, and heavy metals such as Hg in flue gases may be substantially higher than those that are toxic or deleterious to many unadapted algal strains.

Figure 10A:
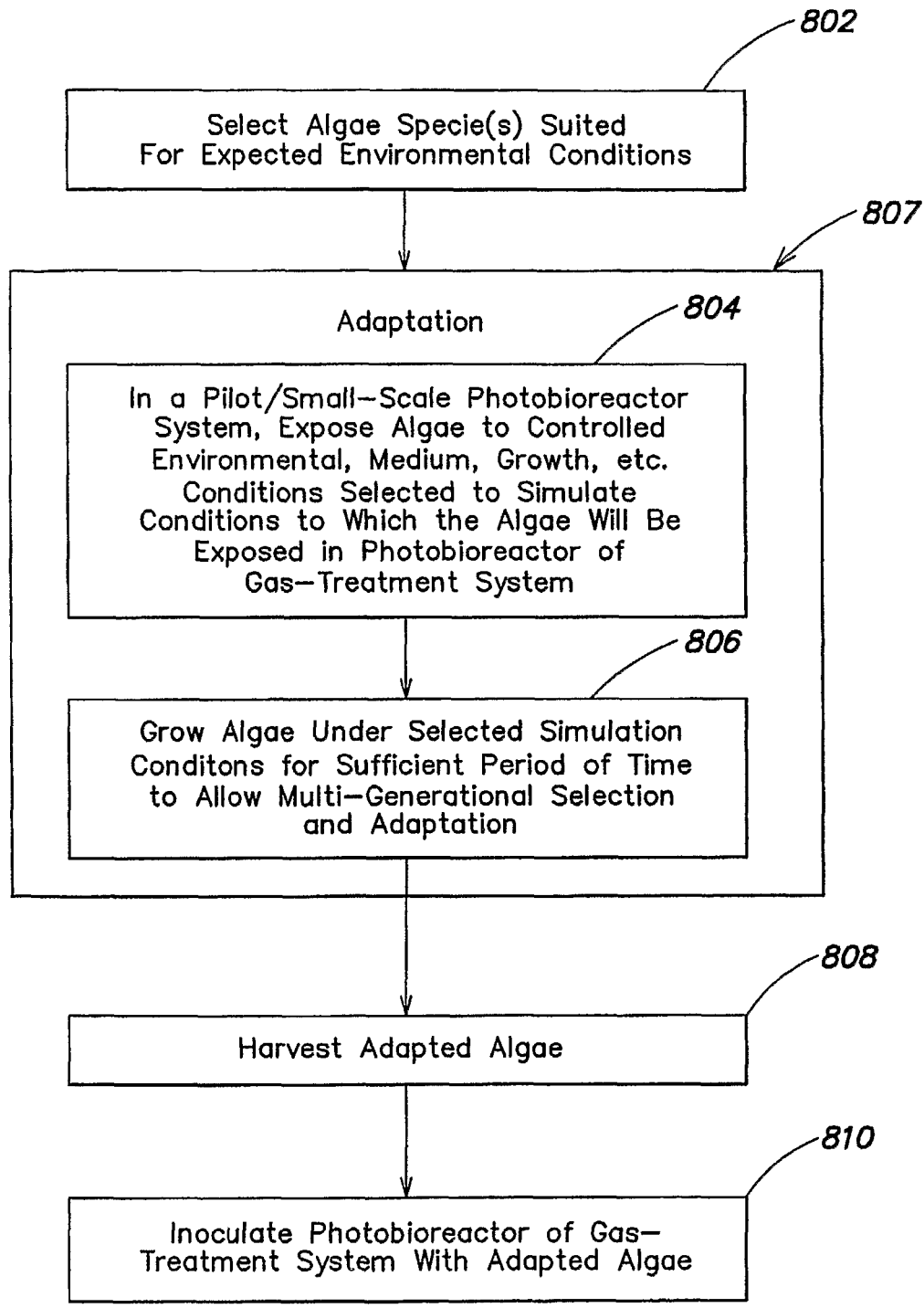
FIG. 10A is a block flow diagram illustrating one embodiment of a method for pre-conditioning an algal culture, according to one embodiment of the invention.

Certain exemplary embodiments of such algal adaptation and pre-conditioning methods are illustrated in FIGS. 10A-10D. Referring to FIG. 10A, initially, in step 802, one or more algae species are selected which are expected to be at least compatible with, and preferably well suited for, the expected environmental conditions at the particular photobioreactor installation site. In step 804, in a pilot-scale or a micro-scale photobioreactor system, an algal culture comprising the algae species from step 802 is exposed to a set of defined environmental, medium, growth, etc. conditions that are specifically selected to simulate conditions to which the algae will be exposed in the photobioreactor during operation, e.g., as part of a gas treatment system. In step 806, the algal cultures are grown and propagated under the selected simulation conditions for a sufficient period of time to allow for multi-generational natural selection and adaptation to occur. Depending on the algal species, this period may be anywhere from a few days to a few weeks to as much as a few months. At the end of adaptation, the adapted algae is harvested in step 808 and provided to an operator of a photobioreactor system, so that the photobioreactor may be inoculated with the algae to seed the photobioreactor.

Figure 10B:
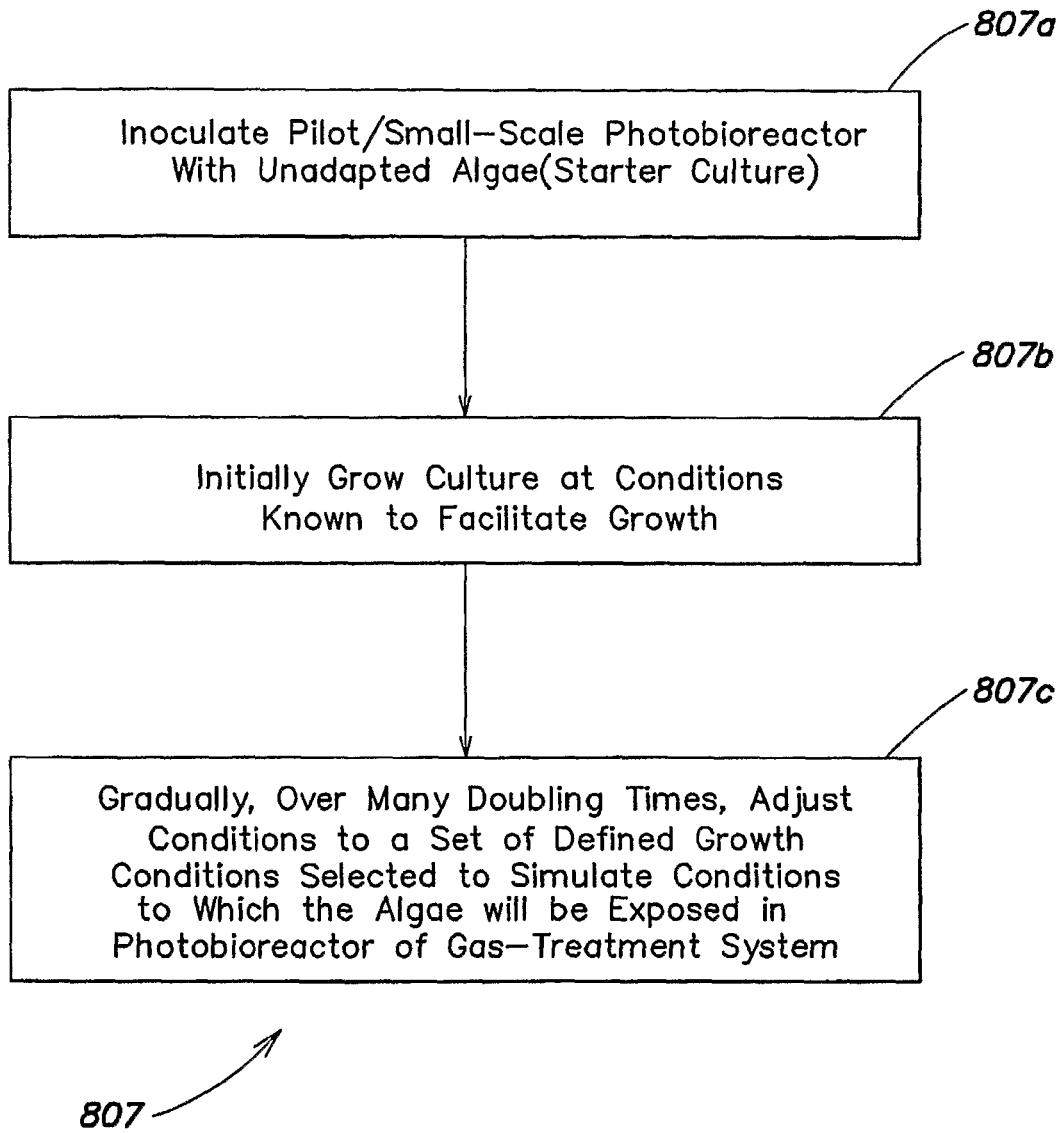
FIG. 10B is a block flow diagram illustrating one embodiment of a method for performing step 807 of FIG. 10A.

In certain embodiments, steps 804 and 806 illustrated in FIG. 10A, which together comprise adaptation step 807, are performed according to a protocol such as that illustrated in FIG. 10B. Referring to FIG. 10B, after the selecting step 802, a pilot or small-scale photobioreactor, such as those described in more detail below, is inoculated in step 807a with an unadapted (starter) algal culture. Then, initially, in step 807b, the culture is grown under conditions that are known to facilitate normal growth for the particular algal culture until the culture is fully established and growing well. Then, in step 807c, gradually, for example over a period of time equal to many doubling times of the algal culture (i.e., many generations of growth) the initial conditions are adjusted to a set of defined growth conditions that are selected to simulate conditions to which the algae will be exposed in a full-scale photobioreactor of a gas treatment system.

In certain embodiments, in step 807c, the rate and amount of adjustment of particular growth conditions is selected to be gradual enough to permit the culture to continue to grow during the entirety of the adaptation process. In certain embodiments, changes may occur for one or a few process conditions at a time, so that the algal culture becomes adapted to one or a subset of defined growth conditions simulating operating conditions in the gas treatment system before being adapted to others (i.e., the adaptation to particular growth conditions occurs non-simultaneously). In other embodiments, each of the growth conditions that are different for the defined set of growth conditions simulating actual operating conditions of the photobioreactor, as compared to the initial growth conditions of step 807b, are gradually adjusted simultaneously over the selected period of time. As mentioned above, in preferred embodiments, the gradual adjustment of growth conditions in step 807c occurs over many generations and doubling times of the culture, and, at least, should exceed one doubling time of the starter culture. For example, in certain embodiments, the overall length of the period over which growth conditions are adjusted in step 807c can exceed two doubling times, five doubling times, ten doubling times, 100 doubling times, 200 doubling times, or 500 doubling times of the starter culture grown under conditions as outlined in step 807b.

As discussed above, and as illustrated and discussed below in the context of FIG. 10C, the gradual adjustment step 807c may be effected to facilitate adjustment of initial growth conditions to the defined growth conditions simulating photobioreactor gas-treatment system operation in a variety of ways. The particular manner and sequence of adjustment may vary substantially depending upon the particular nature, sensitivity, adaptability, etc., of the starter culture and the particular algal strains chosen. Those of ordinary skill in the art, given the teachings and information provided herein, can readily determine a suitable or optimal course of gradual parameter adjustment to effect a desirable level of adaptation of any selected algal strain/culture using no more than ordinary skill and routine experimentation and optimization.

Figure 10C:
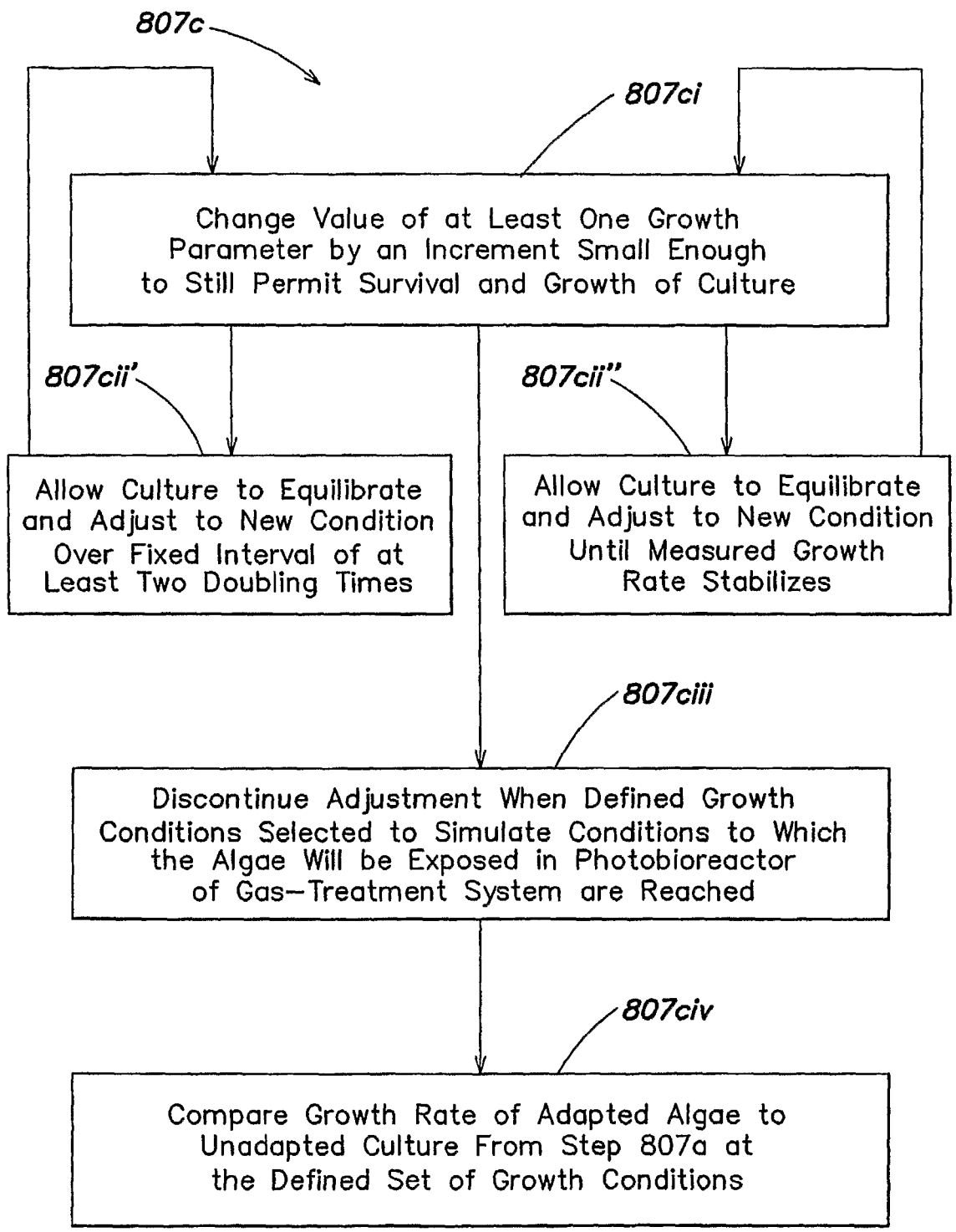
FIG. 10C is a block flow diagram illustrating one embodiment of a method for performing step 807c of FIG. 10B.

FIG. 10C illustrates certain exemplary embodiments for performing step 807c of FIG. 10B. Referring to FIG. 10C, a gradual parameter adjustment protocol is outlined that entails changing parameter values, either simultaneously or sequentially, or a combination thereof, over the adjustment period in a series of small increments. In certain embodiments, the increments may be evenly spaced and/or of equal magnitude. In alternative embodiments, depending on the particular parameters being adjusted and their effect on the growth of culture, the increments may be unequally spaced over the entire interval and/or be of unequal magnitude at different intervals over the period.

In step 807ci, the value of at least one growth parameter is changed by an increment that is selected to be small enough to still permit survival and growth of the culture after the change. In one embodiment, represented by step 807cii', the culture is then allowed to equilibrate and adjust to the new condition over a fixed interval of time selected to be sufficient to permit the growth rate to stabilize and recover. For example, such fixed interval of time may be at least two doubling times of the starter culture under the initial conditions, or greater. In other embodiments, especially for those in which the pilot/small-scale photobioreactor system utilized for adaptation includes the capability of automated growth rate determination of the culture, adjustment can be made as described in step 807cii'''. In such embodiment, after incrementally changing the value of the growth parameter, the culture is allowed to equilibrate and adjust to the new growth condition until a measured growth rate is determined to reach a stable plateau, before performing a subsequent incremental change. After waiting the requisite period of time described in step 807cii' or 807cii''', another incremental change to the same and/or different growth parameter is made, and the process is repeated until the growth parameters have been completely adjusted to the defined growth conditions selected to simulate conditions to which the algae will be exposed in the photobioreactor of the gas treatment system (step 807ciii). At this point, the adapted algal cultures can be continued to be cultured at the defined growth conditions for a period of time selected to be great enough to allow the growth rate to stabilize and to permit the cultures to become optimally suited to the defined simulation conditions. Typically, the adapted culture will be grown and maintained at the defined growth conditions indefinitely and until some sample of the adapted algae is harvested for inoculation into a photobioreactor of a gas-treatment system (steps 808 and 810 of FIG. 10A).

Referring again to FIG. 10C, after the adaptation process is complete, the effectiveness of the adaptation process can be determined in step 807civ by comparing the growth rate of the adapted algae to that of an equivalent unadapted culture (e.g., a sample of starter culture from step 807a of FIG. 10B) at the defined set of growth conditions selected to simulate conditions of operation of a photobioreactor in a gas-treatment system. In certain embodiments, the culture, when adapted, is able to grow under the defined set of conditions with a doubling time that is no greater than 50% that of an unadapted sample (i.e., twice the growth rate). In certain embodiments, the culture, when adapted, may be able to grow at the defined set of conditions with a doubling time that is no greater than 33%, 30%, 25%, 20%, 15%, 10% or less that of an unadapted sample of the starter culture subjected to the defined set of conditions.

As mentioned above, one growth parameter that may be very different in the photobioreactors of a gas-treatment systems of the invention during operation from that to which typical, commercially-available algal cultures are accustomed is light exposure, i.e., intensity and photomodulation frequency. For example, illuminance (or photon flux density) in full sunlight, such as may be experienced by cultures growing in photobioreactors that are part of gas-treatment systems of the invention, can be 2500 $\mu Em^{-2}s^{-1}$ or more. Typical laboratory prepared cultures of algae are typically grown under conditions of much lower light intensity, e.g., 150 $\mu Em^{-2}s^{-1}$ or less. In such commercially available cultures, a reduction in the growth rate of such cultures via photoinhibition may occur, depending on the particular algal species, at levels of about, for example, 300 $\mu Em^{-2}s^{-1}$. Accordingly, such commercially available cultures are poorly suited for, and may experience high levels of photoinhibition and poor growth or cell death, under conditions expected to be experienced by algal cultures in operation in the inventive photobioreactor of gas-treatment systems. Additionally, as mentioned above, commercially-available algal cultures may not be accustomed to photomodulation at high frequency.

In order to adapt algal cultures to higher illumination intensities, such as those that may be experienced in the inventive photobioreactors in full sunlight, in certain embodiments, prior to initiating photomodulation, a starter culture is gradually adapted, as described in FIGS. 10A-10C above, to illumination intensities that are above the intensity that is known to be capable of causing a reduction in the growth rate of the starter culture via photoinhibition. "Known to be capable of causing reduction in the growth rate of the starter culture via a photoinhibition" refers herein to such an intensity being known for unadapted cultures/samples either through values available in the published literature for such cultures or through routine screening tests to define a photoinhibition threshold. Once the culture has become adapted to growth at a light intensity above the known photoinhibition threshold, then, as described in more detail below, in the presently described embodiment, adaptation to higher frequency photomodulation may be commenced. In certain embodiments, the algal culture may be adapted to the light intensity that is at least twice that known to be capable of causing a reduction in the growth rate of an unadapted starter sample of the culture, in other embodiments the intensity level to which the culture is adapted may be 3, 5, 10, 20, or more times that known to be capable of causing growth rate reduction via photoinhibition of the starter sample.

In certain embodiments, the algal culture is adapted to relatively high-frequency photomodulation cycles, simulating those that may be expected during operation of a photobioreactor in a gas-treatment system of the invention. A photomodulation cycle comprises a period of illumination at an intensity above a threshold able to drive photosynthesis in the culture and a period of exposure to a lower intensity below the threshold capable of driving photosynthesis of the organisms of the culture. The frequency of the cycle can be characterized by the number of transitions from high (light) to low (dark) illumination intensities per unit of time. In certain embodiments, the duration of light intervals and dark intervals over a given light/dark cycle may be the same or, in other embodiments, the light period may exceed the dark period or the dark period may exceed the light period. Accordingly, it is possible to adapt the algae to both photomodulation frequency and relative duration of light versus dark periods within a given light/dark cycle, according to the methods of the invention. In certain embodiments, the algal culture may be adapted and preconditioned for growth conditions that comprise a variation in light intensity to cause photomodulation at a light/dark cycling frequency of at least one light/dark transition per minute. In other embodiments, the algal culture may be conditioned for light/dark cycling frequencies of at least one light/dark transition per 30 seconds, per 10 seconds, per 5 seconds, per second, per ½ second, per 1/10 second, per 1/100 second, per millisecond, or greater.

In certain embodiments, it may be desirable to develop a preconditioned, adapted algae, according to the methods of the invention, that is preconditioned and adapted to grow and thrive under conditions of exposure to one or more typical pollutant gases, dissolved in the growth medium, that may be found in flue gas or other gases being treated by a gas treatment system in which the algal culture is intended to be used. In certain such embodiments, it may be desirable to adapt an algal culture to growth in a liquid medium that contains at least one of dissolved $CO_2$, $NO_x$, $SO_x$, and/or heavy metals, such as Hg. In certain embodiments, the algal culture is adapted to concentrations of such gases dissolved in the liquid medium that are typical of those that would be experienced when the algal culture is contained within a photobioreactor of a gas-treatment system of the invention that is fed a gas for treatment containing one or more of the above pollutant gases at concentrations typically found in flue gas, or other combustion gases that may be treated. Accordingly, in certain embodiments, an algal culture may be exposed to and adapted to a defined set of growth conditions that comprises growth of a culture in a liquid medium, wherein the liquid medium has been exposed in mass transfer communication with at least one of the above-mentioned substances.

A liquid medium that is exposed in "mass transfer communication" with a gas comprising at least one of the above-mentioned substances refers to such liquid medium being placed either in direct interfacial contact with such gas (e.g., as when the gas is sparged or bubbled into the liquid) or to the liquid medium being separated from the gas by a liquid impermeable membrane or layer through which one or more components of the gas or gas mixture is able to diffuse over a time scale allowing the dissolution of at least some of such diffusible components into the liquid medium. In certain embodiments, the liquid medium may be exposed in mass transfer communication with a gas under conditions sufficient to allow dissolution of soluble gas components in the liquid at amounts indicative of mass transfer equilibrium having been reached between the gas and the liquid at ambient conditions of the environment in which the mass transfer communication occurred (e.g. about 25° C. and atmospheric pressure at sea level in certain embodiments). In certain such embodiments, the gas to which the liquid medium is exposed in mass transfer communication can comprise an actual flue gas or a gas mixture simulating flue gas. In certain embodiments, the gas comprises at least about 5% wt $CO_2$, and in certain embodiments between about 8% wt $CO_2$ and about 15% wt $CO_2$. In certain embodiments, the gas comprises $NO_x$ in an amount of at least 1 ppm, in certain embodiments at least about 10 ppm, in certain embodiments at least about 100 ppm, and in certain embodiments between about 100 ppm and about 500 ppm. In certain embodiments, the gas comprises $SO_x$ in an amount of at least about 1 ppm, in other embodiments at least about 50 ppm, in other embodiments between about 50 ppm and about 1,000 ppm, and in other embodiments at least about 1,000 ppm.

While the presently disclosed adaptation methods are particularly well suited for adapting and preconditioning algal species to define growth conditions that are selected to simulate conditions in a photobioreactor of a gas treatment system of the invention, in other embodiments, other photosynthetic organisms, for example euglena may be similarly adapted and preconditioned. While essentially any algal species, species of other photosynthetic organisms, or collection of such species can potentially be adapted and preconditioned according to the methods disclosed herein, in certain embodiments, a preconditioned culture produced according to the invention will comprise at least one species of algae selected from the genuses *Chlorella, Spirolina, Chlamydomonas, Dunaliella, Chaetoceros*, and/or *Porphyridium*. In certain exemplary embodiments, a preconditioned culture produced according to the invention comprises at least one of *Dunaliella tertiolecta, Porphyridium* sp., *Dunaliella parva, Chlorella pyrenoidosa, Chaetoceros muelleri*, and/or *Chlamydomonas reinhardtii*.

In certain embodiments, the pilot-scale photobioreactor utilized in adaptation step 807 could be similar to or identical to those described above in the context of determining growth model constants for the growth/photomodulation mathematical model above. For example, a small volume, thin-film tubular photobioreactor as described in Wu and Merchuk, 2001 could be utilized.

In certain embodiments, step 807 is carried out and performed utilizing an existing or custom-developed automated cell culture and testing system, in certain embodiments utilizing a plurality of precisely controllable small-scale bioreactors, which can be operated as photobioreactors, thus allowing for precise, simultaneous multi-parameter manipulation and optimization of algal cultures with the system. An "automated cell culture and testing system" as used herein, refers to a device or apparatus providing at least one bioreactor and which provides the ability to control and monitor at least one, and preferably a plurality of, environmental and operating parameters. Certain embodiments employ systems that are automated cell culture and testing systems having at least one, and more preferably a plurality of, bioreactors providing photobioreactors having a culture volume of between about 1 microliter and about 1 liter, between about 0.5 ml and about 100 ml, or between about 1 ml and about 50 ml. Potentially suitable, as provided or after suitable modifications, automated cell culture and testing systems are available and are described, for example, in (Vunjak-Novakovic, G., de Luis J., Searby N., Freed L. E. Microgravity Studies of Cells and Tissues. *Ann. NY Academy of Sciences*; Vol. 974, pp. 504-517 (2002); Searby N. D., J. Vandendriesche, L. Sun, L. Kundakovic, C. Preda, I. Berzin and G. Vunjak-Novakovic (2001) Space Life Support From the Cellular Perspective, *ICES Proceeding* 01ICES-331 (2001); de Luis, J., Vunjak- Novakovic, G., and Searby N. D. Design and Testing of the ISS Cell Culture Unit. *Proc. 51st Congress of the Astronautical Federation*, Rio de Janeiro, Oct. 2-6, 2000; Searby N. D., de Luis, J., and Vunjak-Novakovic, G. Design and Development of a Space Station Cell Culture Unit. *J. Aerospace*, Vol. 107, pp. 445-457 (1998); and U.S. Pat. No. 5,424,209; U.S. Pat. No. 5,612,188; U.S. Patent Application Publication 2003/0040104; U.S. Patent Application 2002/0146817; and International Application Publication no. WO 01/68257, each of the above patents, published applications, and literature references are incorporated herein by reference).

In certain configurations, such an automated cell culture and testing system includes computer process control and monitoring enabling growth conditions such as temperature, light exposure intervals and frequency, nutrient levels, nutrient flow and mixing, etc. to be monitored and adjusted. Certain embodiments can also provide on-line video microscopy and automatic sampling capability. Such automated cell culture and testing systems can allow multidimensional adaptation and optimization of the algal system by enabling control of a variety of growth parameters, autonomously.

In one particular embodiment, an automated cell culture and testing system, as described above, is configured to expose the algal cultures to expected conditions of: liquid medium composition; liquid medium temperature; liquid medium temperature fluctuation magnitude, frequency and interval; pH; pH fluctuation; light intensity; light intensity variation; light and dark exposure durations and light/dark transition frequency and pattern; feed gas composition; feed gas composition fluctuation; feed gas temperature; feed gas temperature fluctuation; and others; and to carry out the above-described culture adaptation protocols.

In one exemplary embodiment, high frequency light/dark cycles simulating photomodulation created by turbulent eddies and/or recirculation vortices in a light exposed part of the photobioreactor are simulated utilizing a light source shining on a micro-photobioreactor of an automated cell culture and testing system through a variable-speed chopper wheel with interchangeable disks machined with slits, or otherwise provided with opaque and transparent regions, to give appropriate frequencies of photomodulation and ratio of light/dark periods. In one example, photomodulation light/dark interval frequencies of 0.1, 0.5, 1, 10, 100, and 1000 cycles per second are simulated. As described above, each adaptation step 807 should occur over a long enough period to allow for multi-generational adaptation. In a particular embodiment in which an algae species of *Dunaliella* is pre-adapted, each adaptation increment (FIG. 10C) is allowed to occur over at least a 1-, 2-, or 3-day cycle to allow a multi-generational adaptation.

FIGS. 10D-10G illustrate various components of an exemplary embodiment of an automated cell culture and testing system that can be utilized to perform the above-described cell culture adaptation and preconditioning methods. It should be emphasized that the particular example of a cell culture system illustrated in FIG. 10D comprises only one of a very wide variety of possible configurations and set ups. As would be understood by those of ordinary skill of the art, a wide variety of perfusion and non-perfusion based cell culture systems, including small-scale cell culture systems, can potentially be adapted to be used within the context of the invention. Accordingly, the particular system and components described herein are purely exemplary and may be otherwise configured, substituted, or eliminated in other embodiments within the scope of the invention defined by the claims appended below. The exemplary embodiment illustrated in FIGS. 10D-10G comprises a modified and adapted cell culture system similar to that described in: Vunjak-Novakovic, G., de Luis J., Searby N., Freed L. E. Microgravity Studies of Cells and Tissues. *Ann. NY Academy of Sciences*; Vol. 974, pp. 504-517 (2002); Searby N. D., J. Vandendriesche, L. Sun, L. Kundakovic, C. Preda, I. Berzin and G. Vunjak-Novakovic (2001) Space Life Support From the Cellular Perspective, *ICES Proceeding* 01*ICES*-331 (2001); de Luis, J., Vunjak-Novakovic, G., and Searby N. D. Design and Testing of the ISS Cell Culture Unit. *Proc. 51st Congress of the Astronautical Federation*, Rio de Janeiro, Oct. 2-6, 2000; Searby N. D., de Luis, J., and Vunjak-Novakovic, G. Design and Development of a Space Station Cell Culture Unit. *J. Aerospace*, Vol. 107, pp. 445-457 (1998), to which the readers refer for additional details.

Figure 10D:
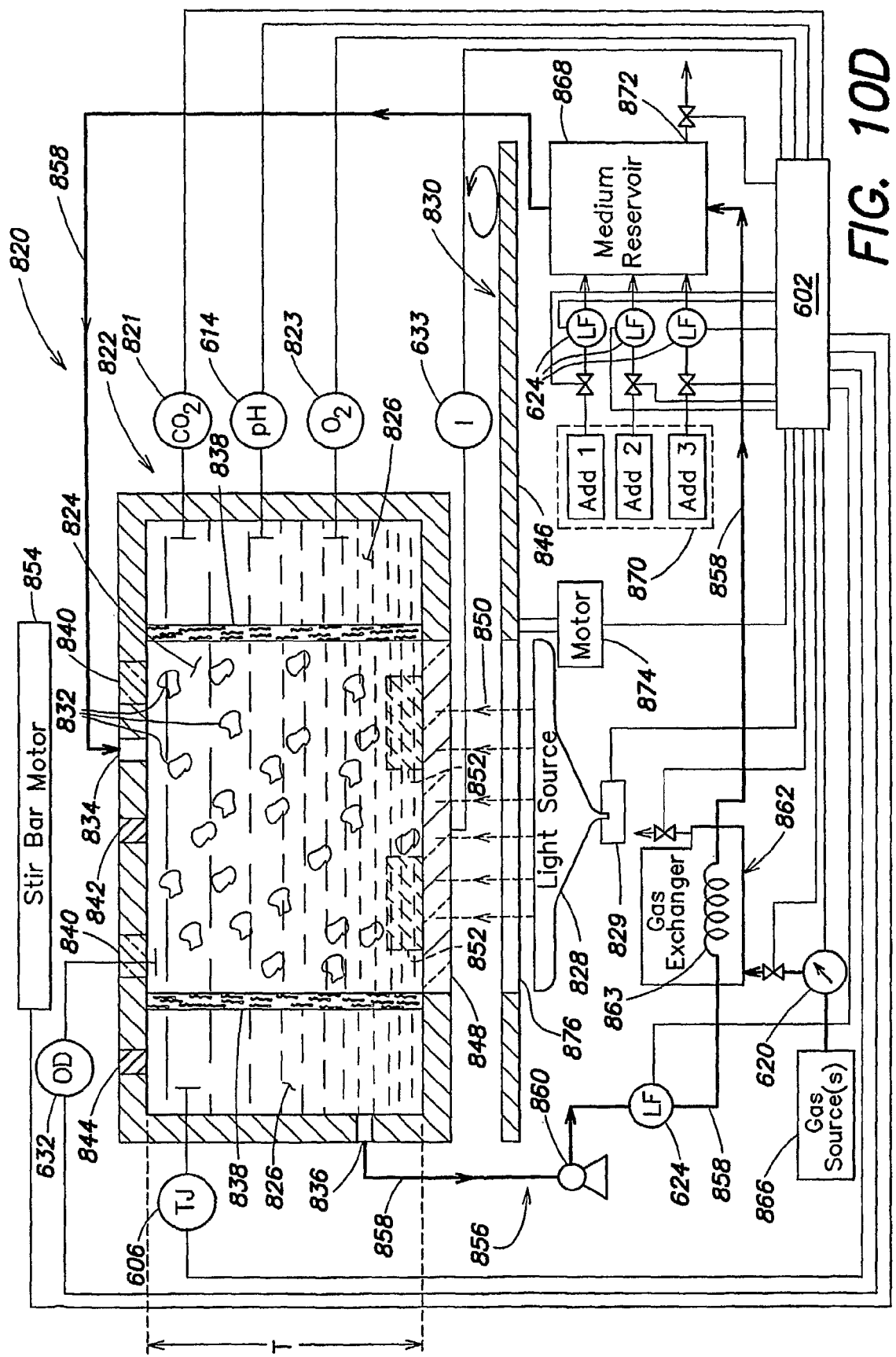
FIG. 10D is a schematic process flow diagram of one embodiment of an automated cell culture adaptation system.
Figure 10E:
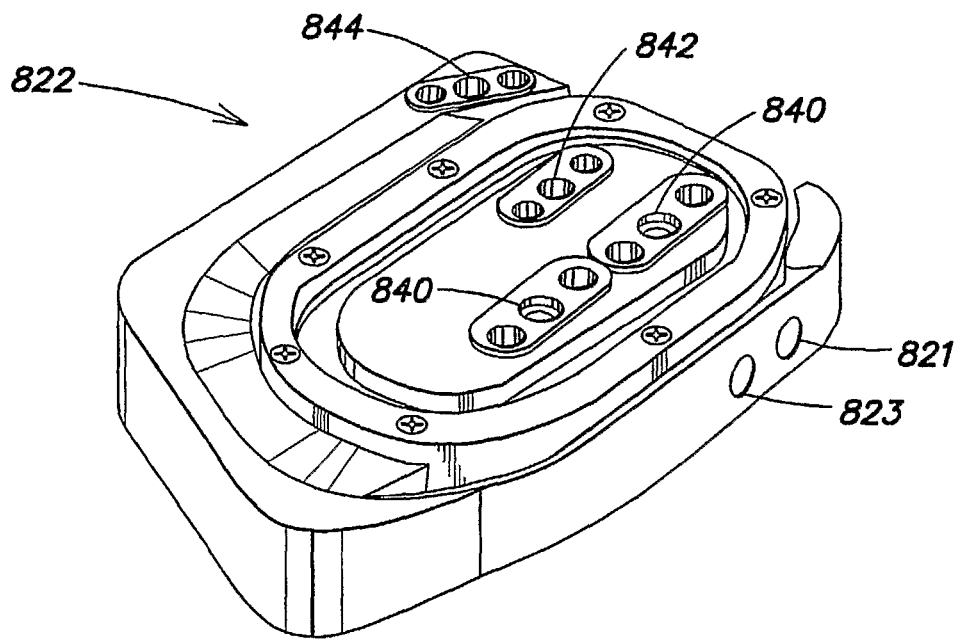
FIG. 10E is a perspective view from the top of one embodiment of a cell culture module of FIG. 10D.
Figure 10F:
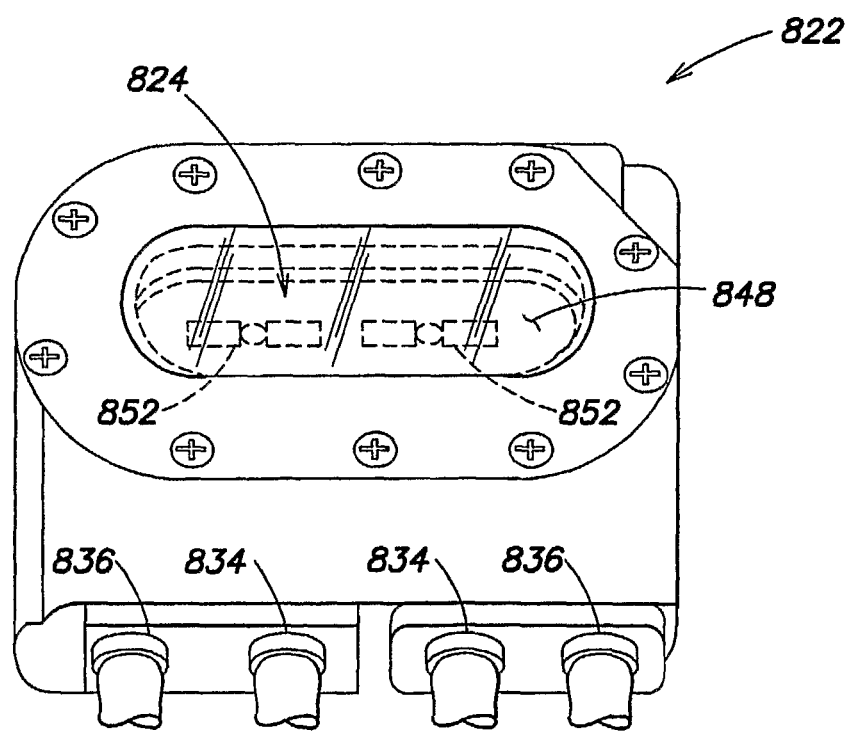
FIG. 10F is a perspective view from the bottom the cell culture module of FIG. 10E.
Figure 10G:
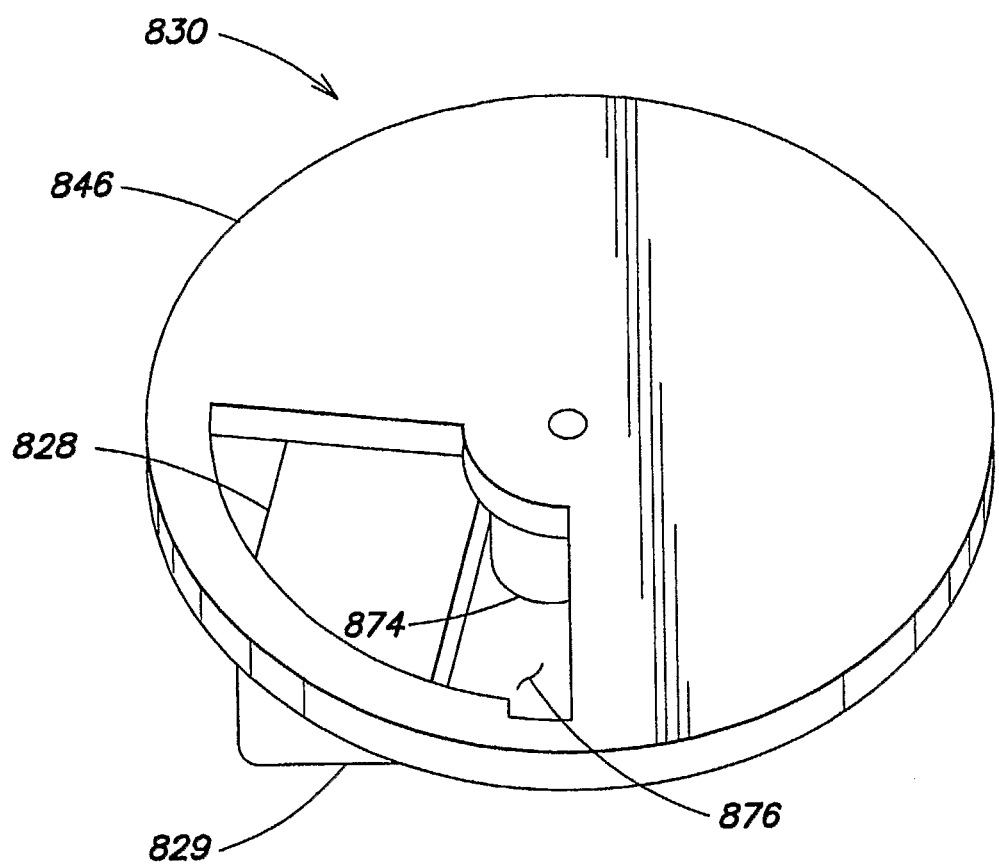
FIG. 10G is a schematic plan view of one embodiment of a chopper wheel that forms part of the light source modulator of FIG. 10D.

Referring to FIG. 10D an automated cell culture and testing system 820 is schematically illustrated comprising a perfusion-based cell culture system including a cell culture module 822 including therein a cell cultured chamber 824 and medium containing cell-free region 826. The configuration of cell culture module 822 is described in more detail in the above-mentioned references and is illustrated in greater detail in FIGS. 10E and 10F. In certain embodiments, the cell culture module 822 comprises a small-scale bioreactor having an internal volume between about 1 micro liter, in certain embodiments between about 0.5 ml and about 50 ml, and in certain embodiments between about 1 ml and about 10 ml. As is described in more detail below, automated cell culture and testing system 820 further comprises an adjustable source of artificial light 828 capable of driving photosynthesis and a light source modulator 830 that is constructed and arranged to vary the intensity of the light that reaches the algal cells 832 in cell culture chamber 824 between a first (light) intensity and a second (dark) intensity, preferably at a frequency of at least one variation per second, and in certain embodiments at frequencies mentioned above with regard to adaptation to defined levels of photomodulation simulating actual conditions of photobioreactors of the gas treatment systems of the invention.

In the illustrated exemplary embodiment, cell culture system 820 is configured as a perfusion-based system, and cell culture module 822 includes at least one liquid medium inlet 834 and at least one liquid medium outlet 836 interconnected in a flow loop described in more detail below, whereby liquid medium is continuously or intermittently removed from cell culture module 822, treated to effect maintenance or variation of various cell culture parameters, and returned to cell culture module 822. In alternative embodiments, cell culture module 822 and cell culture system 820 may be configured as a non-perfusion system in which adjustments in various cell culture parameters are effected upon the liquid medium while it remains contained in the cell culture module. Such non-perfusion systems are well know and may be substituted for the perfusion-based system illustrated and described herein.

Automated cell culture system 820 includes, in certain embodiments, a plurality of different sensors, actuators, valves, flow meters, etc., for measuring, maintaining, and/or adjusting/changing various cell culture parameters to provide defined growth conditions in order to effect various culture adaptation protocols according to the invention. Such components may comprise a variety of sensors, flow meters, etc., similar to those described above in the context of FIG. 7A, and the system can further comprise a computer-implemented control system 602, that can be essentially the same as or similar to that described above in the context of FIG. 7A. In certain embodiments, wherein the cell culture module 822 comprises a small-scale bioreactor, sensors provided to monitor liquid medium conditions within cell culture module 822, for example pH sensor 614, CO$_2$ sensor 821, and oxygen sensor 823, may be configured as optical chemical sensors (e.g. such as those based on fluorescence modulation), which are well known in the art as being particularly well suited for non-invasive parameter measurement of small volume systems (see, e.g., U.S. Pat. Nos. 6,673,532; 6,285,807; 6,051,437; 5,628,311; 5,606,170; and 4,577,110, each incorporated herein by reference).

In the system illustrated FIG. 10D, the interior of cell culture module 822 is partitioned by an optional cell retaining membrane(s) 838, which divide the interior of cell culture module 822 into a cell culture chamber 824, including suspended algae 832, and cell-free volume 826 containing liquid medium. Membranes 838 can be formed of any of a wide variety of biocompatible materials, which are well known to those of ordinary skill in the art, and preferably have a permeability and pore size selected to allow the liquid medium and components dissolved therein to permeate freely through the membranes while retaining in cell culture chamber 824 algal cells 832. In alternative embodiments, in which it is not unacceptable or deleterious to circulate cells around the profusion loop of the cell culture system, membranes 838 may be eliminated.

Cell culture module 822, as illustrated, further includes a top surface having two small optically transparent windows 840 therein providing visual access to culture chamber 824, for example, to allow visual observation, video monitoring, illumination of the culture chamber, etc. In addition, cell culture module 822 includes a cell sampling septum 842 and a cell-free sample septum 844 to facilitate the ability to insert and withdraw samples to and from cell culture chamber 824 and cell-free volume 826, in certain embodiments in a sterile manner, respectively. Cell sampling septum 842 may also be used to remove cells from culture chamber 824 for the purpose of diluting the culture with cell free-medium when cell density exceeds a certain value. Such dilution/subculturing may be performed manually or automatically by an automated sampling station (not shown) under the control of computer-implemented control system 602.

The bottom surface of cell culture module 822, which is positioned in spaced-apart relationship from light cutter wheel 846 of light source modulator 830 and light source 828, includes a region 848 comprising an optical window that is at least partially transparent to light of a wavelength capable of driving photosynthesis. As explained in greater detail below, in the illustrated embodiment, light source 828 is configured and positioned to direct light 850 so that it is incident upon transparent region 848 of cell culture module 822, thereby permitting the light to entered cell culture chamber 824 to illuminate the culture and drive photosynthesis and growth. In certain embodiments, light source 828 comprises a full-spectrum illuminator, which has an intensity that can be adjusted by, for example, modulating the power to the light source (e.g. under the control of computer-implemented system 602), varying the distance from the light source to the optically transparent region 848 of the cell culture module 822, etc. In certain embodiments, light source 828 can comprise one or more incandescent lamps, fluorescent lamps, LEDs, lasers, or other known light source. In certain embodiments, other than that illustrated in FIG. 10D, cell culture module 822 may not include an optically transparent region 848 but, rather, may include a light source that is located directly within culture chamber 824. In certain such embodiments, and/or in alternative embodiments having a light source 828 positioned externally of culture chamber 824, that utilizes a light source modulator not including the illustrated cutter wheel mechanism 846 for high frequency modulation of light intensity and provision of photo modulation, high frequency photo modulation could be effected by for example, controllable rapid on/off switching of the power supply 829 to light source 828, for example, with an electric pulse generator, strobe circuit, etc.

In certain embodiments, in order to ensure that the contents of culture chamber 824 are well mixed so that algal cells 832 contained within the culture chamber are exposed to essentially uniform light intensity throughout the chamber (i.e. to reduce the effects of any photo modulation due to flow patterns within culture chamber 824), culture chamber 824 can include therein one or more magnetic stirring devices such as magnetic stir bars 852 that can be driven in rotation by a stir bar motor 854. In addition, it may be desirable to configure cell culture module 822 so that it has a thickness (T) that is small enough to ensure that algae cell located it any vertical position within culture chamber 822 are subjected to a light intensity that is substantially similar to cells located in any other position within the culture chamber.

As illustrated, automated cell culture system 820 includes a single cell culture module 822 and perfusion loop 856 associated therewith. However, in certain embodiments, cell culture system 820 may be made part of a larger, multi-module, automated cell culture system comprising a plurality of cell culture modules and associated perfusion loops configured in parallel. Such a multi-module system could permit simultaneous adaptation of multiple algal cultures to a plurality of different sets of defined culture parameters.

Perfusion loop 856, in certain embodiments, comprises flexible tubing 858 for medium recirculation, which has low gas permeability. A variety of suitable materials for forming such tubing are well known to those of ordinary skill in art and include, for example, polymeric tubing made out of one or more suitable polymers such as, for example, poly(vinyl chloride), polyethylene, polypropylene, etc. A pump 860, for example a peristaltic pump, may be used for circulation and may be controlled via computer implemented system 602 to provide a desirable liquid medium flow rate, for example as measured by flow meter 624. In certain embodiments, the computer-implemented control system 602 can be provided with the capability to, provide periodic flow, provide for reverse flow, unsteady flow, etc.

Perfusion loop 856 can further comprise a gas exchanger 862 that is constructed and arranged to provide mass transfer communication between the liquid medium and gas comprising at least one component dissolvable in the liquid medium. In the illustrated embodiment, gas exchanger 862 comprises a silicone-coil gas exchanger in which liquid medium passes through a selected length of coiled silicone tubing 863, having high permeability for one or more dissolvable gas species, such as O$_2$, CO$_2$, NO$_x$, SO$_x$, etc. As would be understood by those of ordinary skill in the art, the particular degree of gas permeation and mass transfer into the liquid medium in gas exchanger 862 depends upon a variety of design factors well known to those of ordinary skill in the chemical engineering arts; such as, for example, the permeability of tubing 864 for the particular species, the length of tubing 863, the flow rate of liquid medium through the tubing, the temperature, the pressure of gas within gas exchanger 862, the composition and concentration of dissolvable components within the gas within gas exchanger 862, etc. Appropriate values of the above parameters that can provide a desirable level of mass transfer and dissolution of dissolvable gas species in the liquid medium for a given pass through gas exchanger 862 can be readily determined by those of ordinary skill in the chemical engineering arts. Gas exchanger 862 is connected in fluid communication with a gas source 866, which can comprise, in certain embodiments, flue gas or a gas mixture simulating flue gas and/or a defined gas mixture containing one or more components dissolvable in the liquid medium to which exposure it is desired to adapt algal cells 832. Such components and there concentrations have been discussed previously in the context of the inventive culture adaptation protocols.

In alternative embodiments, the silicone-coil gas exchanger 862 illustrated may be supplemented or replaced by a wide variety of other gas exchangers of known design. For example, in certain embodiments, the gas exchanger could comprise a stacked membrane or hollow fiber membrane type gas exchanger. In yet other embodiments, the gas exchanger could comprise a vessel containing the liquid medium into which gas is sparged, similar to the gas exchange systems utilized in photobioreactor apparatus 100 illustrated and discussed previously. In yet other embodiments, especially in embodiments wherein the cell culture system is a non perfusion-based system not comprising a perfusion loop, a gas exchanger could comprise one or more external surfaces of such cell culture module being formed of a gas permeable, liquid impermeable membrane. In such an embodiment, the entire cell culture module could be contained within an enclosure providing a surrounding gaseous environment comprising a gas including one or more components dissolvable in the liquid media that are desired to be added to the liquid media for adaptation of the cell culture.

As illustrated, perfusion loop 856 of automated cell culture system 820 further includes a liquid medium reservoir 868 connected in liquid communication with one or more sources 870, of fresh medium or other additives for adjustment of the composition of the liquid medium in cell culture module 822. Cell culture medium reservoir 868 may also comprise a medium outlet 872 from which spent medium may be removed, samples extracted, etc.

Light source modulator 830 in the embodiment illustrated in FIG. 10D comprises a rotating cutter wheel 846 (see FIG. 10G) driven in rotation by a variable speed motor 874, which is controlled by computer implemented system 602. Cutter wheel 846 can be made from a material that is optically opaque to light of a wavelength capable of driving photosynthesis and can include in spaced apart location(s) at one or more angular positions on the disk optically transparent region(s) 876, which are at least partially transparent to light of wavelength capable of driving photosynthesis (see FIG. 10G). In one embodiment, cutter disk 846 is formed of an opaque medal having a plurality of slits therein comprising transparent regions 876. In other embodiments, cutter disk 846 could be made of an opaque material not having slits therein, but rather having regions of the material that have been rendered transparent to light of a wavelength capable driving photosynthesis. In alternative embodiments, cutter disk 846 can be made of a material that is transparent to light of a wavelength capable of driving photosynthesis and made to include thereon regions comprising an opaque coating, dye, etc. to provide an essentially equivalent effect as the illustrated cutter disk 846. In certain embodiments, transparent regions 876 of cutter disk 846 need not be completely transparent to light of a wavelength capable of driving photosynthesis, but, rather, could comprise regions of partial transparency and/or could comprise wavelength-selective optical filters, polarizers, etc. The light/dark cycle frequency and light and dark time interval duration can be controlled, in certain embodiments, via either or both of: (1) the number, position, and size of optically transparent region(s) 876 on the cutter wheel, and (2) the rotational speed of the cutter wheel, which is dictated by variable speed motor 874.

Figure 11:
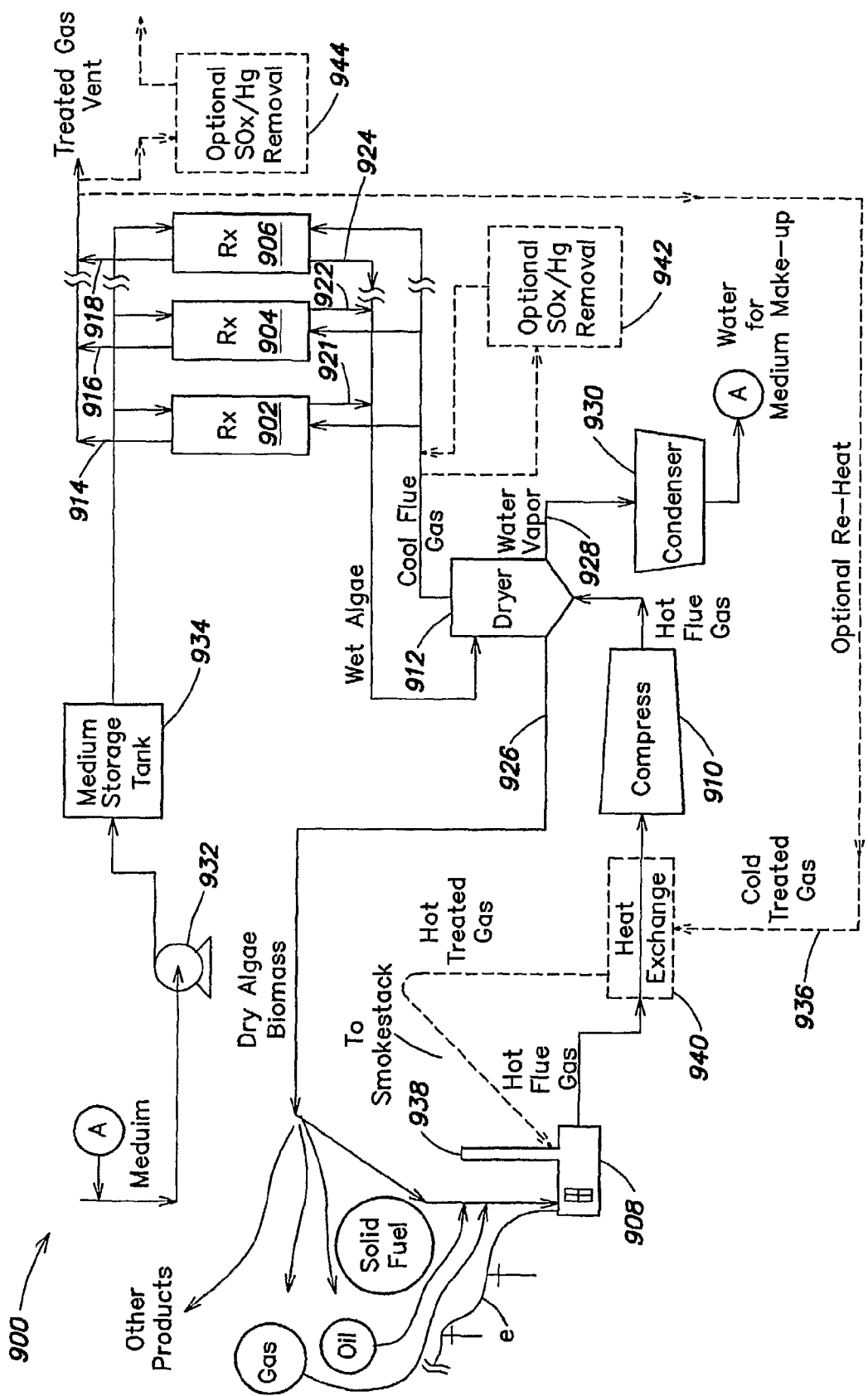
FIG. 11 is a schematic process flow diagram of one embodiment of an integrated combustion method, according to one embodiment of the invention.

FIG. 11 illustrates one embodiment of an integrated system for performing an integrated combustion method, wherein combustion gases are treated with a photobioreactor system to mitigate pollutants and to produce biomass, for example in the form of harvested algae, with the photobioreactor system, which can be utilized as a fuel for the combustion device and/or for the production of other products, such as products comprising organic molecules (e.g. fuel grade oil (e.g. biodiesel) and/or organic polymers). Integrated system 900 can be advantageously utilized to both reduce the level of pollutants emitted from a combustion facility into the atmosphere and, in certain embodiments, to reduce the amount of fossil fuels, such as coal, oil, natural gas, etc., burned by the facility and/or to produce a non-fossil, clean fuel, such as hydrogen, from the biomass. Such a system can potentially be advantageously utilized for treating gases emitted by facilities such as fossil fuel (e.g., coal, oil, and natural gas)—fired power plants, industrial incineration facilities, industrial furnaces and heaters, internal combustion engines, etc. Integrated gas treatment/biomass-producing system 900 can, in certain embodiments, substantially reduce the overall fossil fuel requirements of a combustion facility, while, at the same time, substantially reducing the amount of $CO_2$ and/or $NO_x$ released as an environmental pollutant, and, in certain embodiments providing biomass useful in producing clean fuel products, such as hydrogen and biodiesel.

Integrated system 900 includes one or more photobioreactors or photobioreactor arrays 902, 904, and 906. In certain embodiments, these photobioreactors can be similar or identical in design and configuration to those previously-described in any of FIGS. 1A, 1B, 3A-3D, 5A-5E, 6A, 6B, and 7A. In alternative embodiments, other embodiments of the inventive photobioreactors could be utilized or conventional photobioreactors could be utilized. Except for embodiments wherein system 900 utilizes photobioreactors provided according to the present invention (in which the photobioreactors are inventive and not conventional), the unit operations illustrated in FIG. 11 can be of conventional designs, or of straightforward adaptations or extensions of conventional designs, and can be selected and designed by those of ordinary skill in the chemical engineering arts using routine engineering and design principles.

In the illustrated, exemplary system, hot flue gases produced by electrical generating power plant facility 908 are, optionally, compressed in a compressor 910 and passed through a heat exchanger comprising a dryer 912, the function of which is explained below. Heat exchanger 912 is configured and controllable to allow the hot flue gas to be cooled to a desired temperature for injection into the photobioreactor arrays 902, 904, and 906. The gas, upon passing through the photobioreactors is treated by the algae or other photosynthetic organisms therein to remove one or more pollutants therefrom, for example, $CO_2$ and/or $NO_x$. Treated gas, containing a lower concentration of $CO_2$ and/or $NO_x$ than the flue gas is released from gas outlets 914, 916, and 918 and, in one embodiment, vented to the atmosphere.

As described above, algae or other photosynthetic organisms contained within the photobioreactors can utilize the $CO_2$ of the flue gas stream for growth and reproduction thereby producing biomass. As described above, in order to maintain optimal levels of algae or other photosynthetic organisms within the photobioreactors, periodically biomass, for example in the form of wet algae, is removed from the photobioreactors through liquid medium outlet lines 921, 922, and 924.

From there, the wet algae is directed to dryer 912, which is fed with hot flue gas as described above. In the dryer, the hot flue gas can be utilized to vaporize at least a portion of the water component of the wet algae feed, thereby producing a dried algae biomass, which is removed via line 926. In certain embodiments, advantageously, dryer 912, in addition to drying the algae and cooling the flue gas stream prior to injection in the photobioreactors, also serves to humidify the flue gas stream, thereby reducing the level of particulates in the stream. Since particulates can potentially act as a pollutant to the photobioreactor and/or cause plugging of gas spargers within the photobioreactors, particulate removal prior to injection into the photobioreactors can be advantageous.

The water, or a portion thereof, removed from the wet algae stream fed to dryer 912 can be fed via line 928 to a condenser 930 to produce water that can be used for preparation of fresh photobioreactor liquid medium. In the illustrated embodiment, water recovered from condenser 930 (at "A"), after optional filtration to remove particulates accumulated in dryer 912, or other treatment to remove potential contaminants, can be pumped by a pump 932 to a medium storage tank 934, which feeds make up medium to the photobioreactors.

The dried algae biomass recovered from dryer 912 can be utilized directly as a solid fuel for use in a combustion device of facility 908 and/or could be converted into a fuel grade oil (e.g., "biodiesel") and/or a combustible organic fuel gas. In certain embodiments, at least a portion of the biomass, either dried or before drying, can be utilized for the production of products comprising organic molecules, such as fuel-grade oil (e.g. biodiesel) and/or organic polymers, therefrom. Algal biomass earmarked for fuel-grade oil (e.g. biodiesel) production, or fuel gas production or the like can be decomposed in a pyrolysis or other known gasification processes and/or a thermochemical liquefaction process to produce oil and/or combustible gas from the algae. Such methods of producing fuel grade oils and gases from algal biomass are well known in the art (e.g., see, Dote, Yutaka, "Recovery of liquid fuel from hydrocarbon rich microalgae by thermochemical liquefaction," *Fuel*. 73:Number 12. (1994); Ben-Zion Ginzburg, "Liquid Fuel (Oil) From Halophilic Algae: A renewable Source of Non-Polluting Energy, Renewable Energy," Vol. 3, No 2/3. pp. 249-252, (1993); Benemann, John R. and Oswald, William J., "Final report to the DOE: System and Economic Analysis of Microalgae Ponds for Conversion of $CO_2$ to Biomass." DOE/PC/93204-T5, March 1996; and Sheehan et al., 1998; each incorporated by reference).

In certain embodiments, especially those involving combustion facilities for which it may be required by regulation to release the photobioreactor-treated gases into the atmosphere through a smoke stack of a particular height (i.e. instead of venting the treated gas directly to atmosphere as previously described), treated gas stream 936 could be injected into the bottom of a smoke stack 938 for release to the atmosphere. In certain embodiments, treated gas stream 936 may have a temperature that is not sufficient to enable it to be effectively released from a smoke stack 938. In such embodiments, cool treated flue gas 936 may be passed through a heat exchanger 940 to increase its temperature to a suitable level before injection into the smoke stack. In one such embodiment, cooled treated flue gas stream 936 is heated in heat exchanger 940 via heat exchange with the hot flue gas released from the combustion facility, which is fed as a heat source to heat exchanger 940.

As is apparent from the above description, integrated photobioreactor gas treatment system 900 can provide a biotechnology-based air pollution control and renewable energy solution to fossil fuel burning facilities, such as power generating facilities. The photobioreactor systems can comprise emissions control devices and regeneration systems that can remove gases and other pollutants, such as particulates, deemed to be hazardous to people and the environment. Furthermore, the integrated photobioreactor system provides biomass that can be used as a source of renewable energy, and as a source of products comprising organic molecules, such as diesel fuel/gasoline substitutes and plastics, which are currently typically manufactured from fossil fuels, thereby reducing the requirement of burning fossil fuels. In addition to the combustion and biological processes described herein, an integrated photobioreactor gas treatment system may include a non-combustion chemical process producing $CO_2$ as a byproduct.

In addition, in certain embodiments, integrated photobioreactor combustion gas treatment system 900 can further include, as part of the integrated system, one or more additional gas treatment apparatus in fluid communication with the photobioreactors. For example, an effective, currently utilized technology for control of mercury and/or mercury-containing compounds in flue gases is the use of activated carbon or silica injection (e.g. see, "Mercury Study Report to Congress," EPA-452/R-97-010, Vol. VIII, (1997); (hereinafter "EPA, 1997"), which is incorporated herein by reference). The performance of this technology, however, is highly temperature dependant. Currently, effective utilization of this technology requires substantial cooling of flue gases before the technology can be utilized. In conventional combustion facilities, this requires additional capital outlay and operational costs to install flue gas cooling devices.

Advantageously, because flue gases are already cooled within integrated system 900 through utilization of the flue gases for drying the algae in dryer 912, mercury and mercury-containing removal apparatus and treatments can readily and advantageously be integrated into the cool flue gas flow path, upstream 942 of the photobioreactors and/or downstream 944 of the photobioreactors. In either case, the reduced-temperature flue gas produced within integrated system 900 is highly compatible with known mercury controlled technologies, allowing a multi-pollutant ($NO_x$, $CO_2$, mercury) control system.

Similarly, a variety of known precipitation-based $SO_x$ removal technologies also require cooling of flue gas (e.g. see, EPA, 1997). Accordingly, as with the mercury removal technologies discussed above, such $SO_x$ precipitation and removal technologies could be installed in fluid communication with the photobioreactors in system 900 in similar locations (e.g., 942 and 944) as the above-described mercury removal systems.

Figure 12:
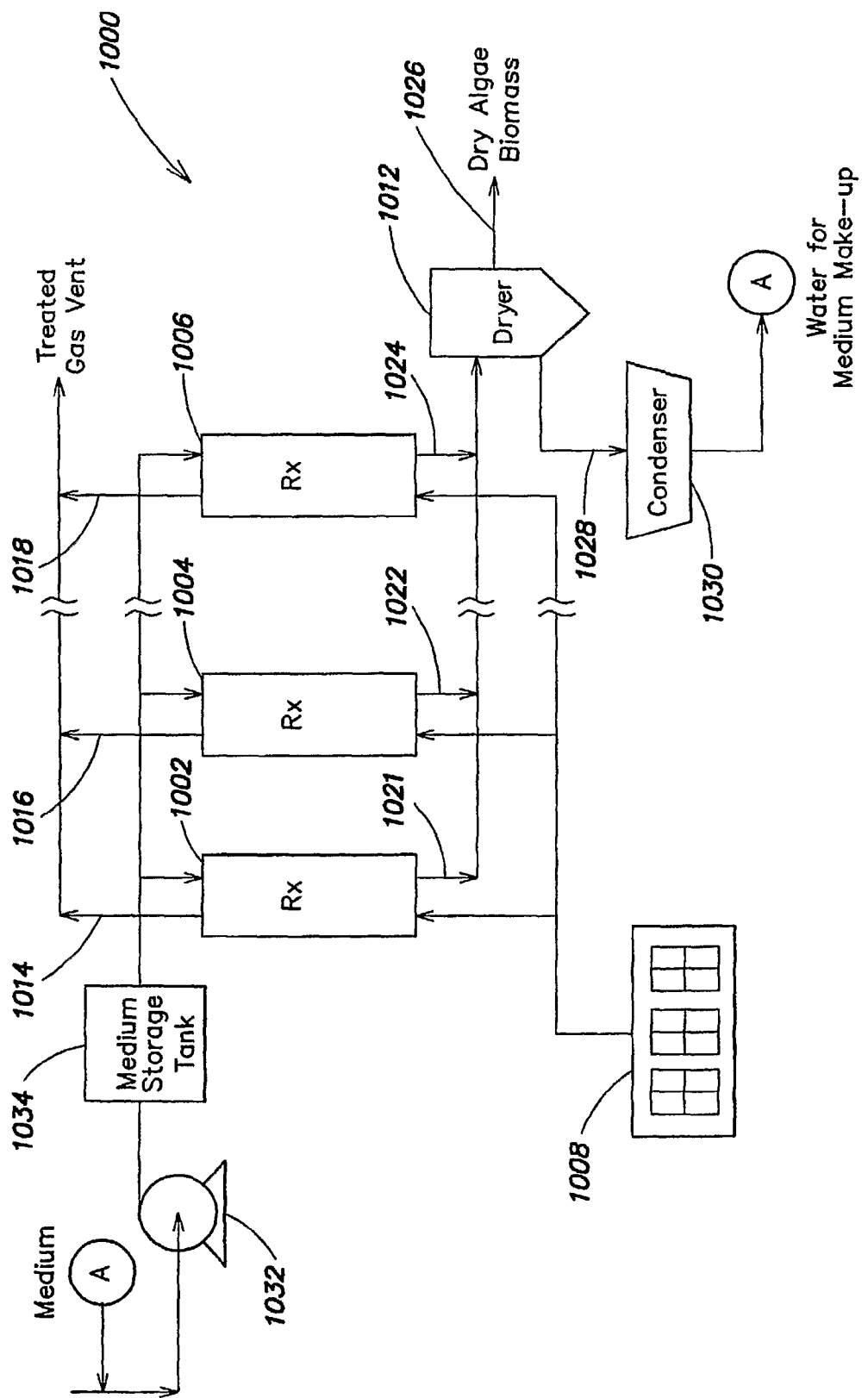
FIG. 12 is a process flow diagram of one embodiment of an integrated wastewater treatment method, according to one embodiment of the invention.

FIG. 12 illustrates one embodiment of an integrated system for performing an industrial biological process, such as fermentation or waste (e.g. agricultural waste or sewage/wastewater) digestion wherein gases are treated with a photobioreactor system to mitigate pollutants and to produce biomass, for example in the form of harvested algae. As with system 900 for performing an integrated combustion method described above, integrated system 1000 can be advantageously utilized to both reduce the level of pollutants emitted from a facility into the atmosphere and, in certain embodiments, to produce a biomass fuel and/or produce a non-fossil, clean fuel, such as hydrogen or biodiesel, from the biomass. Such a system can potentially be advantageously used for treating gases emitted by facilities such as wastewater treatment plants, industrial fermenters, agricultural waste digesters, or other facilities housing biological processes.

Integrated system 1000 includes one or more photobioreactors or photobioreactor arrays 1002, 1004, and 1006. In certain embodiments, these photobioreactors can be similar or identical in design and configuration to those previously-described in any of FIGS. 1A, 1B, 3A-3D, 5A-5E, 6A, 6B, and 7A. In alternative embodiments, other embodiments of the inventive photobioreactors could be utilized or conventional photobioreactors could be utilized. Except for embodiments wherein system 1000 utilizes photobioreactors provided according to the present invention (in which the photobioreactors are inventive and not conventional), the unit operations illustrated in FIG. 12 can be of conventional designs, or of straightforward adaptations or extensions of conventional designs, and can be selected and designed by those of ordinary skill in the chemical engineering arts using routine engineering and design principles.

In the illustrated, exemplary system, gases produced by biological processes in plant facility 1008 are injected into the photobioreactor arrays 1002, 1004, and 1006. The gas, upon passing through the photobioreactors is treated by the algae or other photosynthetic organisms therein to remove one or more pollutants therefrom, for example, $CO_2$. Treated gas, containing a lower concentration of $CO_2$ (and/or other pollutants removed by the organisms) than the injected gas, is released from gas outlets 1014, 1016, and 1018 and, in one embodiment, vented to the atmosphere.

As described above, algae or other photosynthetic organisms contained within the photobioreactors can utilize the $CO_2$ of the feed gas stream for growth and reproduction thereby producing biomass. As described above, in order to maintain optimal levels of algae or other photosynthetic organisms within the photobioreactors, periodically, biomass, for example in the form of wet algae, is removed from the photobioreactors through liquid medium outlet lines 1021, 1022, and 1024.

From there, the wet algae may be directed to a dewatering device, such as a centrifuge (not shown), and/or dryer 1012, thereby producing a dried algae biomass, which is removed via line 1026.

The water, or a portion thereof, that is removed from the wet algae stream that was fed to dryer 1012 can be fed via line 1028 to a condenser 1030 to produce water that can be used for preparation of fresh photobioreactor liquid medium. In the illustrated embodiment, water recovered from condenser 1030 (at "A"), after optional filtration to remove particulates accumulated in dryer 1012, or other treatment to remove potential contaminants, can be pumped by a pump 1032 to a medium storage tank 1034, which feeds make up medium to the photobioreactors.

The function and advantage of these and other embodiments of the present invention may be more fully understood from the examples below. The following examples, while illustrative of certain embodiments of the invention, do not exemplify the full scope of the invention.

EXAMPLE 1

Mitigation of $CO_2$ and $NO_x$ and Algae Production in Inclined Split Tube Photobioreactor Systems and a Triangular Tubular Photobioreactor System Four different photobioreactor systems were tested to investigate their algae production capabilities per photobioreactor footprint area. System 1 included an array of ten substantially triangular photobioreactors similar to those described in commonly owned PCT Publication No. WO 03/094598, incorporated herein by reference. System 1 included a solar panel conduits inclined at approximately 60 degrees relative to horizontal. Each conduit had an about 4 inch inner diameter and a length of about 9 feet 7 inches and the overall system had a working volume of approximately 900 liters. The reactors of system 1 had a total footprint area of about 1.435 $m^2$. Each of systems 2-4 included a single conduit photobioreactor including a partition therein forming two channels, as described previously in the context of FIG. 1A, each conduit had a length of about 9 feet 7 inches and was inclined at approximately 60 degrees. System 2 had an about 10 inch inner diameter conduit, an approximate volume of 140 liters, and a photobioreactor footprint area of about 0.3588 $m^2$. System 3 had an about 12 inch inner diameter conduit, an approximate volume of 200 liters, and a footprint area of about 0.4306 $m^2$. System 4 had an about 14 inch inner diameter conduit, an approximate volume of 270 liters, and a footprint area of about 0.5023 $m^2$.

A modified F/2 liquid medium containing Chaetoceros Muelleri (CCMP1316) algae was introduced into the photobioreactors. The liquid medium contained: 22 g/l NaCl, 16 g/l Artificial Sea Water Sea Salts (INSTANT OCEAN®, Aquarium Systems, Inc. Mentor, Ohio), 0.425 g/l $NaNO_3$, 1 ml of 30 g/l $Na_2SiO_3 \cdot 9H_2O$ solution per liter medium, 1 ml of 5 g/l $NaH_2PO_4$ solution per liter medium, and 1 ml Metal Solution per liter medium (see contents of stock solution below)+5 ml Vitamin Solution (see contents of stock solution below) per liter medium. The pH was maintained at pH 8. Stock Solution Compositions:

| Metal Solution- Trace metals stock solution (chelated) per liter | |
|---|---|
| $EDTANa_2$ | 4.160 g |
| $FeCl_3 \cdot 6H_2O$ | 3.150 g |
| $CuSO_4 \cdot 5H_2O$ | 0.010 g |
| $ZnSO_4 \cdot 7H_2O$ | 0.022 g |
| $CoCl_2 \cdot 6H_2O$ | 0.010 g |
| $MnCl_2 \cdot 4H_2O$ | 0.180 g |
| $Na_2MoO_4 \cdot 2H_2O$ | 0.006 g |
| Vitamin Solution- Vitamin stock solution per liter | |
| Cyanocobalamin | 0.0005 g |
| Thiamine HCl | 0.1 g |
| Biotin | 0.0005 g |

Gas input was via direct injection of flue gas from the Massachusetts Institute of Technology's (MIT's) Cogeneration Plant in Cambridge Mass. The flue gas was cooled to approximately 100 degrees F. and then injected directly into the photobioreactors without any pretreatment. The volume of gas per volume of liquid medium per minute (vvm) was approximately 0.03 for each of the four systems, the volume being split approximately evenly between the two spargers of each system, resulting in a flow rate of approximately 0.015 vvm per sparger. The flue gas had a typical $CO_2$ concentration of 2-4% and a typical $NO_x$ concentration of 8-15 ppm. The liquid medium was maintained at a temperature of between 20 and 30 degrees centigrade using an internal heat exchanger as illustrated in FIGS. 8A-8C. On weekdays, each day, 30% of the liquid medium was drained from the photobioreactors and then an equal amount of fresh medium was added to the photobioreactors.

Before draining the liquid medium, the optical density of the liquid medium was measured at a wavelength of 727 nanometers. This optical density measurement is assumed to be linearly related to biomass concentration. Cell density was calculated using spectrophotometer measurements at 727 nm (see, Hiroyasu et al., 1998). To calculate the daily productivity of each system, the total harvested biomass for one week was divided by seven days. This daily productivity was then divided by the photobioreactor footprint area to arrive at a value for daily productivity per square meter of photobioreactor footprint. The following chart shows the productivity results for each of systems 1-4 for each of three weeks of testing. Each value provides the average daily productivity of algae in grams per square meter of photobioreactor footprint for a given week.

|  | System 1 (triangular system with 4" solar conduit) | System 2 (single conduit with 10" diameter) | System 3 (single conduit with 12" diameter) | System 4 (single conduit with 14" diameter) |
| --- | --- | --- | --- | --- |
| Week 1 | 21.9 | 40.5 | 51.6 | 60.6 |
| Week 2 | 14.4 | 31.9 | 35.6 | 43.3 |
| Week 3 | 25.5 | 51.0 | 53.8 | 59.9 |

EXAMPLE 2

Mitigation of $CO_2$ and $NO_x$ with a Three-Photobioreactor Module including Three Triangular Tubular Photobioreactors Each photobioreactor unit of the module utilized for the present example comprised 3 tubes of essentially circular cross-section constructed from clear polycarbonate, assembled as shown in FIG. 1 of commonly owned PCT Publication No. WO 03/094598, with $\alpha_1$=about 45 degrees and $\alpha_2$=about 90 degrees. In this essentially triangular configuration, the vertical leg was about 2.2 m high and about 5 cm in inner diameter; the horizontal leg was about 1.5 m long and about 5 cm in inner diameter; and the hypotenuse was about 2.6 m long and about 10 cm in inner diameter. The photobioreactor module comprised 3 adjusted units arranged in parallel, similarly as illustrated in FIG. 2 of commonly owned PCT Publication No. WO 03/094598. This bioreactor module has a footprint of about 0.45 $m^2$ A gas mixture (certified, AGA gas), mimicking flue gas composition was used (Hiroyasu et al., 1998). The total gas flow input was about 715 ml/min per each 10 liter photobioreactor in the module. Gas distribution to the spargers injecting gas into the vertical legs and the to the spargers injecting gas into the hypotenuse legs was 50:50. Mean bubble size was about 0.3 mm. $CO_2$ and $NO_x$ composition at the bioreactor inlet and outlet ports was measured using a flue gas analyzer (QUINTOX™; Keison Products, Grants Pass, Oreg.).

Light source, applied only to the hypotenuse legs, was a full-spectrum "SUNSHNE™" lamps, with a radiation intensity of about 390 $W/m^2$. Light radiation was measured with using TES light meter (TES Electrical Electronic Corp., Taipei, Taiwan, R.O.C.). Light cycle was 12 h light-12 h dark. The temperature was maintained at about 26 degrees C.

Algal heat value was measured using a micro oxygen bomb calorimeter per Burlew, 1961.

The microalgae *Dunaliella parva* (UTEX.) culture was used as a model. It was specifically chosen for its proven track record in large scale production, tolerance to flue gas composition and, ability to produce high-quality biofuel.

Medium used was modified F/2 containing: 22 g/l NaCl, 16 g/l Artificial Sea Water Sea Salts (INSTANT OCEANS, Aquarium Systems, Inc. Mentor, Ohio), 0.425 g/l $NaNO_3$, 1 ml of 30 g/l $Na_2SiO_3.9H_2O$, and 1 ml Metal Solution per liter medium (see contents of stock solution below)+5 ml Vitamin Solution (see pH contents of stock solution below) per liter medium. The pH was maintained at pH 8.

Stock Solution Compositions:

| Metal Solution- Trace metals stock solution (chelated) per liter | |
| --- | --- |
| $EDTANa_2$ | 4.160 g |
| $FeCl_3 \cdot 6H_2O$ | 3.150 g |
| $CuSO_4 \cdot 5H_2O$ | 0.010 g |
| $ZnSO_4 \cdot 7H_2O$ | 0.022 g |
| $CoCl_2 \cdot 6H_2O$ | 0.010 g |
| $MnCl_2 \cdot 4H_2O$ | 0.180 g |
| $Na_2MoO_4 \cdot 2H_2O$ | 0.006 g |
| Vitamin Solution- Vitamin stock solution per liter | |
| Cyanocobalamin | 0.0005 g |
| Thiamine HCl | 0.1 g |
| Biotin | 0.0005 g |

Cell density was calculated using spectrophotometer measurements at 680 nm (see, Hiroyasu et al., 1998).

Under the experimental conditions, the following performance was achieved:
90% $CO_2$ mitigation (in the presence of light);
98% and 71% $NO_x$ removal (in light and dark, respectively);
solar efficiency of 19.6%.

EXAMPLE 3

Mitigation of $CO_2$ and $NO_x$ with a Photobioreactor Module including Thirty Triangular Tubular Photobioreactors Each photobioreactor unit of the module utilized for the present example comprised 3 tubes of essentially circular cross-section constructed from clear polycarbonate, assembled as shown in FIG. 1 of commonly owned PCT Publication No. WO 03/094598, with $\alpha_1$=about 63 degrees and $\alpha_{2=90}$ degrees. In this essentially triangular configuration, the essentially vertical leg was 2.4 m high and 6.35 cm in diameter; the essentially horizontal leg was 1.22 m long and 5.08 cm in diameter; and the hypotenuse was 2.72 m long and 10.16 cm in diameter. The photobioreactor module comprised 30 adjusted units arranged in parallel, similarly as illustrated in FIG. 2 of commonly owned PCT Publication No. WO 03/094598. This bioreactor module has a footprint of about 3.72 $m^2$ Gas input was via direct injection of flue gas from the Massachusetts Institute of Technology's (MIT's) Cogeneration Plant in Cambridge Mass. The total gas flow input was about 1000 ml/min per each photobioreactor in the module. Gas distribution to the spargers injecting gas into the vertical legs and to the spargers injecting gas into the hypotenuse legs was about 50:50. Mean bubble size was about 0.3 mm.

Monitoring methods used were pursuant to U.S. EPA testing procedures prescribed by the Code of Federal Regulations (CFR) Title 40, Protection of Environment, Part 60 Appendix A. Specifically, determination of oxygen and carbon dioxide concentrations were performed according to Method 3A, and determination of nitrogen oxides emissions were performed according to Method 7E. $CO_2$ and $NO_x$ composition at the bioreactor inlet and outlet ports was measured. $CO_2$ was measured using a $CO_2$ infrared gas analyzer (California Analytical Instruments, Model 3300), and $NO_x$ was measured using a $NO$—$NO_2$—$NO_x$ chemiluminescence gas analyzer (Thermo Environmental Instruments, Model 42). Sunlight photon flux was measured with a Li—Co 1400 photon flux sensor. The temperature was maintained between 20-30 degrees C.

The microalgae *Dunaliella tertiolecta* (UTEX# LB999.) in culture was used as a model. It was specifically chosen for its proven track record in large scale production, tolerance to flue gas composition and, ability to produce high-quality biofuel.

Medium used was modified F/2 containing:

22 g/l NaCl, 16 g/l Artificial Sea Water Sea Salts (INSTANT OCEAN®, Aquarium Systems, Inc. Mentor, Ohio), 0.425 g/l $NaNO_3$, 1 ml of 30 g/l $Na_2SiO_3.9H_2O$, and 1 ml Metal Solution per liter medium (see contents of stock solution below)+5 ml Vitamin Solution (see contents of stock solution below) per liter medium. The pH was maintained at pH 8.

Stock Solution Compositions:

| Metal Solution- Trace metals stock solution (chelated) per liter | |
|---|---|
| $EDTANa_2$ | 4.160 g |
| $FeCl_3•6H_2O$ | 3.150 g |
| $CuSO_4•5H_2O$ | 0.010 g |
| $ZnSO_4•7H_2O$ | 0.022 g |
| $CoCl_2•6H_2O$ | 0.010 g |
| $MnCl_2•4H_2O$ | 0.180 g |
| $Na_2MoO_4•2H_2O$ | 0.006 g |
| Vitamin Solution- Vitamin stock solution per liter | |
| Cyanocobalamin | 0.0005 g |
| Thiamine HCl | 0.1 g |
| Biotin | 0.0005 g |

Figure 13A:
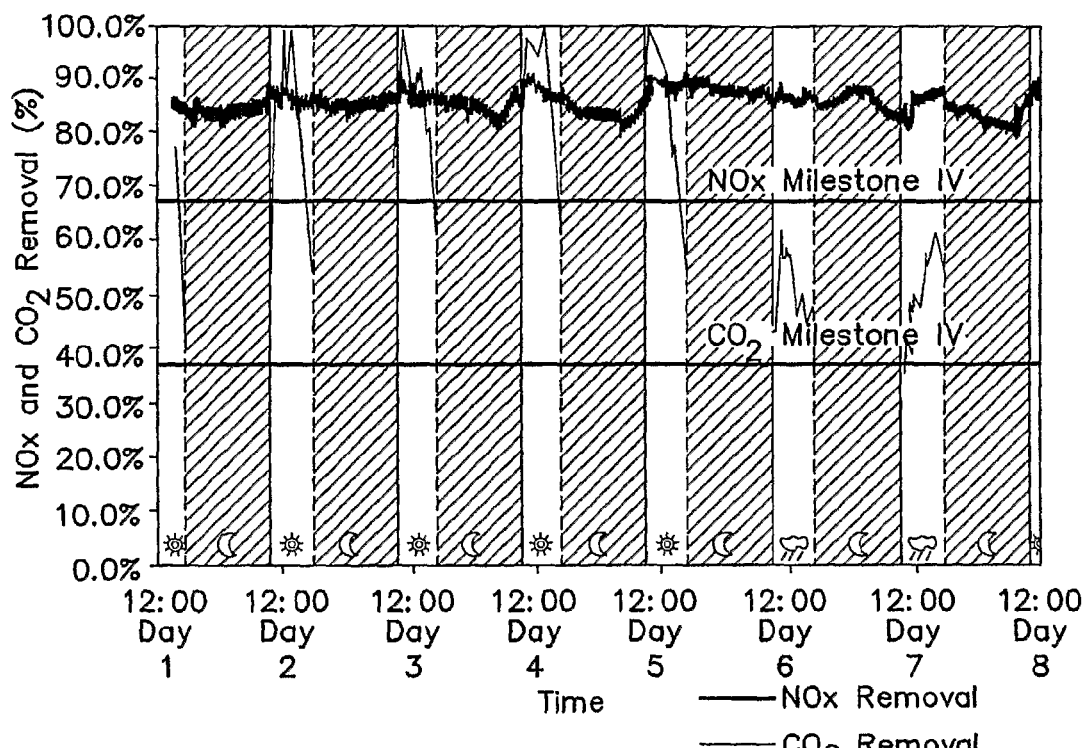
FIG. 13A is a graph illustrating $NO_x$ and $CO_2$ removal from flue gas by a thirty (30) unit photobioreactor module over a seven (7) day test period.
Figure 13B:
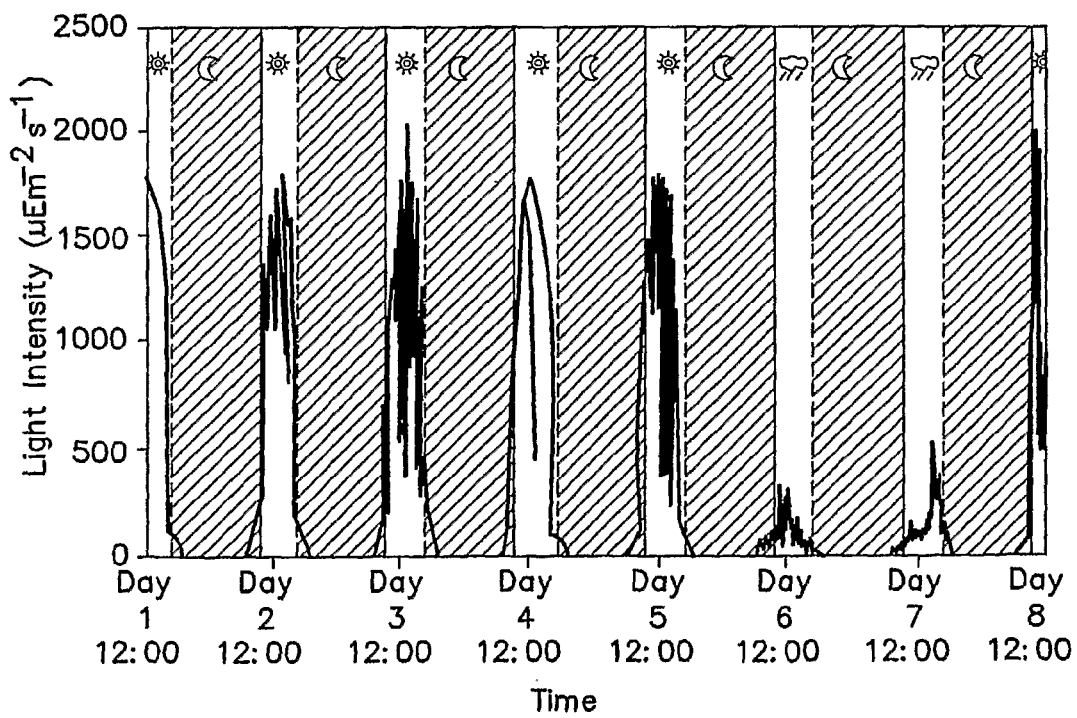
FIG. 13B is a graph illustrating light intensity over the seven (7) day test period corresponding to the $NO_x$ and $CO_2$ removal results illustrated in FIG. 13A.

Measurements were conducted over a one week period, beginning at noon on the Day 1 and ending at noon on Day 8. The results for percent $NO_x$ and $CO_2$ removal over the period are illustrated in FIG. 13A, for corresponding measured light intensities illustrated in FIG. 13B. The overall performance is summarized in Table 2 below:

TABLE 2

| Overal Performance of 30 Unit Photobioreactor Module | | |
|---|---|---|
| | $CO_2$ Reduction* | $NO_x$ Reduction** |
| Sunny days | 82.3 ± 12.5% | 85.9 ± 2.1% |
| Cloudy days | 50.1 ± 6.5% | 85.9 ± 2.1% |

*data measured 9 a.m.-5 p.m.
**data measured 24 hrs./day

EXAMPLE 4

Use of a Small-Scale Automated Photobioreactor Cell Culture System for Preconditioning of Algal Cultures to High Intensity Illumination and Photomodulation A culture of the microalgae *Dunaliella parva* (UTEX.) was grown and adapted, as described below, using a small-scale photobioreactor system similar to that illustrated in FIGS. 10A-10F. The medium used was the same modified F/2 described in Example 2. The cell culture module had an internal culture volume of about 10 ml. Gas exchange was performed utilizing a silicone-coil gas exchanger, similar to gas exchanger 862 of FIG. 10A, which was fed a gas mixture comprising 8% $CO_2$ (balance air) at a rate of 100 ml/min. Flow rate of liquid medium in the perfusion loop was about 1 min net forward flow. The culture was stirred using magnetic stir bars rotated at about 40 RPM. The culture was maintained at room temperature (about 25 degrees C.). Cell density was monitored with a spectrophotometer, and culture dilutions were made as necessary to maintain growth of the culture (maintained within an operating range near the upper end of the concentration in which the algae is still in the log growth regime). Typically, such dilutions were performed at least once per day during the adaptation period. Initially, the culture was grown under steady illumination of about 150 $\mu Em^{-2}s^{-1}$. The above conditions are referred to below as the "initial conditions."

In a test culture, illumination intensity was increased by 50 $\mu Em^{-2}s^{-1}$ once per day until a level of 300 $\mu Em^{-2}s^{-1}$ was reached. At this point, a light source modulator utilizing a chopper wheel (similar to light source modulator 830 illustrated in FIGS. 10A and 10G) was used to subject the test culture to a photomodulation pattern of repetitive cycles of 0.5 second light exposure followed by 0.2 second dark exposure. This photomodulation pattern was maintained for the rest of the adaptation period for the test culture. For the remainder of the adaptation period, light intensity was increased once per day in 50 $\mu Em^{-2}s^{-1}$ intervals until an illumination intensity of 2,000 $\mu Em^{-2}s^{-1}$ was reached. Total adaptation time was about 40 days, with the final conditions referred to below as the "test conditions."

At the end of this period, a control culture grown only under the initial conditions was exposed to culture at the test conditions and growth rate was measured for both the adapted culture and the control culture under the test conditions. It was found that the doubling time of the control culture grown under the test conditions was about 20 hours, while that of the adapted culture was about 6 hours.

While several embodiments of the invention have been described and illustrated herein, those of ordinary skill in the art will readily envision a variety of other means and structures for performing the functions and/or obtaining the results or advantages described herein, and each of such variations, modifications and improvements is deemed to be within the scope of the present invention. More generally, those skilled in the art would readily appreciate that all parameters, dimensions, materials, and configurations described herein are meant to be exemplary and that actual parameters, dimensions, materials, and configurations will depend upon specific applications for which the teachings of the present invention are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described. The present invention is directed to each individual feature, system, material and/or method described herein. In addition, any combination of two or more such features, systems, materials and/or methods, provided that such features, systems, materials and/or methods are not mutually inconsistent, is included within the scope of the present invention. In the claims (as well as in the specification above), all transitional phrases or phrases of inclusion, such as "comprising," "including," "carrying," "having," "containing," "composed of," "made of," "formed of," "involving" and the like shall be interpreted to be open-ended, i.e. to mean "including but not limited to" and, therefore, encompassing the items listed thereafter and equivalents thereof as well as additional items. Only the transitional phrases or phrases of inclusion "consisting of" and "consisting essentially of" are to be interpreted as closed or semi-closed phrases, respectively. The indefinite articles "a" and "an," as used herein in the specification and in the claims, unless clearly indicated to the contrary, should be understood to mean "at least one." The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified. Thus, as a non-limiting example, a reference to "A and/or B" can refer, in one embodiment, to A only (optionally including elements other than B); in another embodiment, to B only (optionally including elements other than A); in yet another embodiment, to both A and B (optionally including other elements); etc. As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements that the phrase "at least one" refers to, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc. In cases where the present specification and a document incorporated by reference and/or referred to herein include conflicting disclosure, and/or inconsistent use of terminology, and/or the incorporated/referenced documents use or define terms differently than they are used or defined in the present specification, the present specification shall control.

What is claimed is:

1. A method comprising acts of:
exposing a liquid medium comprising at least one species of photosynthetic organisms therein to a defined set of growth conditions, which are selected to simulate conditions to which the photosynthetic organisms will subsequently be exposed in a photobioreactor, to precondition the photosynthetic organisms to the defined set of growth conditions, the step of exposing being performed over a period sufficient for the photosynthetic organisms to undergo multiple generational natural selection and adaptation;
harvesting photosynthetic organisms preconditioned in the exposing step; and
inoculating a photobioreactor with at least a portion of the harvested photosynthetic organisms.

2. A method as recited in claim 1, wherein the exposing act is performed utilizing an automated cell culture and testing system comprising at least one culture chamber comprising a photobioreactor having an internal volume between about 1 microliter and about 1 liter.

3. A method as recited in claim 2, wherein the automated cell culture and testing system comprises a source of artificial light capable of driving photosynthesis configured and positioned to direct light to an inner volume of the cell culture chamber; and a light source modulator that is constructed and arranged to vary the intensity of the artificial light between a first intensity to a second intensity at a frequency of at least one variation per second.

4. A method as recited in claim 1, wherein the predetermined set of growth conditions that are selected to simulate conditions to which the photosynthetic organisms will subsequently be exposed in the photobioreactor include at least one of liquid medium composition, liquid medium temperature, liquid medium temperature fluctuation magnitude, frequency, and interval, pH, light intensity, light and dark exposure intervals, feed gas composition, and/or feed gas temperature.

5. A method as recited in claim 4, wherein in the exposing act, the liquid medium comprising the at least one species of photosynthetic organisms therein is exposed to the defined set of growth conditions that comprises variation of light intensity to cause photomodulation at a light/dark cycling frequency of at least one light/dark transition per minute.

6. A method as recited in claim 5, wherein in the exposing act, the liquid medium comprising the at least one species of photosynthetic organisms therein is exposed to the defined set of growth conditions that comprises variation of light intensity to cause photomodulation at a light/dark cycling frequency of at least one light/dark transition per 30 seconds.

7. A method as recited in claim 6, wherein in the exposing act, the liquid medium comprising the at least one species of photosynthetic organisms therein is exposed to the defined set of growth conditions that comprises variation of light intensity to cause photomodulation at a light/dark cycling frequency of at least one light/dark transition per 10 seconds.

8. A method as recited in claim 7, wherein in the exposing act, the liquid medium comprising the at least one species of photosynthetic organisms therein is exposed to the defined set of growth conditions that comprises variation of light intensity to cause photomodulation at a light/dark cycling frequency of at least one light/dark transition per 5 seconds.

9. A method as recited in claim 8, wherein in the exposing act, the liquid medium comprising the at least one species of photosynthetic organisms therein is exposed to the defined set of growth conditions that comprises variation of light intensity to cause photomodulation at a light/dark cycling frequency of at least one light/dark transition per second.

10. A method as recited in claim 9, wherein in the exposing act, the liquid medium comprising the at least one species of photosynthetic organisms therein is exposed to the defined set of growth conditions that comprises variation of light intensity to cause photomodulation at a light/dark cycling frequency of at least one light/dark transition per ½ second.

11. A method as recited in claim 10, wherein in the exposing act, the liquid medium comprising the at least one species of photosynthetic organisms therein is exposed to the defined set of growth conditions that comprises variation of light intensity to cause photomodulation at a light/dark cycling frequency of at least one light/dark transition per 1/10 second.

12. A method as recited in claim 11, wherein in the exposing act, the liquid medium comprising the at least one species of photosynthetic organisms therein is exposed to the defined set of growth conditions that comprises variation of light intensity to cause photomodulation at a light/dark cycling frequency of at least one light/dark transition per 1/100 second.

13. A method as recited in claim 12, wherein in the exposing act, the liquid medium comprising the at least one species of photosynthetic organisms therein is exposed to the defined set of growth conditions that comprises variation of light intensity to cause photomodulation at a light/dark cycling frequency of at least one light/dark transition per millisecond.

14. A method as recited in claim 4, wherein in the exposing act, the liquid medium comprising the at least one species of photosynthetic organisms therein is exposed to the defined set of growth conditions that comprises exposure of the at least one species of photosynthetic organisms to a source of light capable of driving photosynthesis incident upon at least a portion of the photosynthetic organisms at an intensity at least that known to be capable of causing a reduction in the growth rate of a starter culture via photoinhibition.

15. A method as recited in claim 4, wherein in the exposing act, the liquid medium comprising the at least one species of photosynthetic organisms therein is exposed to the defined set of growth conditions that comprises exposure of the at least one species of photosynthetic organisms to a source of light capable of driving photosynthesis incident upon at least a portion of the photosynthetic organisms at an intensity at least twice that known to be capable of causing a reduction in the growth rate of an unadapted sample comprising the at least one species of photosynthetic organisms therein via photoinhibition.

16. A method as recited in claim 1, further comprising exposing the harvested photosynthetic organisms in the photobioreactor to the defined set of growth conditions.

17. A method as recited in claim 1, further comprising, before exposing the liquid medium to the defined set of growth conditions, successively exposing the liquid medium to growth conditions that increasingly approximate the defined set of growth conditions over multiple doubling times of the at least one species of photosynthetic organism.

18. A method as recited in claim 17, wherein successively exposing the liquid medium to growth conditions that increasingly approximate the defined set of growth conditions includes only varying one growth condition at a time to approximate the defined set of growth conditions.

19. A method as recited in claim 1, wherein the period exceeds five doubling times of the at least one species of photosynthetic organism.

20. A method as recited in claim 1, wherein the period exceeds 100 doubling times of the at least one species of photosynthetic organism.

21. A method as recited in claim 1, wherein the defined set of growth conditions includes a concentration of $NO_x$.

22. A method as recited in claim 1, wherein the defined set of growth conditions includes a concentration of $SO_x$.

23. A method as recited in claim 1, wherein the defined set of growth conditions includes a concentration of a heavy metal.

* * * * *